US009464325B2

(12) United States Patent
Petrovics et al.

(10) Patent No.: US 9,464,325 B2
(45) Date of Patent: Oct. 11, 2016

(54) METHODS OF DIAGNOSING OR TREATING PROSTATE CANCER USING THE ERG GENE, ALONE OR IN COMBINATION WITH OTHER OVER OR UNDER EXPRESSED GENES IN PROSTATE CANCER

(75) Inventors: Gyorgy Petrovics, Bethesda, MD (US); Shiv Srivastava, Potomac, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

(21) Appl. No.: 13/534,529

(22) Filed: Jun. 27, 2012

(65) Prior Publication Data
US 2012/0295282 A1 Nov. 22, 2012

Related U.S. Application Data

(62) Division of application No. 11/579,695, filed as application No. PCT/US2005/015926 on May 6, 2005.

(60) Provisional application No. 60/568,822, filed on May 7, 2004, provisional application No. 60/622,021, filed on Oct. 27, 2004.

(51) Int. Cl.
*G01N 33/53* (2006.01)
*C12Q 1/68* (2006.01)
*C07K 16/30* (2006.01)

(52) U.S. Cl.
CPC .............. *C12Q 1/6886* (2013.01); *C07K 16/30* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,514,751 B2 | 2/2003 | Johann et al. | |
| 2001/0010934 A1 | 8/2001 | Libermann et al. | |

FOREIGN PATENT DOCUMENTS

| | | |
|---|---|---|
| FR | 2 817 043 | 5/2002 |
| JP | 2002/360255 | 12/2002 |
| WO | 98/45420 | 10/1998 |
| WO | 9845420 | 10/1998 |
| WO | 01/88122 | 11/2001 |
| WO | 0188124 | 11/2001 |
| WO | 03/016484 | 2/2003 |
| WO | 03009814 | 2/2003 |
| WO | 03053223 | 7/2003 |
| WO | 2004/031231 | 4/2004 |
| WO | 2004/076814 | 9/2004 |
| WO | 2005007830 | 1/2005 |
| WO | WO 2006/028655 A2 * | 3/2006 ............... C12Q 1/68 |
| WO | 2010/126972 | 11/2010 |

OTHER PUBLICATIONS

Tockman et al (Cancer Res., 1992, 52:2711s-2718s).*
Alberts et al. (Molecular Biology of the Cell, 3rd edition, 1994, p. 465).*
Greenbaum et al. (Genome Biology, 2003, vol. 4, Issue 9, pp. 117.1-117.8).*
Reddy et al (PNAS, 1987, 84: 6131-6135).*
Gavrilov et al (European Journal of Cancer, 2001, 37: 1033-1040).*
Ernst et al (American Journal of Pathology, 2002, 160(6): 2169-2180).*
Tsujimoto et al (International Journal of Urology, 2002, 9: 167-172).*
Luo et al (Cancer Res, 2002, 62: 2220-2226).*
Rao et al (Science, 1987, 237: 635-639).*
Luo et al. α-Methylacl-CoA Racemase: A New Molecular Marker for Prostate Cancer. Cancer Research, 2002, vol. 62, pp. 2220-2226.
Shaheduzzaman et al. Evaluation of Prostate Cancer Associated Gene Expression Patterns in High Risk Prostate Cancer Patients. Journal of Erology, 2003, vol. 169, No. 4, (Supp.), pp. 51-52.
Xu et al. Quantitative Expression Profile of Androgen-Regulated Genes in Prostate Cancer Cells and Identification of Prostate-Specific Genes. International Journal of Cancer, 2001, vol. 92, pp. 332.328.
Sun et al. A Human Novel Gene DERPC Located on 16q22.1 Inhibits Prostate Tumor Cell Growth and Its Expression is Decreased in Prostate and Renal Tumors. Molecular medicine. 2002, vol. 8, pp. 655.663.
Brooks, James D. Microarray Analysis in Prostate Cancer Research. Current Opinion in Urology, 2002, vol. 12, pp. 395-399.
Hinzman et al. Human prostatic carcinoma derived DNA SEQ ID 84 #4, Dec. 2, 2004, retrieved from EBI acession No. GSN:ADR66792.
Baldus et al. Acute myeloid leukemia with complex karyotypes and abnormal chromosome 21: Amplification discloses overexpression of APP, ETS2, and ERG Genes. PNAS, 2004 vol. 101, pp. 3915-3920.
Carrere et al. Erg proteins, transcription factors of the Ets family, form homo, heterodimers, and ternary complexes via two distinct domains. Institute de Biologie de Lille, France, Jan. 25, 1998, pp. 3261-3268.

(Continued)

*Primary Examiner* — Sean Aeder
(74) *Attorney, Agent, or Firm* — MH2 Technology Law Group, LLP

(57) ABSTRACT

The present invention relates to oncogenes or tumor suppressor genes, as well as other genes, involved in prostate cancer and their expression products, as well as derivatives and analogs thereof. Provided are therapeutic compositions and methods of detecting and treating cancer, including prostate and other related cancers. Also provided are methods of diagnosing and/or prognosing prostate cancer by determining the expression level of at least one prostate cancer-cell-specific gene, including, for example, the ERG gene or the LTF gene alone, or in combination with at least one of the AMACR gene and the DD3 gene.

28 Claims, 17 Drawing Sheets

(56) References Cited

OTHER PUBLICATIONS de Alava et al. Ewing Tumor: Tumor Biology and Clinical Applications. International Journal of Surgical Pathology, Jan. 1, 2001, vol. 9, pp. 7-17.

Gavrilov et al. Expression of urokinase plasminogen activator and receptor in conjuction with the ets family and AP-1 complex transcription factors in high grade prostate cancers. European Journal of Cancer, Jan. 18, 2001, vol. 37, pp. 1033-1040.

Liu et al. Identification of Differentially Expressed Prostate Genes: Increased Expression of Transcription Factor ETS-02 in Prostate Cancer. The Prostate. 1997. 1997. vol. 30, pp. 145-153.

Nelson et al. Preneoplastic Prostate Lesions, and Opportunity for Prostate Cancer Prevention. Annals New York Academy of Sciences, pp. 135-144.

Oikawa et al. Molecular biology of the Ets family transcription factors. Gene, 2003, vol. 303, pp. 11-34.

Owczarek et al. Detailed mapping of the ERG-ETS2 interval of human chromosome 21 and comparison with the region of conserved syntery on mouse chromosome 16. Gene, 2004, vol. 324, pp. 65-77.

Park et al. Organization of the human transferrin gene: Direct evidence that it originated by gene duplication. Proc. Natl. Acad. Sci. USA, May 1985, vol. 82, pp. 3149-3153.

Rao et al. erg, a Human ets-Related Gene on Chromosome 21: Alternative S;icing, Polyadenylation, and Translation, Science, Aug. 7, 1987, vol. 237, pp. 635-639.

Rubin et al. α-Methylacyl Coenzyme A Racemase as a Tissue Biomarker for Prostate Cancer, Journal of the American Medical Association Jan. 9, 2002, vol. 287, No. 13, pp. 1662-1670.

Sementchenko et al. ETS2 function is required to maintain the transformed state of human prostate cancer cells. Oncogene, Jun. 16, 1198, vol. 17, pp. 2883-2888.

Seth et al. c-ets-2 protooncogene has mitogenic and oncogenic activity. Proc. Natl. Acad. Sci., Oct. 1989, vol. 86, pp. 7833-7837.

Sharrocks, Andrew D. The ETS-Domain Transcription Factor Family. Nature Reviews—Molecular Cell Biology, Nov. 2001, vol. 2, pp. 827-837.

Shimizu et al., An ets-related gene, ERG, is rearranged in human myeloid leukemia with t(16:21) chromosomal translocation. Proc. Natl. Acad. Sci. USA, Nov. 1993, vol. 90, pp. 10280-10284.

Simpson et al. Altered expression of Erg and ETs-2 transcription factors associated with genetic changes at 21q22.2-22.3 in immortal and cervical carcinoma cell lines. Oncogene, 1997, vol. 154. pp. 2149-2157.

Teng, Christina T. Lactoferrin gene expression and regulation: an overview. Biochem. Cell Biol., 2002, vol. 80, pp. 7-16.

Teng et al. Lactoferrin gene expression is estrogen responsive in human and rhesus monkey endometrium. Molecular Human Reproduction, 2002, vol. 8, No. 1, pp. 58-67.

Touda et al. Cancer prevention by bovine lactoferrin and underlying mechanisms—a review of experimental and clinical studies. Biochem. Cell Biol., 2002, vol. 80, pp. 131-136.

Tsuda et al., Prevention of colon carcinogenesis and carcinoma metastatis by orally administered bovine lactoferrin in animals. Biofactors, 2002, vol. 12, pp. 83-88.

Tsuda et al. Milk and dairy products in cancer prevention: focus on bovine lactoferrin. Mutation Research, 2000, vol. 162, pp. 227-233.

van Sande et al. Lactoferrin in Human Prostate Tissue. Urological Research, 1981, vol. 9, pp. 241-244.

Vlaerninck-Guillern et al. Mutual repression of transcriptional activation between the ETS-related factor ERG and estrogen receptor. Oncogene, 2003, vol. 22, pp. 8072-8084.

Bowman et al. Transferrin: evolution and genetic regulation of expression. Adv. Genet., 1988, vol. 25, pp. 1-38.

Hart et al. Human ERG is a proto-oncogene with mitogenic and transforming activity, Oncogene, 1995, 10(7), pp. 1423-1430.

Papes et al. ETS family of genes in leukemia and Down syndrome. Am. J. Med. Genet. Suppl. , 1990, vol. 7, pp. 251-281.

International Search Report and the Written Opinion of the International Searching Authority from PCT/US2005/015926.

Oikawa, Tsuneyuki. ETS transcription factors: Possible targets for cancer therapy. Cancer Sci., 95(8): 626-633, Aug. 2004.

Gavrilov, D. et al. Expression of urokinase plasminogen activator and receptor in conjunction with the ets family and AP-1 complex transcription factors in high grade prostate cancers. European Journal of Cancer, 37 (2001) 1033-1040.

Vanaja, D. K. et al. Transcriptional Silencing of Zinc Finger Protein 185 Identified by Expression Profiling Is Associated with Prostate Cancer Progression, Cancer Research, 63, Jul. 15, 2003, 3877-3882.

Bussemakers, Marion J. G. et al., "DD3: A New Prostate-specific Gene, Highly Overexpressed in Prostate Cancer", Cancer Research 59, Dec. 1, 1999, pp. 5975-5979.

Petrovics, Gyorgy et al., "Frequent overexpression of ETS-related gene-1 (ERG1) in prostate cancer transcriptome", Oncogene, 2005, 24, pp. 3847-3852.

Ernst, Thomas et al., "Decrease and Gain of Gene Expression Are Equally Discriminatory Markers for Prostate Carcinoma, A Gene Expression Analysis on Total and Microdissected Prostate Tissue," American Journal of Pathology, vol. 160, No. 6, Jun. 2002, pp. 2169-2180.

Amanda M. de Mestre et al., "Regulation of Inducible Heparanase Gene Transcription in Activated T Cells by Early Growth Response 1," The Journal of Biological Chemistry, vol. 278, 50, Dec. 23, 2003, pp. 50377-50385.

Ogle B.A. et al. Nucleic Acids Research (2003) vol. 31, No. 22, e139, pp. 1-6.

Reddy E.S.P. et al, Proc. Natl. Acad. Sci. USA (Sep. 1987) vol. 84, pp. 6131-6135.

Traynor J. et al. BMC Medical Genetics (2002) vol. 3, No. 12, Printed pp. 1-15.

Ahern H. The Scientist, Jul. 24, 1995, pp. 20 and 22.

Liu G. et al. Nucleic Acids Research, 2003, vol. 31, No. 1, pp. 82-86.

Details for HG-U133B 232572_AT (2009), from www.affymetrix.com, Printed pp. 1-2.

Details for HG-U95AV2:36383_AT (2009), from www.affymetrix.com, Printed pp. 1-4.

Details for HG-U133B 230549_AT (2009), from www.affymetrix.com. Printed pp. 1-3.

Details for HG-U95AV2:41706_AT (2009), from www.affymetrix.com, Printed pp. 1-4.

Details for HG-U133A:217113_AT (2009), from www.affymetrix.com, Printed pp. 1-3.

Patent Examination Report No. 2 from Australian Patent Office for Australian Patent Application No. 2011213720 issued Sep. 19, 2012, 4 pages.

Erg-1/2/3 antibody (C-20)', Santa Cruz Biotechnology, Inc., accessed online Sep. 19, 2012 <URL:http://www.scbt.com/datasheet-353-erg-1-2-3-c-20-antibody.html>.

European Patent Office Communication Pursuant to Article 94(3) EPC from European Patent Application No. 05 779 973.6 dated Feb. 11, 2011, 7 Pages.

European Patent Office Communication Pursuant to Rule 114(2) EPC dated Oct. 24, 2012, reporting Third Party Observations in European Patent Application No. 05779973.6, 9 Pages.

European Patent Office Communication Pursuant to Article 94(3) EPC from European Patent Application No. 05 779 973.6 dated Jul. 2, 2012, 7 Pages.

European Patent Office Communication, European Search Report from European Patent Application No. 11172817.6 dated Sep. 30, 2011, 12 Pages.

European Patent Office Communication Pursuant to Rule 114(2) EPC dated Feb. 28, 2013, reporting Third Party Observations in European Patent Application No. 05779973.6, 9 Pages.

Communication dated Mar. 12, 2014 from European Patent Application No. 11172817.6, pp. 1-11.

Mohamed et al., Ets Family Protein, Erg Expression in Developing and Adult Mouse Tissues by a Highly Specific Monoclonal Antibody, Journal of Cancer, 1:197-208 (2010).

Rosen, Philip et al., Clinical Potential of the ERG Oncoprotein in Prostate Cancer, 9:131-137 (2012).

(56) References Cited

OTHER PUBLICATIONS

Santa Cruz product description of sc-353 printed from Santa Cruz Biotechnology website in Jan. 2014.
Non-Final Office Action dated Jan. 30, 2015 from U.S. Appl. No. 13/756,028, filed Jan. 31, 2013, 7 Pages.
Non-Final Office Action dated Feb. 9, 2015 from U.S. Appl. No. 11/579,695, filed Oct. 9, 2008, 17 Pages.
European Patent Office Communication dated Mar. 12, 2014 from European Patent Application No. 11172817.6, 11 Pages.
De Kok, Jacques B. et al. DD3(PCA3), a Very Sensitive and Specific Marker to Detect Prostate Tumors. Cancer Research, May 1, 2002, vol. 62, pp. 2695-2698.
Non-Final Office Action dated Aug. 30, 2013 from U.S. Appl. No. 13/445,706, filed Apr. 12, 2012, 13 Pages.
Dhanasekaran, Saravana M. et al. Delineation of prognostic biomarkers in prostate cancer. Nature, Aug. 23, 2001, vol. 412, pp. 822-826 with supplementary information available at www.nature.com.
Luo, Jun et al. α-Methylcayl-CoA Racemase: A New Molecular Marker for Prostate Cancer. Cancer Research, Apr. 15, 2002, vol. 62, pp. 2220-2226.
Wang, Shunyou et al. Prostate-specific deletion of the murine Pten tumor suppressor gene leads to metastatic prostate cancer. Cancer Cell, Sep. 2003, vol. 4, pp. 209-221.
Reddy, E. S. et al. Human erg protein (ets-related gene) mRNA, complete cds. GenBank Locus HUMERG11, Apr. 27, 1993, pp. 1-2, www.ncbi.nih.gov.
European Patent Office Communication dated Aug. 6, 2013 from European Patent Application No. 05 779 9736, pp. 1-7.
Third Party Observations dated Oct. 24, 2012 from European Patent Application No. 05 779 9736, pp. 1-9.
European Patent Office Communication dated Jul. 2, 2012 from European Patent Application No. 05 779 9736, pp. 1-7.
Third Party Observations dated Feb. 28, 2013 from European Patent Application No. 05 779 9736, pp. 1-6.
Hollenhorst, Peter C. et al. Genomic and Biochemical Insights into the Specificity of ETS Transcription Factors. Annual Review of Biochemistry, May 3, 2011, pp. 437-471.
Details for HG-U95E:91858_AT (2009), from www.affymetrix.com, Printed pp. 1-3.
Details for HG-U133A:211626_X_AT (2009), from www.affymetrix.com, Printed pp. 1-3.
GenBank Locus HUMERG11 (Apr. 11, 1993) "Human erg protein (ets-related gene) mRNA, complete cds" from www.ncbi.nlm.nin.gov, pp. 1-3.
Communication dated Jan. 9, 2014 from Canadian Patent Application No. 2,565,450, pp. 1-5.
Schalken, Jack A. et al. New targets for therapy in prostate cancer: different display code 3 (DD3(PCA3)), a highly prostate cancer-specific gene. Urology, Nov. 2003, vol. 62 (Supplement 5A), pp. 34-43.
DePrimo, Samuel E, et al. Expression profiling of blood samples from an SU5416 Phase III metastatic colorectal cancer clinical trial: a novel strategy for biomarker identification. BMC Cancer. Feb. 7, 2003, 3:3, pp. 1-12.
Shing, Danielle C. et al. FUS/ERG Gene Fusions in Ewing's Tumors. Cancer Research, Aug. 1, 2003, vol. 63, pp. 4568-4576.

* cited by examiner

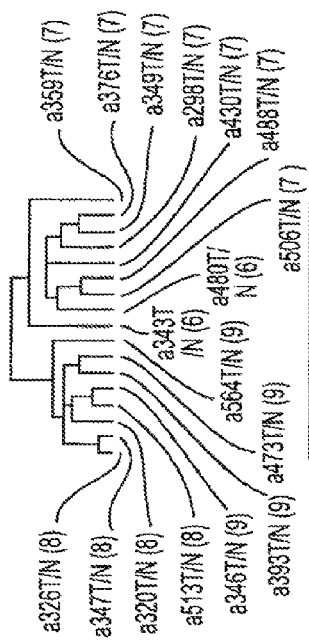
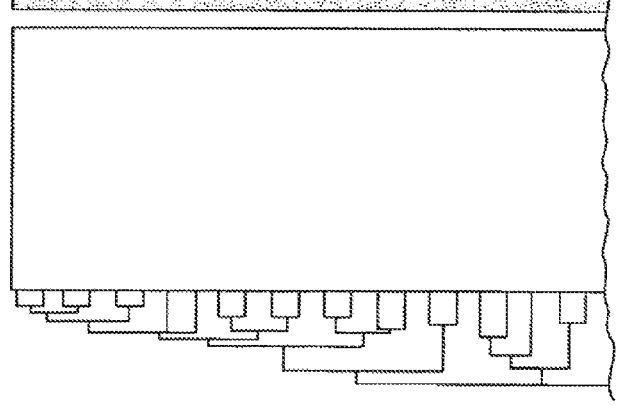
FIG. 3B

| CONTINUED FROM FIG. 3B | CONTINUED FROM FIG. 3B | CONTINUED FROM FIG. 3B |
|---|---|---|
| AK023938 | IPW | 2q37.3 |
| AI867102 | EST | 3 |
| NM_004522 | KIAA090 | 2q23.3 |
| J03198 | 6 | 1p13 |
| NM_012192 | KINN | 11p15.5-p15.3 |
| NM_005479 | GNAI3 | 10q23.33 |
| AA735522 | TIM9B | 3 |
| NM_025087 | FRAT1 | 4 |
| NM_015895 | KIAA008 | 6p22.2 |
| NM_018490 | 9 | 11p14-p13 |
| NM_021964 | FLJ2151 | 3q21 |
| NM_013387 | 1 | 22 |
| NM_018010 | LOC5105 | 3q13.13 |
| NM_004905 | 3 | 1q24.1 |
| NM_003031 | LGR4 | 16q12 |
| NM_016021 | ZNF148 | 6 |
| BC04399 | HSPC051 | 1p32.3 |
| NM_012245 | HIPPI | 14q24.3 |
| NM_018439 | AQP2 | 18 |
| NM_000016 | SIAH1 | 1p31 |
| D87445 | NCUBE1 | 15 |
| NM_024834 | DEME-6 | 10q26.13 |
| NM_015545 | SKIP | 7q22.1 |
| BC003682 | IMPACT | 1p36.1 |
| BC006629 | ACADM | 2q21.2 |
| NM_021795 | KIAA025 | 1q32 |
| NM_014959 | 6 | 19q13.33 |
| BF979419 | | 19q13.33 |
| NM_014454 | | 6q21 |
| AA923354 | | Xp11.4-p11.3 |

*FIG. 3B CONT.*

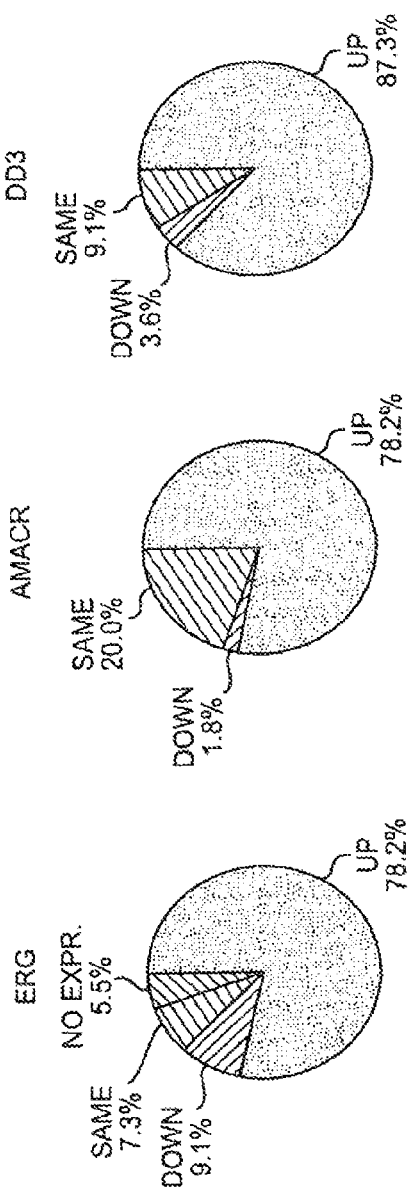
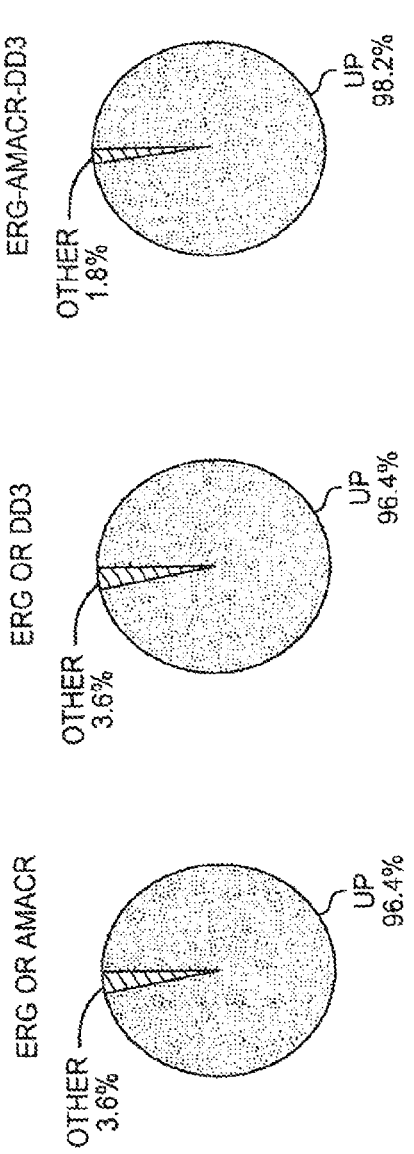

METHODS OF DIAGNOSING OR TREATING PROSTATE CANCER USING THE ERG GENE, ALONE OR IN COMBINATION WITH OTHER OVER OR UNDER EXPRESSED GENES IN PROSTATE CANCER

CROSS REFERENCE TO RELATED APPLICATIONS

The present application is a divisional of U.S. patent application Ser. No. 11/579,695, which is a national phase application of PCT/US2005/015926, filed May 6, 2005, and claims the benefit of U.S. provisional applications No. 60/568,822, filed May 7, 2004, and No. 60/622,021, filed Oct. 27, 2004, the entire disclosures of which are relied upon and incorporated by reference.

GOVERNMENT INTEREST

This invention was made with government support under grant numbers DK065977 and CA162383 awarded by the National Institutes of Health. The government has certain rights in the invention.

FIELD OF THE INVENTION

The present invention relates to oncogenes, tumor suppressor genes, as well as other genes, and their expression products, involved in prostate cancer, as well as derivatives and analogs thereof. The invention further relates to therapeutic compositions and methods of detecting, diagnosing, and treating cancer, including prostate and other related cancers.

BACKGROUND OF THE INVENTION

Prostate cancer (CaP) is the most common malignancy in American men and second leading cause of cancer mortality (Landis et al. (1999) Cancer J. Clin., 49:8-31; Jemal et al. (2004) Cancer J Clin 54:8-29). The molecular determinants in the development and progression of this disease are poorly understood. In recent years, there have been intensive investigations of molecular genetics of the CaP. To date, however, oncogene, tumor suppressor gene, or other gene alterations common to most CaPs have not been found. Alterations of tumor suppressors such as p53, PTEN and p27, or oncogenes such as BCL2, HER2 and C-MYC associate with only small subsets of primary CaP, with more frequent association observed in advanced CaP.

Current clinical parameters, including serum Prostate Specific Antigen (PSA), tumor stage, and Gleason score are routinely used as risk factors at the time of diagnosis, but have limited application to identify patients at a greater risk for developing aggressive CaP. Approximately 30-40% of patients treated with radical prostatectomy for localized CaP have been found to have microscopic disease that is not organ-confined and a significant portion of these patients relapse. (Singh et al., Cancer Cell (2000) 1:203-209; Henshell et at., Can. Res. (2003) 63: 4196-4203). Therefore, discovery of novel biomarkers or gene expression patterns defining CaP onset and progression is crucial in predicting patients with greater risk to develop aggressive CaP.

CaP-specific genetic alterations have been the subject of intensive research by several investigations in the past five years (Srikatan et al., In Prostate Cancer, Diagnosis and Surgical Treatment (2002) Springer-Verlag, 25-40; Karan et al., Int. J. Can. (2003) 103:285-293; Augustus et al., In Molecular Pathology of Early Cancer (1999) IOS press: 321-340; Moul et al., Clin Prostate Cancer (2002) 1:42-50; Lalani et al., Cancer and Mets Rev (1997) 16: 29-66; Issacs et al., Epidemiol Rev (2001) 23:36-41; Ozen et al., Anticancer Res (2000) 20:1905-1912; Morton et al., J Natl Med Assoc (1998) 90:S728-731). Promising leads both in biology and translational research areas are beginning to emerge from recent genomics and proteomics technology, as well as traditional approaches. However, the inherent heterogeneity of CaP has hampered the molecular characterization of CaP.

One of the challenges in studying molecular alterations in human cancers, including prostate tumors, is to define the relative contributions of genetic alterations in epithelial and non-epithelial components of the target organ in the process of tumorigeneis. Despite advances in technology, changes in human CaP-specific epithelial and stromal cell-associated gene expression are still not well understood.

Despite recent advances in the identification of molecular alterations associated with certain prostate cancers, the heterogeneous nature of prostate tissue has hindered the identification of genetic targets common to all, or at least the vast majority of, prostate cancers. The complexity and heterogeneity of prostate cancer has also hindered the identification of targets that allow differentiation between clinically aggressive and non-aggressive cancers at the time of diagnosis. Therefore, there remains a need to identify molecular alterations specific for a pathologically defined cell population that can provide important clues for optimal diagnosis and prognosis, and help to establish individualized treatments tailored to the molecular profile of the tumor.

Citation of references herein shall not be construed as an admission that such references are prior art to the present invention.

SUMMARY OF THE INVENTION

It is one of the objects of the present invention to provide methods and kits for detecting cancer, in particular prostate cancer. These methods and kits can be used to detect (either qualitatively or quantitatively) nucleic acids or proteins that serve as cancer markers. For example, the expression of the prostate cancer-cell-specific gene ERG, when detected in a biological sample from a subject, either alone or in combination with other cancer markers, including the expression of other prostate cancer-cell-specific genes, can be used to indicate the presence of prostate cancer in the subject or a higher predisposition of the subject to develop prostate cancer. Detecting ERG expression, alone or in combination with the expression of any gene identified in Tables 1-6, can thus be used to diagnose or prognose cancer, particularly prostate cancer.

According to one aspect of the invention, the method for detecting the expression of one or more prostate cancer cell-specific genes, such as ERG, AMACR, and LTF or the DD3 gene, in a biological sample, comprises:

(a) combining a biological sample with at least a first and a second oligonucleotide primer under hybridizing conditions, wherein the first oligonucleotide primer contains a sequence that hybridizes to a first sequence in a target sequence from a prostate cancer cell-specific gene, such as ERG (SEQ ID NO:1), AMACR (SEQ ID NO:3), and/or LTF (SEQ ID NO:5) and/or DD3 (SEQ ID NO:4), and the second oligonucleotide primer contains a sequence that hybridizes to a second sequence in a nucleic acid strand complementary to the target sequence, wherein the first sequence does not overlap with the second sequence, (b) adding at least one polymerase activity to produce a plurality of amplification products when the target sequence is present in the biological sample, (c) adding an oligonucleotide probe that hybridizes to at least one amplification product of the target sequence, and (d) detecting whether a signal results from hybridization between the oligonucleotide probe and the at least one amplification product, wherein detection of the signal indicates the expression of a prostate cancer cell-specific gene in the biological sample.

The method preferably comprises detecting the expression of the following combinations of genes: 1) ERG and AMACR; 2) ERG and DD3; and 3) ERG, AMACR and DD3. In another embodiment, the method comprises detecting LTF and one or more of ERG, AMACR and DD3. Expression of these genes can also be detected by measuring ERG, AMACR or LTF polypeptides in the biological sample.

The biological sample is preferably a prostate tissue, blood, or urine sample. Detecting a signal resulting from hybridization between the oligonucleotide probe and the at least one amplification product can be used to diagnose or prognose cancer, particularly prostate cancer.

The oligonucleotide probe may be optionally fixed to a solid support. When detecting ERG expression in a biological sample, the oligonucleotide probe, first oligonucleotide primer, and second oligonucleotide primer, each comprise a nucleic acid sequence that is capable of hybridizing under defined conditions (preferably under high stringency hybridization conditions, e.g., hybridization for 48 hours at 65° C. in 6×SSC followed by a wash in 0.1×SSX at 50° C. for 45 minutes) to SEQ ID NO:1. Thus, the oligonucleotide probe, first oligonucleotide primer, and second oligonucleotide primer can include, for example, SEQ ID NO:1 itself, or a fragment thereof or a sequence complementary thereto. Preferably the oligonucleotide probe, first oligonucleotide primer, or second oligonucleotide primer is a fragment of SEQ ID NO:1 having at least about 15, at least about 20, or at least about 50 contiguous nucleotides of SEQ ID NO:1 or a sequence complementary thereto. When detecting ERG expression, the target sequence is preferably a fragment of SEQ ID NO:1. Probes, primers, and target sequences can be similarly derived from other genes of interest, such as DD3 (SEQ ID NO:4), and other prostate cancer-cell-specific genes, including, for example, AMACR (SEQ ID NO:3) and LTF (SEQ ID NO:5).

In another aspect of the invention, the method of diagnosing or prognosing prostate cancer comprises:

measuring the expression level (e.g. mRNA or polypeptide) of an over expressed prostate cancer cell-specific gene, such as ERG and/or AMACR, and/or the DD3 gene in a biological sample, and correlating the expression level of the ERG, AMACR, and/or DD3 gene with the presence of prostate cancer or a higher predispo-sition to develop prostate cancer in the subject.

In a related aspect of the invention, the method of diagnosing or prognosing prostate cancer comprises:

measuring the expression level (e.g. mRNA or polypeptide) of an under expressed prostate cancer cell-specific gene, such as LTF in a biological sample, and correlating the expression level of the LTF gene with the presence of prostate cancer or a higher predisposition to develop prostate cancer in the subject.

The skilled artisan will understand how to correlate expression levels or patterns of the desired genes with the presence of prostate cancer or a higher predisposition to develop prostate cancer. For example, the expression levels can be quantified such that increased or decreased expression levels relative to a control sample or other standardized value or numerical range indicate the presence of prostate cancer or a higher predisposition to develop prostate cancer.

The increased or decreased expression levels in the methods of the invention may be measured relative to the expression level of the prostate cancer cell-specific gene or polypeptide in normal, matched tissue, such as benign prostate epithelial cells from the same subject. Alternatively, the expression level of a gene or polypeptide may be measured relative to the expression of the gene or polypeptide in other noncancerous samples from the subject or in samples obtained from a different subject without cancer. Expression of a gene may also be normalized by comparing it to the expression of other cancer-specific markers. For example, in prostate cancer, a prostate-cell specific marker, such as PSA, can be used as a control to compare and/or normalize expression levels of other genes, such as ERG, LTF, DD3, and/or AMACR. By way of example, the method of diagnosing or prognosing prostate cancer comprises measuring the expression levels of the ERG, DD3 and/or AMACR gene and diagnosing or prognosing prostate cancer, where an increased expression level of the ERG, DD3, and/or AMACR gene of at least two times as compared to the control sample indicates the presence of prostate cancer or a higher predisposition in the subject to develop prostate cancer. Conversely, by way of example, in such a method of diagnosing or prognosing prostate cancer, a decreased expression of the LTF gene of at least two times as compared to the control sample indicates the presence of prostate cancer or a higher predisposition in the subject to develop prostate cancer.

The expression levels of prostate cancer cell-specific genes (e.g., mRNA or polypeptide expression) can be detected according to the methods described herein or using any other known detection methods, including, without limitation, immunohistochemistry, Southern blotting, Northern blotting, Western blotting, ELISA, and nucleic acid amplification procedures, including but not limited to PCR, transcription-mediated amplification (TMA), nucleic acid sequence-based amplification (NASBA), self-sustained sequence replication (3SR), ligase chain reaction (LCR), strand displacement amplification (SDA), and Loop-Mediated Isothermal Amplification (LAMP).

It is yet another object of the present invention to provide a method of determining a gene expression pattern in a biological sample, where the pattern can be correlated with the presence or absence of tumor cells, particularly prostate tumor cells. For example, ERG is detected in combination with other prostate cancer cell-specific genes (identified in Tables 1-6), including AMACR and/or LTF, to obtain expression profiles from biological samples. The expression profiles of these prostate cancer-cell-specific genes are useful for detecing cancer, particularly prostate cancer. ERG can also be detected in combination with DD3, with or without other prostate cancer cell-specific genes, such as AMACR and/or LTF, to obtain expression profiles from biological samples. These expression profiles are also useful for detecting cancer, particularly prostate cancer. Increased levels of ERG, AMACR, and/or DD3 in a biological sample indicate the presence of prostate cancer or a higher predisposition in the subject to develop prostate cancer. Decreased levels of LTF in a biological sample indicate the presence of prostate cancer or a higher predisposition in the subject to develop prostate cancer.

It is yet another object of the present invention to provide a method of determining a gene expression pattern in a biological sample, where the pattern can be used to indicate or predict the pathologic stage of cancer, particularly prostate cancer. For example, the gene expression pattern can be used to indicate or predict a moderate risk prostate cancer or a high risk prostate cancer or to predict whether the prostate cancer is progressing or regressing or in remission. The gene expression pattern can also be used as a prognostic indictor of disease-free survival following radical prostatectomy. In a particular embodiment, gene expression patterns are derived from the expression level of the ERG gene, alone or in combination with other prostate cancer-cell-specific genes (identified in Tables 1-6), including AMACR and LTF, or DD3.

Kits for detecting cancer, particularly prostate cancer, are also provided. These kits comprise a nucleic acid probe, such as the ones described herein, that hybridizes to a prostate cancer-cell-specific gene. In one embodiment the nucleic acid probe hybridizes to SEQ ID NO:1 (ERG) or the complement thereof under defined hybridization conditions (preferably under high stringency hybridization conditions, e.g., hybridization for 48 hours at 65° C. in 6×SSC followed by a wash in 0.1×SSX at 50° C. for 45 minutes) and includes SEQ ID NO:1, itself, or a fragment of SEQ ID NO:1 having at least about 15, at least about 20, or at least about 50 contiguous nucleotides of SEQ ID NO:1 or a sequence complementary thereto. In a particular embodiment, the probe selectively hybridizes to the ERG1 and ERG2 isoforms but not to ERG isoforms 3-9. In another embodiment, the probe selectively hybridizes to the ERG1 isoform but not to ERG isoforms 2-9. The nucleic acid probe may be optionally fixed to a solid support.

The kit may also contain at least one additional nucleic acid probe that hybridizes (preferably high stringency hybridization conditions, e.g., hybridization for 48 hours at 65° C. in 6×SSC followed by a wash in 0.1×SSX at 50° C. for 45 minutes) to DD3 (SEQ ID NO:4) or a gene identified in Tables 1-6, including for example, AMACR (SEQ ID NO:3) or LTF (SEQ ID NO:5). In one embodiment, the kit comprises a first oligonucloetide probe capable of hybridizing to SEQ ID NO:1 (ERG) or a sequence complimentary thereto under conditions of high stringency and at least one other oligonucleotide probe capable of hybridizing to SEQ ID NO:3 (AMACR) or a sequence complimentary thereto, or to SEQ ID NO:4 (DD3) or a sequence complementary thereto, or to a gene identified in Tables 1-6 under conditions of high stringency. In a related embodiment, the kit having an ERG and AMACR probe further comprises a third oligonucleotide probe capable of hybridzing to SEQ ID NO:4 (DD3) or a sequence complementary thereto. The kits described herein may optionally contain an oligonucleotide probe capable of hybridizing to SEQ ID NO:5 (LTF) or a sequence complementary thereto under conditions of high stringency.

The kits may further comprise a first oligonucleotide primer and a second oligonucleotide primer, where the first oligonucleotide primer contains a sequence that hybridizes to a first sequence in SEQ ID NO:1, and the second oligonucleotide primer contains a sequence that hybridizes to a second sequence in a nucleic acid strand complementary to SEQ ID NO:1, wherein the first sequence does not overlap with the second sequence. The first and second oligonucleotide primers are capable of amplifying a target sequence of interest in SEQ ID NO:1. Similarly, the kits can further comprise first and second oligonucleotide primers derived from DD3 (SEQ ID NO:4) or a prostate cancer-cell-specific gene, including, for example AMACR (SEQ ID NO:3) or LTF (SEQ ID NO:5).

It is another object of the invention to provide therapeutic methods of treating cancer, in particular prostate cancer.

It is yet another object of the present invention to provide screening methods for identifying compounds that modulate expression of a CaP-cell-specific gene, such as ERG, in prostate cancer cells.

The present invention is based in part on the identification of gene expression signatures that correlate with a high risk of CaP progression. Over expression or under expression of specific genes are predictive of tumor progression. The invention provides genes, such as the ERG gene, and analogs of specific genes that can be used alone or in combination with DD3 or other CaP-cell-specific genes, such as AMACR or LTF, to function as diagnostic and prognostic targets for cancer, particularly prostate tumors. The invention further provides genes, such as the ERG gene, and analogs of specific genes that can be used alone or in combination as therapeutic targets for cancer, in particular prostate tumors.

The invention further discloses diagnostic kits comprised of an anti-CaP-cell-specific gene antibody, for example, an anti-ERG gene antibody, which is optionally, detectably labeled. A kit is also provided that comprises nucleic acid primer sequences and/or a nucleic acid probe capable of hybridizing under defined conditions (preferably high stringency hybridization conditions, e.g., hybridization for 48 hours at 65° C. in 6×SSC followed by a wash in 0.1×SSX at 50° C. for 45 minutes) to an ERG nucleic acid. The kits may also contain an anti-DD3 gene antibody or a second anti-CaP-cell-specific gene antibody, such as an anti-AMACR or anti-LTF gene antibody, or a second set of nucleic acid primer sequences and/or a nucleic acid probe capable of hybridizing under defined conditions to the DD3 gene or another CaP-cell-specific gene, such as the AMACR or LTF gene.

The disclosed CaP-cell-specific genes, such as ERG, can be used alone or in combination as biomarkers of cancer, and in particular, prostate cancers and other related diseases, as targets for therapeutic intervention, or as gene therapy agents.

The invention provides for treatment of disorders of hyperproliferation (e.g., cancer, benign tumors) by administering compounds that modulate expression of the specific genes.

Methods of screening cancer cells, and in particular, prostate cancer cells, for specific gene expression signatures, including ERG gene expression signatures, alone or in combination with DD3 gene expression signatures or other CaP-cell-specific gene expression signatures, such as AMACR or LTF, are provided.

Additional objects of the invention will be set forth in part in the description following, and in part will be understood from the description, or may be learned by practice of the invention.

It is to be understood that both the foregoing general description and the following detailed description are exemplary and explanatory only and are not restrictive of the invention as claimed.

X-axis: CaP patients analyzed (1-20); Y-axis: Expression ratio between tumor versus benign laser capture microdissection (LCM) sample pairs.

FIG. 2: Identification of genes by a distance based MDS and weighted analysis that discriminates between cancerous and benign tissue. (A) Two-dimensional MDS plot elucidating discrimination of 18 tumor samples and 18 benign samples. (B) Hierarchical clustering dendrogram with two major clusters of 18 tumor samples in the right cluster and 18 benign samples in the left cluster.

FIG. 3: A distance based MDS and weighted gene analysis using the tumor over benign ratio (or fold change) data for the identification of genes that can discriminate between high risk CaP and moderate risk CaP. (A) A supervised MDS analysis of 18 samples (9 samples from high risk group and 9 samples from moderate risk group) that ranks the genes according to their impact on minimizing cluster volume and maximizing center-to-center inter cluster distance. (B) Hierarchical clustering of the first 55 genes of the top 200 obtained by the MDS analysis. Genes and samples are arranged as ordered by cluster and treeview. Expression of each gene in each sample is obtained by the tumor over benign ratio or fold change (T/N). Dendrogram at the top of the cluster shows two major clusters, 9 samples of the MR groups in the right cluster and 9 samples of the HR groups in the left cluster. (C) Two-dimensional MDS plot of 18 CaP tumor epithelia that shows the differentiation between the high risk group (9 tumor epithelia) and moderate risk group (9 tumor epithelia) on the basis of the impact of the rank of the genes that discriminate between the HR and MR groups. (D) Hierarchical clustering dendrogram with two major clusters of 9 samples of the MR groups in the left cluster and 8+1 samples of the HR groups in the right cluster. (E) Two-dimensional MDS plot of 18 CaP benign epithelia that shows the discrimination between the high risk group (9 benign epithelia) and moderate risk group (9 benign epithelia) samples.

Figure 4A:
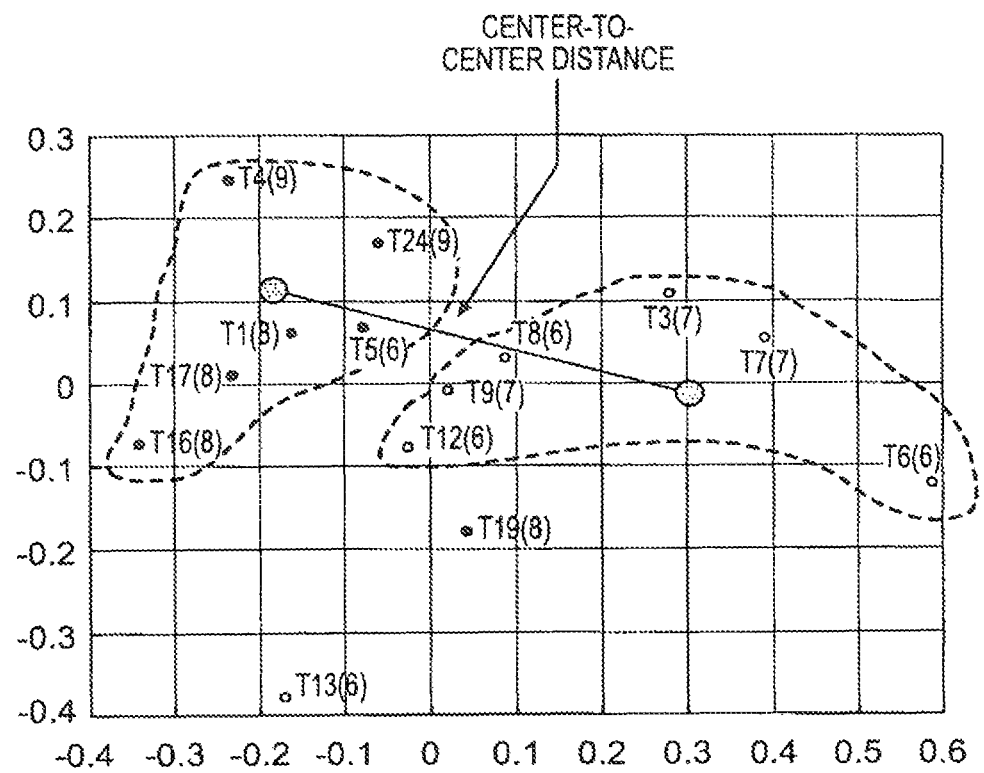
Figure 4B:
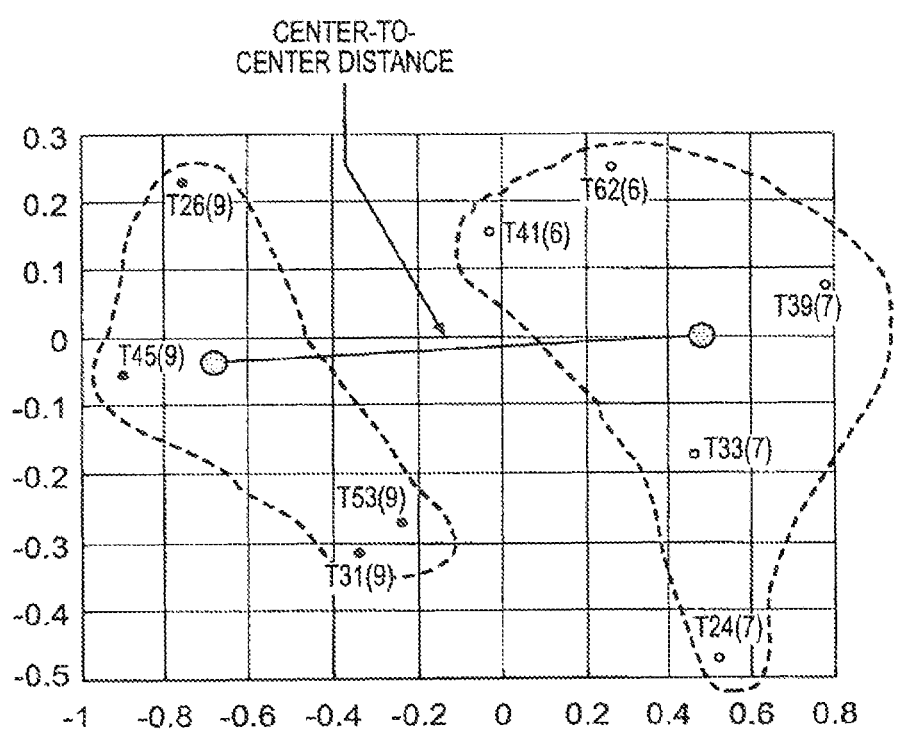

FIG. 4: In silico validation: the discriminatory potential of the genes that we obtained from our supervised MDS analysis on two independent data sets (Welsh et al. 2001, Singh et al. 2002). Two-dimensional MDS plot that shows the discrimination between 7 tumor epithelia of the high risk group and 7 tumor epithelia of the moderate risk group using data from Welsh et al. (A), as well as discrimination between 4 tumor epithelia of the high risk group and 5 tumor epithelia of the moderate risk group using data from Singh et al. (B).

FIG. 5: Combined gene expression analysis of ERG, AMACR and DD3 in tumor and benign prostate epithelial cells of 55 CaP patients. The graphs represent patient distribution by tumor versus benign gene expression ratios according to five gene expression categories: 1) "Up:" greater than 2 fold over expression in tumor compared to benign; 2) "Down:" less than 0.5 fold under expression in tumor compared to benign; 3) "Same:" no significant difference (0.5 to 2 fold); 4) "No expr.:" no detectable gene expression; and 5) "Other:" collectively defines patients with expression category 2, 3 and 4 for the indicated genes (i.e., other than category 1). (A) ERG Expression. (B) AMACR Expression. (C) DD3 Expression. (D) ERG or AMACR Expression. (E) ERG or DD3 Expression. (F) ERG, AMACR, or DD3 Expression.

Figure 6:
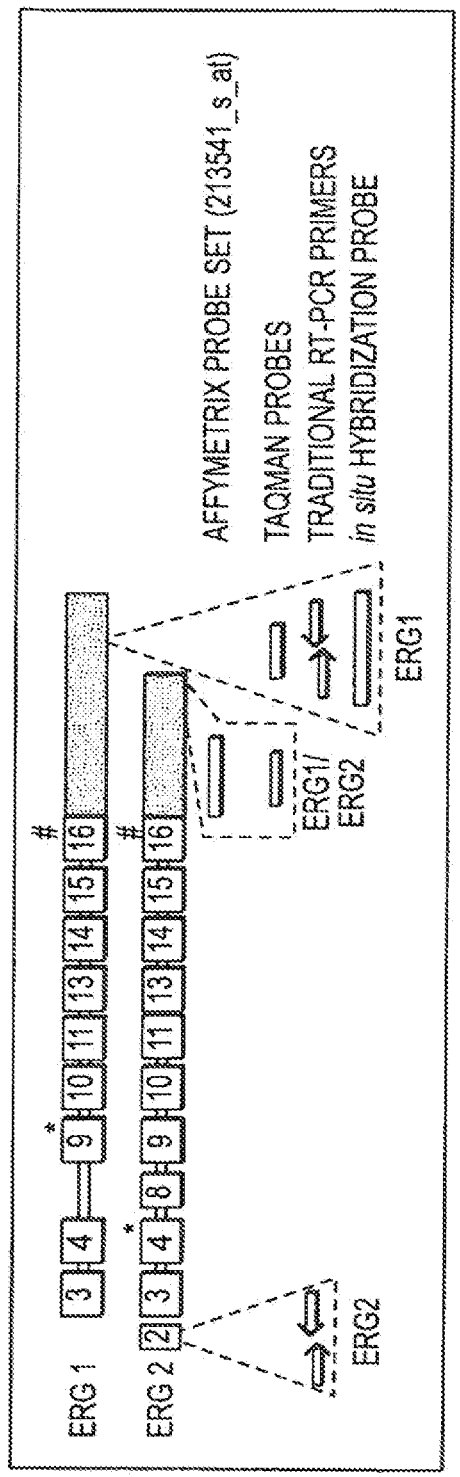

FIG. 6: Map of ERG1 and ERG2 isoforms with probe and primer locations. The numbered boxes represent exons, the darker boxes after exon 16 are the 3' non-coding exon regions. Translational start and stop codons are indicated by star and pound signs, respectively. The locations of the Affymetrix probe set (213541_s_at), the TaqMan probes, the traditional RT-PCR primers, and the in situ hybridization probe are indicated.

Figure 7:
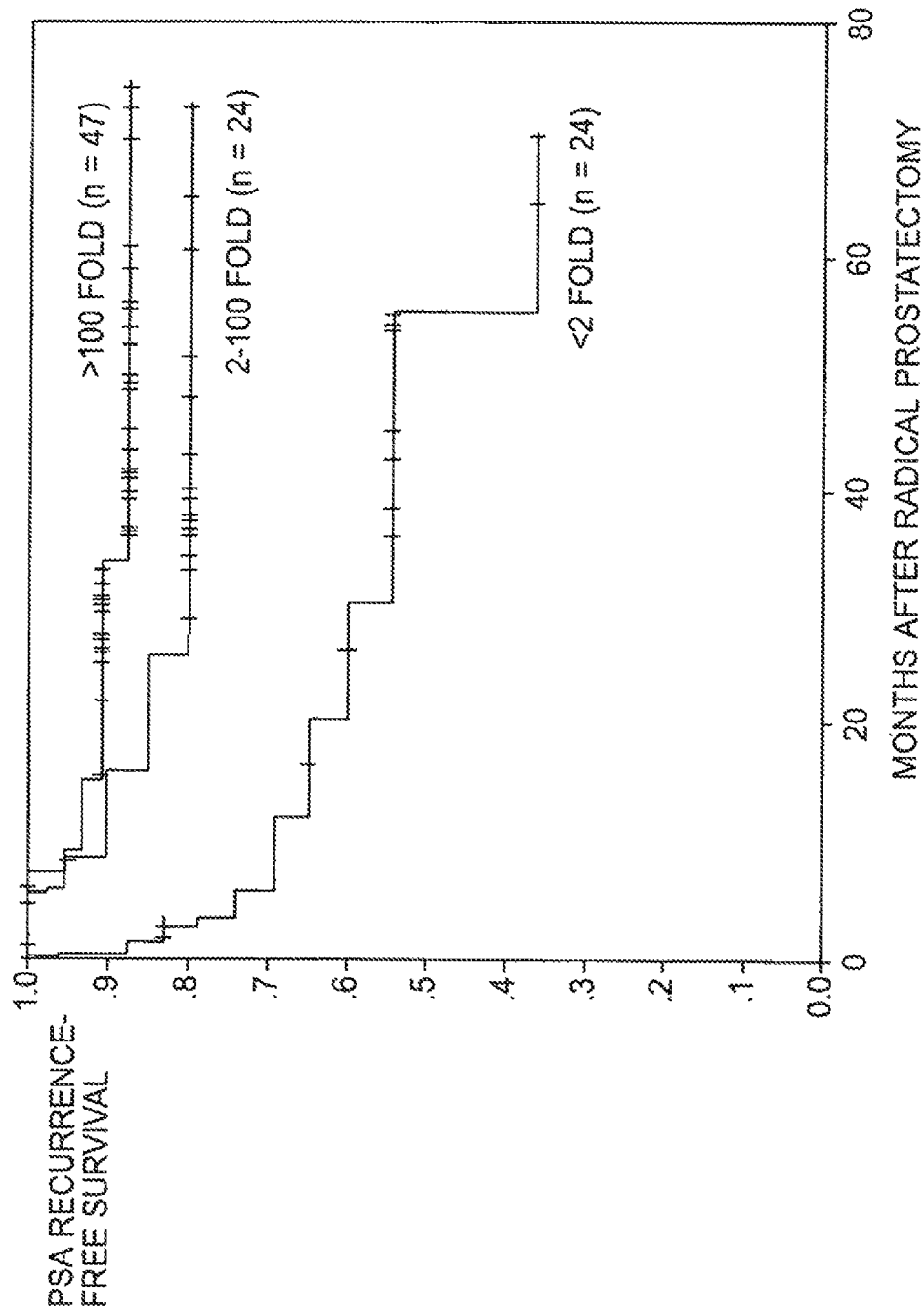

FIG. 7: Correlation of ERG1 expression and PSA recurrence-free survival. Kaplan-Meier analysis of correlation with post-prostatectomy PSA recurrence-free survival was performed on 95 CaP patients having detectable levels of ERG1 mRNA by real time QRT-PCR (TaqMan). Kaplan-Meier survival curves were stratified by the following ERG1 expression categories: 1) greater than 100 fold over expression; 2) 2-100 fold over expression; and 3) less than 2 fold over expression or under expression of ERG1 in the prostate tumor cells. The p value was 0.0006.

Figure 8:
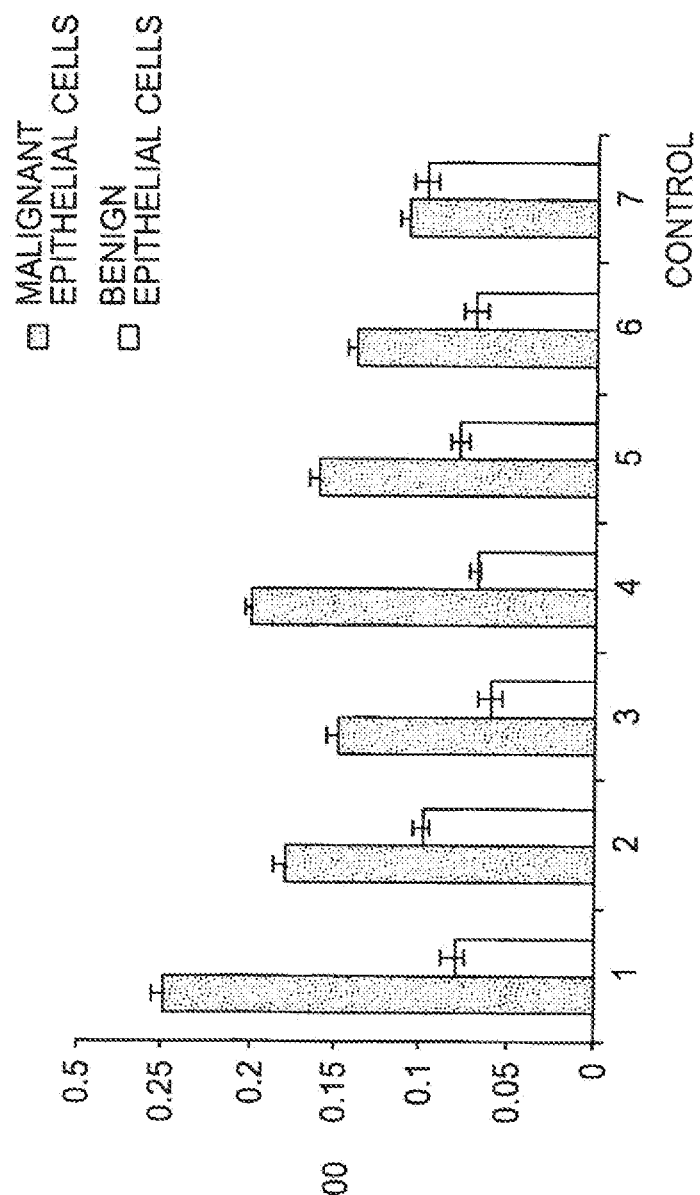

FIG. 8. In situ hybridization images in 7 CaP patients were analysed by the Open-Lab image analysis software (Improvisation, Lexington, Mass.) coupled to a microscope via a cooled digital camera (Leica Microsystems, Heidelburg, Germany). Density (OD) values for tumor (dark columns) and benign (light columns) epithelium are shown on the Y axis, and patients 1-7 are shown in the X axis. Patient No. 7 was added as a control with no significant ERG1 expression difference between tumor and benign cells by QRT-PCR (TaqMan). Statistical analysis was performed with the SPSS software package.

Figure 9:
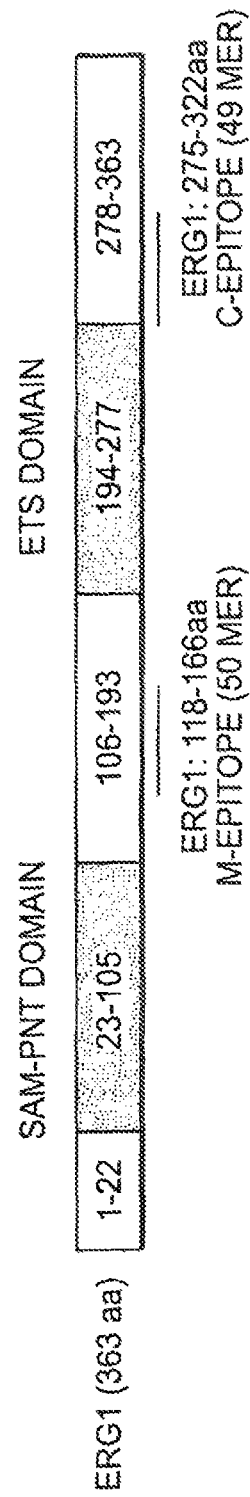

FIG. 9. ERG1 is represented as a modular structure. The two conserved regions namely SAM-PNT Domain (Protein/RNA interaction domain) and ETS Domain (Interaction with DNA) are shaded.

DETAILED DESCRIPTION OF THE INVENTION

Definitions

The term "CaP-cell-specific gene," or "prostate cancer-cell-specific gene," refers to a gene identified in Tables 1-6. The definition further encompasses CaP-cell-specific gene analogs, e.g., orthologues and homologues, and functionally equivalent fragments of CaP-cell-specific genes or their analogs, the expression of which is either upregulated or downregulated in prostate cancer cells.

The term "CaP-cell-specific gene expression signature" refers to the pattern of upregulation or downregulation of product expression as measured by the Affymetrix GeneChip assay described in Example 1, the QRT-PCR assay described in Example 2, or any other quantitative expression assay known in the art.

The term "ERG" refers to the ERG gene or ERG cDNA or mRNA described herein, and includes ERG isoforms, such as ERG1 and ERG2. The cDNA sequence of the ERG1 gene is published in GenBank under the accession number M21535. The cDNA sequence of the ERG2 gene is published in GenBank under the accession number M17254.

The term "AMACR" refers to the AMACR gene or AMACR cDNA or mRNA described herein, and includes AMACR isoforms. The cDNA sequence of the AMACR gene is published in GenBank under the accession number NM_014324.

The term "DD3" refers to the DD3 gene or DD3 cDNA or mRNA described herein, and includes DD3 isoforms. The cDNA sequence of the DD3 gene is published in GenBank under the accession number AF 103907 and is also disclosed in WO 98/45420 (1998). Although DD3 was originally used to describe a fragment of exon 4 of the prostate cancer antigen 3 (PCA3) gene, the term, as used in herein, is not so limited. DD3 is intended to refer to the entire DD3 gene or cDNA or mRNA, which in the art is also commonly referred to as PCA3.

The term "LTF" refers to the LTF gene or LTF cDNA or mRNA described herein and includes LTF isoforms. The cDNA sequence of the LTF gene is published in GenBank under the accession number NM_002343.

The term "polypeptide" is used interchangeably with the terms "peptide" and "protein" and refers to any chain of amino acids, regardless of length or posttranslational modification (e.g., glycosylation or phosphorylation), or source (e.g., species).

The phrase "substantially identical," or "substantially as set out," means that a relevant sequence is at least 70%, 75%, 80%, 85%, 90%, 95%, 97, 98, or 99% identical to a given sequence. By way of example, such sequences may be allelic variants, sequences derived from various species, or they may be derived from the given sequence by truncation, deletion, amino acid substitution or addition. For polypeptides, the length of comparison sequences will generally be at least 20, 30, 50, 100 or more amino acids. For nucleic acids, the length of comparison sequences will generally be at least 50, 100, 150, 300, or more nucleotides. Percent identity between two sequences is determined by standard alignment algorithms such as, for example, Basic Local Alignment Tool (BLAST) described in Altschul et al. (1990) J. Mol. Biol., 215:403-410, the algorithm of Needleman et al. (1970) J. Mol. Biol., 48:444-453, or the algorithm of Meyers et al. (1988) Comput. Appl. Biosci., 4:11-17.

The terms "specific interaction," "specific binding," or the like, mean that two molecules form a complex that is relatively stable under physiologic conditions. The term is also applicable where, e.g., an antigen-binding domain is specific for a particular epitope, which is carried by a number of antigens, in which case the specific binding member carrying the antigen-binding domain will be able to bind to the various antigens carrying the epitope. Specific binding is characterized by a high affinity and a low to moderate capacity. Nonspecific binding usually has a low affinity with a moderate to high capacity. Typically, the binding is considered specific when the affinity constant $K_a$ is higher than $10^6 M^{-1}$, more preferably higher than $10^7 M^{-1}$, and most preferably $10^8 M^{-1}$. If necessary, non-specific binding can be reduced without substantially affecting specific binding by varying the binding conditions. Such conditions are known in the art, and a skilled artisan using routine techniques can select appropriate conditions. The conditions are usually defined in terms of concentration of antibodies, ionic strength of the solution, temperature, time allowed for binding, concentration of non-related molecules (e.g., serum albumin, milk casein), etc. The term "detectably labeled" refers to any means for marking and identifying the presence of a molecule, e.g., an oligonucleotide probe or primer, a gene or fragment thereof, or a cDNA molecule. Methods for labeling a molecule are well known in the art and include, without limitation, radioactive labeling (e.g., with an isotope such as $^{32}P$, $^{35}S$, or $^{125}I$) and nonradioactive labeling (e.g., fluorescent and chemiluminescent labeling).

The term "modulatory compound" is used interchangeably with the term "therapeutic" as used herein means any compound capable of "modulating" either CaP-cell-specific gene expression at the transcriptional, translational, or post-translational levels or modulating the biological activity of a CaP-cell-specific polypeptide. The term "modulate" and its cognates refer to the capability of a compound acting as either an agonist or an antagonist of a certain reaction or activity. The term modulate, therefore, encompasses the terms "activate" and "inhibit." The term "activate," for example, refers to an increase in the expression of the CaP-cell-specific gene or activity of a CaP-cell-specific polypeptide in the presence of a modulatory compound, relative to the activity of the gene or the polypeptide in the absence of the same compound. The increase in the expression level or the activity is preferably at least about 10%, 20%, 30%, 40%, 50%, 60%, 70%, 80%, 90%, or higher. Analogously, the term "inhibit" refers to a decrease in the expression of the CaP-cell-specific gene or activity of a CaP-cell-specific polypeptide in the presence of a modulatory compound, relative to the activity of the gene or the polypeptide in the absence of the same compound. The decrease in the expression level or the activity is preferably at least about 10%, 20%, 30%, 40%, 50%, 60%, 70%, 80%, 90%, or higher. The expression level of the CaP-cell-specific gene or activity of a CaP-cell-specific polypeptide can be measured as described herein or by techniques generally known in the art.

The term "treatment" is used interchangeably herein with the term "therapeutic method" and refers to both therapeutic treatment and prophylactic/preventative measures. Those in need of treatment may include individuals already having a particular medical disorder as well as those who may ultimately acquire the disorder.

The term "isolated" refers to a molecule that is substantially free of its natural environment. Any amount of that molecule elevated over the naturally occurring levels due to any manipulation, e.g., over expression, partial purification, etc., is encompassed with the definition. With regard to partially purified compositions only, the term refers to an isolated compound that is at least 50-70%, 70-90%, 90-95% (w/w), or more pure.

The term "effective dose," or "effective amount," refers to that amount of the compound that results in amelioration of symptoms in a patient or a desired biological outcome, e.g., inhibition of cell proliferation. The effective amount can be determined as described in the subsequent sections.

The terms "polynucleotide," "oligonucleotide," "nucleic acid," and "DNA" are used interchangeably herein and refer to deoxyribonucleic acid (DNA), and, where appropriate, ribonucleic acid (RNA). The term should also be understood to include nucleotide analogs, and single or double stranded polynucleotides. Examples of polynucleotides include, but are not limited to, plasmid DNA or fragments thereof, viral DNA or RNA, anti-sense RNA, etc. The term "plasmid DNA" refers to double stranded DNA that is circular.

As used herein the term "hybridization under defined conditions," or "hybridizing under defined conditions," is intended to describe conditions for hybridization and washes under which nucleotide sequences that are significantly identical or homologous to each other remain bound to each other. The conditions are such that sequences, which are at least about 6 and more preferably at least about 20, 50, 100, 150, 300, or more nucleotides long and at least about 70%, more preferably at least about 80%, even more preferably at least about 85-90% identical, remain bound to each other. The percent identity can be determined as described in Altschul et al. (1997) Nucleic Acids Res., 25: 3389-3402.

Appropriate hybridization conditions can be selected by those skilled in the art with minimal experimentation as exemplified in Ausubel et al. (2004), Current Protocols in Molecular Biology, John Wiley & Sons. Additionally, stringent conditions are described in Sambrook et al. (2001) Molecular Cloning: A Laboratory Manual, $3^{rd}$ ed., Cold Spring Harbor Laboratory Press. A nonlimiting example of defined conditions of low stringency is as follows. Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe is used. Filters are incubated in hybridization mixture for 18-20 hours at 40° C., and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Filters are blotted dry and exposed for autoradiography. Other conditions of low stringency well known in the art may be used (e.g., as employed for cross-species hybridizations).

A non-limiting example of defined conditions of high stringency is as follows. Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in the prehybridization mixture containing 100 µg/ml denatured salmon sperm DNA and 5-20×10$^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 minutes. Other conditions of high stringency well known in the art may be used. An oligonucleotide hybridizes specifically to a target sequence under high stringency conditions.

The term "solid support" means a material that is essentially insoluble under the solvent and temperature conditions of the assay method, comprising free chemical groups available for joining an oligonucleotide or nucleic acid. Preferably, the solid support is covalently coupled to an oligonucleotide designed to directly or indirectly bind a target nucleic acid. When the target nucleic acid is an mRNA, the oligonucleotide attached to the solid support is preferably a poly-T sequence. A preferred solid support is a particle, such as a micron- or submicron-sized bead or sphere. A variety of solid support materials are contemplated, such as, for example, silica, polyacrylate, polyacrylamide, a metal, polystyrene, latex, nitrocellulose, polypropylene, nylon or combinations thereof. More preferably, the solid support is capable of being attracted to a location by means of a magnetic field, such as a solid support having a magnetite core. Particularly preferred supports are monodisperse magnetic spheres (i.e., uniform size.+-.about 5%).

The term "detecting" or "detection" means any of a variety of methods for determining the presence of a nucleic acid, such as, for example, hybridizing a labeled probe to a portion of the nucleic acid. A labeled probe is an oligonucleotide that specifically binds to another sequence and contains a detectable group which may be, for example, a fluorescent moiety, a chemiluminescent moiety (such as an acridinium ester (AE) moiety that can be detected chemiluminescently under appropriate conditions (as described in U.S. Pat. No. 5,283,174)), a radioisotope, biotin, avidin, enzyme, enzyme substrate, or other reactive group. Other well know detection techniques include, for example, gel filtration, gel electrophoresis and visualization of the amplicons, and High Performance Liquid Chromatography (HPLC). As used throughout the specification, the term "detecting" or "detection" includes either qualitative or quantitative detection.

The term "primer" or "oligonculeotide primer" means an oligonucleotide capable of binding to a region of a target nucleic acid or its complement and promoting nucleic acid amplification of the target nucleic acid. Generally, a primer will have a free 3' end that can be extended by a nucleic acid polymerase. Primers also generally include a base sequence capable of hybridizing via complementary base interactions either directly with at least one strand of the target nucleic acid or with a strand that is complementary to the target sequence. A primer may comprise target-specific sequences and optionally other sequences that are non-complementary to the target sequence. These non-complementary sequences may comprise a promoter sequence or a restriction endonuclease recognition site.

CaP-Cell-Specific Gene Expression Signature Identification

The present invention is based in part on the identification and validation of consistent CaP epithelial cell specific gene expression signatures. These gene expression signatures define patients with CaP who are at risk to develop advanced disease by identifying genes and pathways in prostate epithelial cells that differentiate between aggressive and non-aggressive courses of cancer development. Two patient groups were selected, a high risk (HR) group having, for example, PSA recurrence, Gleason score 8-9, T3c stage, seminal vesicle invasion, poor tumor differentiation, and a moderate risk (MR) group having, for example, no PSA recurrence, Gleason score 6-7, T2a-T3b stage, no seminal vesicle invasion, well or moderate tumor differentiation. The two patient groups were matched for known risk factors: age, race, and family history of CaP. LCM derived epithelial cells from tumor and normal prostate of the two patient groups were compared by GeneChip analyses, as described in the following Example 1. Results were validated using quantitative reverse transcriptase PCR (QRT-PCR), as described in the following Example 2. The group of genes identified and validated as having the highest association with aggressive or non-aggressive CaP can be used to reliably determine the likely course of CaP progression.

Strikingly, one of the most consistently over expressed genes in CaP cells identified in this study was the ERG (ETS related gene) oncogene, a member of the ETS transcription factor family. (Oikawa et al., Gene (2003) 303:11-34; Sharrocks, A D, Nat Rev Mol Cell Biol (2001) 2(11):827-37; Hart et al., Oncogene (1995) 10(7):1423-30; Rao et al., Science (1987) 237(4815): 635-639). Two isoforms of ERG, ERG1 and ERG2, are over expressed with the highest frequency. The ERG1 coding sequence (with start and stop codons underlined) is publicly available through GenBank under the accession number M21535, as follows:

(SEQ ID NO: 1)
```
  1 gaattccctc caaagcaaga caaatgactc acagagaaaa aagatggcag aaccaagggc
 61 aactaaagcc gtcaggttct gaacagctgg tagatgggct ggcttactga aggacatgat
121 tcagactgtc ccggacccag cagctcatat caaggaactc tcctgatgaa tgcagtgtgg
181 ccaaaggcgg gaagatggtg ggcagcccag acaccgttgg gatgaactac ggcagctaca
```

-continued

```
 241 tggaggagaa gcacatgcca cccccaaaca tgaccacgaa cgagcgcaga gttatcgtgc 301 cagcagatcc tacgctatgg agtacagacc atgtgcggca gtggctggag tgggcggtga 361 aagaatatgg ccttccagac gtcaacatct tgttattcca gaacatcgat gggaaggaac 421 tgtgcaagat gaccaaggac gacttccaga ggctcacccc cagctacaac gccgacatcc 481 ttctctcaca tctccactac ctcagagaga ctcctcttcc acatttgact tcagatgatg 541 ttgataaagc cttacaaaac tctccacggt taatgcatgc tagaaacaca gatttaccat 601 atgagccccc caggagatca gcctggaccg gtcacggcca ccccacgccc cagtcgaaag 661 ctgctcaacc atctccttcc acagtgccca aaactgaaga ccagcgtcct cagttagatc 721 cttatcagat tcttggacca acaagtagcc gccttgcaaa tccaggcagt ggccagatcc 781 agctttggca gttcctcctg gagctcctgt cggacagctc caactccagc tgcatcacct 841 gggaaggcac caacggggag ttcaagatga cggatcccga cgaggtggcc cggcgctggg 901 gagagcggaa gagcaaaccc aacatgaact acgataagct cagccgcgcc ctccgttact 961 actatgacaa gaacatcatg accaaggtcc atggaagcg ctacgcctac aagttcgact 1021 tccacgggat cgcccaggcc ctccagcccc accccccgga gtcatctctg tacaagtacc 1081 cctcagacct cccgtacatg ggctcctatc acgcccaccc acagaagatg aactttgtgg 1141 cgccccaccc tccagccctc cccgtgacat cttccagttt ttttgctgcc caaacccat 1201 actggaattc accaactggg gtatatacc ccaacactag gctccccacc agccatatgc 1261 cttctcatct gggcacttac tactaaagac ctggcggagg cttttcccat cagcgtgcat 1321 tcaccagccc atcgccacaa actctatcgg agaacatgaa tcaaaagtgc ctcaagagga 1381 atgaaaaaag ctttactggg gctggggaag gaagccgggg aagagatcca aagactcttg 1441 ggagggagtt actgaagtct tactgaagtc ttactacaga aatgaggagg atgctaaaaa 1501 tgtcacgaat atggacatat catctgtgga ctgaccttgt aaaagacagt gtatgtagaa 1561 gcatgaagtc ttaaggacaa agtgccaaag aaagtggtct taagaaatgt ataaacttta 1621 gagtagagtt tgaatcccac taatgcaaac tgggatgaaa ctaaagcaat agaaacaaca 1681 cagtttttgac ctaacatacc gtttataatg ccatttaag gaaaactacc tgtatttaaa 1741 aatagtttca tatcaaaaac aagagaaaag acacgagaga gactgtggcc catcaacaga 1801 cgttgatatg caactgcatg gcatgtgctg ttttggttga atcaaatac attccgtttg 1861 atggacagct gtcagctttc tcaaactgtg aagatgaccc aaagtttcca actcctttac 1921 agtattaccg ggactatgaa ctaaaaggtg ggactgagga tgtgtataga gtgagcgtgt 1981 gattgtagac agagggtga agaaggagga ggaagaggca gagaaggagg agaccaggct 2041 gggaaagaaa cttctcaagc aatgaagact ggactcagga catttgggga ctgtgtacaa 2101 tgagttatgg agactcgagg gttcatgcag tcagtgttat accaaaccca gtgttaggag 2161 aaaggacaca gcgtaatgga gaaagggaag tagtagaatt cagaaacaaa aatgcgcatc 2221 tctttctttg tttgtcaaat gaaaatttta actggaattg tctgatattt aagagaaaca 2281 ttcaggacct catcattatg tgggggcttt gttctccaca gggtcaggta agagatggcc 2341 ttcttggctg ccacaatcag aaatcacgca ggcattttgg gtaggcggcc tccagttttc 2401 ctttgagtcg cgaacgctgt gcgtttgtca gaatgaagta tacaagtcaa tgttttccc 2461 ccttttata taataattat ataacttatg catttataca ctacgagttg atctcggcca 2521 gccaaagaca cacgacaaaa gagacaatcg atataatgtg gccttgaatt ttaactctgt 2581 atgcttaatg tttacaatat gaagttatta gttcttagaa tgcagaatgt atgtaataaa 2641 ataagcttgg cctagcatgg caaatcagat ttatacagga gtctgcattt gcactttttt
```

-continued

```
2701 tagtgactaa agttgcttaa tgaaaacatg tgctgaatgt tgtggatttt gtgttataat 2761 ttactttgtc caggaacttg tgcaagggag agccaaggaa ataggatgtt tggcacccaa 2821 atggcgtcag cctctccagg tccttcttgc ctcccctcct gtcttttatt tctagcccct 2881 tttggaacag gaaggacccc ggggtttcaa ttggagcctc catatttatg cctggaagga 2941 aagaggccta tgaagctggg gttgtcattg agaaattcta gttcagcacc tggtcacaaa 3001 tcacccttaa ttctgctatg attaaaatac atttgttgaa cagtgaacaa gctaccactc 3061 gtaaggcaaa ctgtattatt actggcaaat aaagcgtcat ggatagctgc aatttctcac 3121 tttaca
```

Nucleotides 195-1286 of SEQ ID NO:1 represent the coding sequence of SEQ ID NO:1.

The ERG2 coding sequence is publicly available through GenBank under the accession number M17254, as follows (with start and stop codons underlined):

```
                                                        (SEQ ID NO: 2)
   1 gtccgcgcgt gtccgcgccc gcgtgtgcca gcgcgcgtgc cttggccgtg cgcgccgagc 61 cgggtcgcac taactccctc ggcgccgacg gcggcgctaa cctctcggtt attccaggat 121 ctttggagac ccgaggaaag ccgtgttgac caaaagcaag acaaatgact cacagagaaa 181 aaagatggca gaaccaaggg caactaaagc cgtcaggttc tgaacagctg gtagatgggc 241 tggcttactg aaggacatga ttcagactgt cccggaccca gcagctcata tcaaggaagc 301 cttatcagtt gtgagtgagg accagtcgtt gtttgagtgt gcctacggaa cgccacacct 361 ggctaagaca gagatgaccg cgtcctcctc cagcgactat ggacagactt ccaagatgag 421 cccacgcgtc cctcagcagg attggctgtc tcaaccccca gccagggtca ccatcaaaat 481 ggaatgtaac cctagccagg tgaatggctc aaggaactct cctgatgaat gcagtgtggc 541 caaaggcggg aagatggtgg gcagcccaga caccgttggg atgaactacg gcagctacat 601 ggaggagaag cacatgccac ccccaaacat gaccacgaac gagcgcagag ttatcgtgcc 661 agcagatcct acgctatgga gtacagacca tgtgcggcag tggctggagt gggcggtgaa 721 agaatatggc cttccagacg tcaacatctt gttattccag aacatcgatg ggaaggaact 781 gtgcaagatg accaaggacg acttccagag gctcaccccc agctacaacg ccgacatcct 841 tctctcacat ctccactacc tcagagagac tcctcttcca catttgactt cagatgatgt 901 tgataaagcc ttacaaaact ctccacggtt aatgcatgct agaaacacag atttaccata 961 tgagcccccc aggagatcag cctggaccgg tcacggccac cccacgcccc agtcgaaagc 1021 tgctcaacca tctccttcca cagtgcccaa aactgaagac cagcgtcctc agttagatcc 1081 ttatcagatt cttggaccaa caagtagccg ccttgcaaat ccaggcagtg gccagatcca 1141 gctttggcag ttcctcctgg agctcctgtc ggacagctcc aactccagct gcatcacctg 1201 ggaaggcacc aacggggagt tcaagatgac ggatcccgac gaggtggccc ggcgctgggg 1261 agagcggaag agcaaaccca acatgaacta cgataagctc agccgcgccc tccgttacta 1321 ctatgacaag aacatcatga ccaaggtcca tgggaagcgc tacgcctaca gttcgactt 1381 ccacgggatc gcccaggccc tccagcccca ccccggag tcatctctgt acaagtaccc 1441 ctcagacctc ccgtacatgg ctcctatca cgcccaccca cagaagatga actttgtggc 1501 gccccaccct ccagccctcc ccgtgacatc ttccagtttt tttgctgccc caaacccata 1561 ctggaattca ccaactgggg gtatataccc caacactagg ctccccacca gccatatgcc 1621 ttctcatctg ggcacttact actaaagacc tggcggaggc ttttcccatc agcgtgcatt
```

-continued
```
1681 caccagccca tcgccacaaa ctctatcgga gaacatgaat caaaagtgcc tcaagaggaa 1741 tgaaaaaagc tttactgggg ctggggaagg aagccgggga agagatccaa agactcttgg 1801 gagggagtta ctgaagtctt actacagaaa tgaggaggat gctaaaaatg tcacgaatat 1861 ggacatatca tctgtggact gaccttgtaa aagacagtgt atgtagaagc atgaagtctt 1921 aaggacaaag tgccaaagaa agtggtctta agaaatgtat aaactttaga gtagagtttg 1981 aatcccacta atgcaaactg ggatgaaact aaagcaatag aaacaacaca gttttgacct 2041 aacataccgt ttataatgcc attttaagga aaactacctg tatttaaaaa tagtttcata 2101 tcaaaaacaa gagaaaagac acgagagaga ctgtggccca tcaacagacg ttgatatgca 2161 actgcatggc atgtgctgtt ttggttgaaa tcaaatacat tccgtttgat ggacagctgt 2221 cagctttctc aaactgtgaa gatgacccaa agtttccaac tcctttacag tattaccggg 2281 actatgaact aaaaggtggg actgaggatg tgtatagagt gagcgtgtga ttgtagacag 2341 aggggtgaag aaggaggagg aagaggcaga gaaggaggag accaggctgg gaaagaaact 2401 tctcaagcaa tgaagactgg actcaggaca tttggggact gtgtacaatg agttatggag 2461 actcgagggt tcatgcagtc agtgttatac caaacccagt gttaggagaa aggacacagc 2521 gtaatggaga aagggaagta gtagaattca gaaacaaaaa tgcgcatctc tttctttgtt 2581 tgtcaaatga aaattttaac tggaattgtc tgatatttaa gagaaacatt caggacctca 2641 tcattatgtg ggggctttgt tctccacagg gtcaggtaag agatggcctt cttggctgcc 2701 acaatcagaa atcacgcagg cattttgggt aggcggcctc cagttttcct ttgagtcgcg 2761 aacgctgtgc gtttgtcaga atgaagtata caagtcaatg tttttccccc tttttatata 2821 ataattatat aacttatgca tttatacact acgagttgat ctcggccagc caaagacaca 2881 cgacaaaaga gacaatcgat ataatgtggc cttgaatttt aactctgtat gcttaatgtt 2941 tacaatatga agttattagt tcttagaatg cagaatgtat gtaataaaat aagcttggcc 3001 tagcatggca aatcagattt atacaggagt ctgcatttgc actttttta gtgactaaag 3061 ttgcttaatg aaaacatgtg ctgaatgttg tggattttgt gttataattt actttgtcca 3121 ggaacttgtg caagggagag ccaaggaaat aggatgtttg gcaccc
```

Nucleotides 257-1645 of SEQ ID NO:2 represent the coding sequence of SEQ ID NO:2.

Figure 1A:
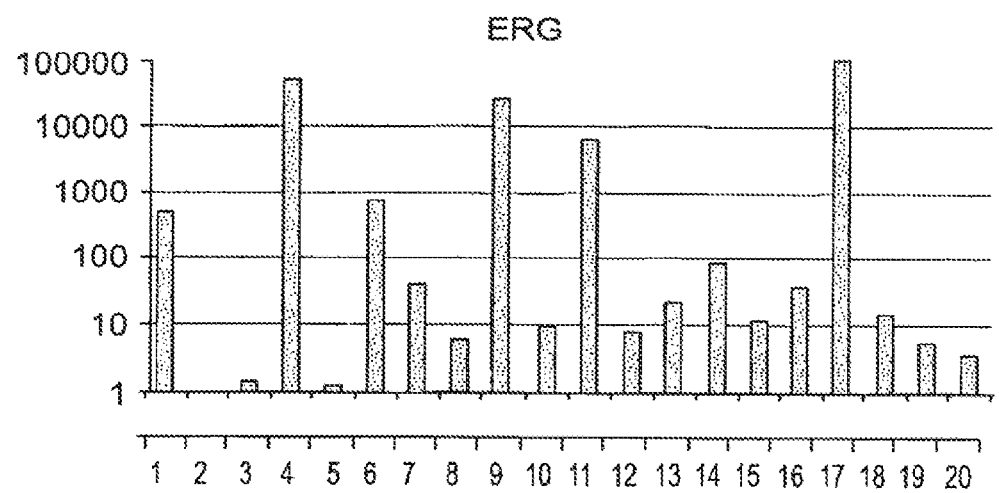
FIG. 1: Relative expression level of ERG (A), AMACR (B), GSTP1 (C), and LTF (D) in matched tumor and benign prostate epithelial cells analyzed by QRT-PCR (TaqMan)
Figure 1B:
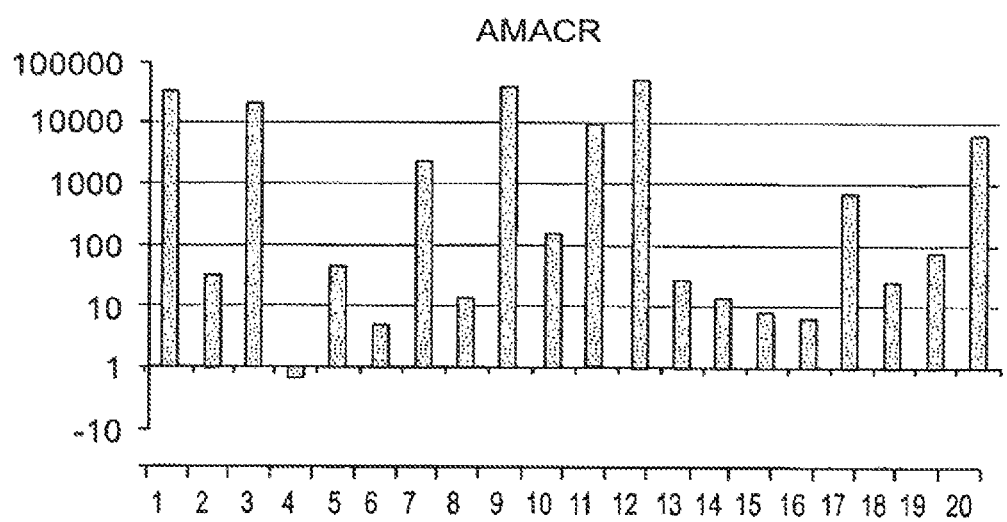
Figure 1C:
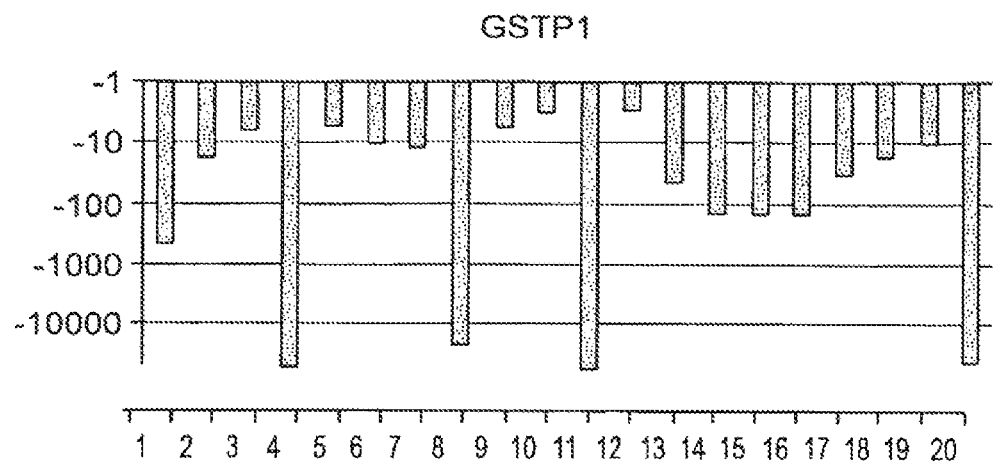

Validation by QRT-PCR (TaqMan) in microdissected tumor and benign prostate epithelial cells of 20 CaP patients confirmed a consistent, tumor associated over expression of ERG isoforms ERG1 and/or ERG2 in 95% of patients (19 of 20) (FIG. 1A). As a quality test and comparison, the expression of AMACR, a recently identified CaP tissue marker (Rubin et al, JAMA (2002) 287:1662-1670; Luo et al., Cancer Res (2002) 62: 2220-2226), and of GSTP1, a gene known to have decreased expression in CaP (Nelson et al., Ann N Y Acad Sci (2001) 952: 135-144), was also determined (FIGS. 1B and 1C). Robust over expression in CaP cells of 95% of the patients, similarly to ERG, was observed for AMACR, while the GSTP1 expression was significantly decreased in the tumor cells of each CaP patient, confirming the high quality of the tumor and benign LCM specimens and the reliability of the QRT-PCR.

Recently a detailed mapping of the chromosomal region (21q22.2-q22.3) containing the ERG gene, as well as a complete exon-intron structure with 9 alternative transcripts (or isoforms) has been described. (Owczarek et al., Gene (2004) 324: 65-77). The probes on the Affymetrix GeneChip used in our initial discovery of consistent ERG over expression in CaP, as well as the TaqMan probe designed for the validation experiment, recognize a region specific to the ERG 1 and 2 isoforms only.

Both ERG and ETS are proto-oncogenes with mitogenic and transforming activity. (Sharrocks, A D, Nat Rev Mol Cell Biol (2001) 2(11):827-37; Seth et al., Proc Natl Acad Sci USA (1989) 86:7833-7837). Deregulation or chromosomal reorganization of ERG is linked to Ewing sarcoma, myeloid leukemia and cervical carcinoma. (DeAlva et al., Int J Surg Pathol (2001) 9: 7-17; Simpson et al., Oncogene (1997) 14: 2149-2157; Shimizu et al., Proc Natl Acad Sci USA (1993) 90:10280-284; Papas, et al., Am J Med Genet Suppl. (1990) 7:251-261). ETS2 has been implicated in CaP, but it is over expressed only in a small proportion of CaP specimens. (Liu et al., Prostate (1997) 30:145-53; Semenchenko, et al., Oncogene (1998) 17:2883-88). ERG over expression without amplification of DNA copy number was recently reported in acute myeloid leukemia. (Balduc et al., Proc. Natl. Acad. Sci. USA (2004) 101:3915-20). Gavrilov et al., Eur J Cancer (2001) 37:1033-40 examined the expression of various transcription factors, including several proteins from the ETS family, in a very limited number of high-grade prostate cancer samples. Antibodies against the ETS family proteins, Elf-1 and Fli-1, caused intense staining of most of the high-grade prostate cancer samples. In contrast, ERG protein, while being detected in the noncancerous endothelial cells (microvessels in the stroma) of most samples tested, was detected in only a minority of the high-grade prostate cancers. ETS family proteins have a variety of expression patterns in human tissues. (Oikawa et al., Gene (2003) 303:11-34). ERG is expressed in endothelial tissues, hematopoietic cells, kidney, and in the urogenital tract. ERG proteins are nuclear transcription factors that form homodimers, as well as heterodimers with several other members of the ETS family of transcription factors. (Carrere et al., Oncogene (1998) 16(25): 3261-68). A negative crosstalk observed between ERG and estrogen receptor (ER-alpha) may be relevant in urogenital tissues, where both transcription factors are expressed. (Vlaeminck-Guillem et al., Oncogene (2003) 22(50):8072-84). The present invention is based in part upon the surprising discovery that ERG is over expressed in the majority of CaP specimens analyzed, indicating that this oncogene plays a role in prostate tumorigenesis, most likely by modulating transcription of target genes favoring tumorigenesis in prostate epithelium.

The present invention is further based in part upon the over expression of the AMACR gene in prostate cancer epithelium. The cDNA sequence of the AMACR is publicly available through GenBank under the accession numbers NM_014324 and AF047020. The sequence (with start and stop codons underlined) corresponding to accession number NM_014324 is as follows:

```
                                                                   (SEQ ID NO: 3)
   1 gggattggga gggcttcttg caggctgctg ggctggggct aagggctgct cagtttcctt 61 cagcggggca ctgggaagcg ccatggcact gcagggcatc tcggtcgtgg agctgtccgg 121 cctggccccg ggcccgttct gtgctatggt cctggctgac ttcggggcgc gtgtggtacg 181 cgtggaccgg cccggctccc gctacgacgt gagccgcttg ggccggggca agcgctcgct 241 agtgctggac ctgaagcagc cgcggggagc cgccgtgctg cggcgtctgt gcaagcggtc 301 ggatgtgctg ctggagccct tccgccgcgg tgtcatggag aaactccagc tgggcccaga 361 gattctgcag cgggaaaatc caaggcttat ttatgccagg ctgagtggat ttggccagtc 421 aggaagcttc tgccggttag ctggccacga tatcaactat ttggctttgt caggtgttct 481 ctcaaaaatt ggcagaagtg gtgagaatcc gtatgccccg ctgaatctcc tggctgactt 541 tgctggtggt ggccttatgt gtgcactggg cattataatg gctcttttg accgcacacg 601 cactggcaag ggtcaggtca ttgatgcaaa tatggtggaa ggaacagcat atttaagttc 661 ttttctgtgg aaaactcaga aattgagtct gtgggaagca cctcgaggac agaacatgtt 721 ggatggtgga gcacctttct atacgactta caggacagca gatggggaat tcatggctgt 781 tggagcaata gaacccagt tctacgagct gctgatcaaa ggacttggac taaagtctga 841 tgaacttccc aatcagatga gcatggatga ttggccagaa atgaagaaga gtttgcaga 901 tgtatttgca gagaagacga aggcagagtg gtgtcaaatc tttgacggca cagatgcctg 961 tgtgactccg gttctgactt ttgaggaggt tgttcatcat gatcacaaca aggaacgggg 1021 ctcgtttatc accagtgagg agcaggacgt gagccccccgc cctgcacctc tgctgttaaa 1081 cacccccagcc atccctttct tcaaaaggga tcctttcata ggagaacaca ctgaggagat 1141 acttgaagaa tttggattca gccgcgaaga gatttatcag cttaactcag ataaaatcat 1201 tgaaagtaat aaggtaaaag ctagtctcta acttccaggc ccacggctca agtgaatttg 1261 aatactgcat ttacagtgta gagtaacaca taacattgta tgcatggaaa catggaggaa 1321 cagtattaca gtgtcctacc actctaatca agaaaagaat tacagactct gattctacag 1381 tgatgattga attctaaaaa tggttatcat tagggctttt gatttataaa actttgggta 1441 cttatactaa attatggtag ttattctgcc ttccagtttg cttgatatat ttgttgatat 1501 taagattctt gacttatatt ttgaatgggt tctagtgaaa aaggaatgat atattcttga 1561 agacatcgat atacatttat ttacactctt gattctacaa tgtagaaaat gaggaaatgc 1621 cacaaattgt atggtgataa aagtcacgtg aaacagagtg attggttgca tccaggcctt 1681 ttgtcttggt gttcatgatc tccctctaag cacattccaa actttagcaa cagttatcac 1741 actttgtaat ttgcaaagaa aagtttcacc tgtattgaat cagaatgcct tcaactgaaa 1801 aaaacatatc caaaataatg aggaaatgtg ttggctcact acgtagagtc cagagggaca
```

```
-continued
1861 gtcagtttta gggttgcctg tatccagtaa ctcggggcct gtttccccgt gggtctctgg 1921 gctgtcagct ttcctttctc catgtgtttg atttctcctc aggctggtag caagttctgg 1981 atcttatacc caacacacag caacatccag aaataaagat ctcaggaccc cccagcaagt 2041 cgttttgtgt ctccttggac tgagttaagt tacaagcctt tcttatacct gtctttgaca 2101 aagaagacgg gattgtcttt acataaaacc agcctgctcc tggagcttcc ctggactcaa 2161 cttcctaaag gcatgtgagg aaggggtaga ttccacaatc taatccgggt gccatcagag 2221 tagagggagt agagaatgga tgttgggtag gccatcaata aggtccattc tgcgcagtat 2281 ctcaactgcc gttcaacaat cgcaagagga aggtggagca ggtttcttca tcttacagtt 2341 gagaaaacag agactcagaa gggcttctta gttcatgttt cccttagcgc ctcagtgatt 2401 ttttcatggt ggcttaggcc aaaagaaata tctaaccatt caatttataa ataattaggt 2461 ccccaacgaa ttaaatatta tgtcctacca acttattagc tgcttgaaaa atataataca 2521 cataaataaa aaaa
```

Nucleotides 83-1231 of SEQ ID NO:3 represent the coding sequence of AMACR.

The present invention is further based in part upon the over expression of the DD3 gene in prostate cancer epithelium. The cDNA sequence of the DD3 gene is publicly available through GenBank under the accession number AF103907. The sequence corresponding to accession number AF103907 is as follows:

(SEQ ID NO: 4)
```
   1 acagaagaaa tagcaagtgc cgagaagctg gcatcagaaa aacagagggg agatttgtgt 61 ggctgcagcc gagggagacc aggaagatct gcatggtggg aaggacctga tgatacagag 121 gaattacaac acatatactt agtgtttcaa tgaacaccaa gataaataag tgaagagcta 181 gtccgctgtg agtctcctca gtgacacagg gctggatcac catcgacggc actttctgag 241 tactcagtgc agcaaagaaa gactacagac atctcaatgg caggggtgag aaataagaaa 301 ggctgctgac tttaccatct gaggccacac atctgctgaa atggagataa ttaacatcac 361 tagaaacagc aagatgacaa tataatgtct aagtagtgac atgtttttgc acatttccag 421 cccctttaaa tatccacaca cacaggaagc acaaaaggaa gcacagagat ccctgggaga 481 aatgcccggc cgccatcttg ggtcatcgat gagcctcgcc ctgtgcctgg tcccgcttgt 541 gagggaagga cattagaaaa tgaattgatg tgttccttaa aggatgggca ggaaaacaga 601 tcctgttgtg gatatttatt tgaacgggat tacagatttg aaatgaagtc acaaagtgag 661 cattaccaat gagaggaaaa cagacgagaa atcttgatg gcttcacaag acatgcaaca 721 aacaaaatgg aatactgtga tgacatgagg cagccaagct ggggaggaga taaccacggg 781 gcagagggtc aggattctgg ccctgctgcc taaactgtgc gttcataacc aaatcatttc 841 atatttctaa ccctcaaaac aaagctgttg taatatctga tctctacggt tccttctggg 901 cccaacattc tccatatatc cagccacact cattttttaat atttagttcc cagatctgta 961 ctgtgacctt tctacactgt agaataacat tactcattt gttcaaagac ccttcgtgtt 1021 gctgcctaat atgtagctga ctgtttttcc taaggagtgt tctggcccag gggatctgtg 1081 aacaggctgg gaagcatctc aagatctttc cagggttata cttactagca cacagcatga 1141 tcattacgga gtgaattatc taatcaacat catcctcagt gtctttgccc atactgaaat 1201 tcatttccca cttttgtgcc cattctcaag acctcaaaat gtcattccat taatatcaca 1261 ggattaactt ttttttttaa cctggaagaa ttcaatgtta catgcagcta tgggaattta 1321 attacatatt ttgttttcca gtgcaaagat gactaagtcc tttatccctc cccttttgttt 1381 gattttttt ccagtataaa gttaaaatgc ttagccttgt actgaggctg tatacagcac
```

-continued

```
1441 agcctctccc catccctcca gccttatctg tcatcaccat caacccctcc cataccacct 1501 aaacaaaatc taacttgtaa ttccttgaac atgtcaggac atacattatt ccttctgcct 1561 gagaagctct tccttgtctc ttaaatctag aatgatgtaa agttttgaat aagttgacta 1621 tcttacttca tgcaaagaag ggacacatat gagattcatc atcacatgag acagcaaata 1681 ctaaaagtgt aatttgatta taagagttta gataaatata tgaaatgcaa gagccacaga 1741 gggaatgttt atggggcacg tttgtaagcc tgggatgtga agcaaaggca gggaacctca 1801 tagtatctta tataatatac ttcatttctc tatctctatc acaatatcca caagcttttt 1861 cacagaattc atgcagtgca aatccccaaa ggtaaccttt atccatttca tggtgagtgc 1921 gctttagaat tttggcaaat catactggtc acttatctca actttgagat gtgtttgtcc 1981 ttgtagttaa ttgaaagaaa tagggcactc ttgtgagcca ctttagggtt cactcctggc 2041 aataaagaat ttacaaagag ctactcagga ccagttgtta agagctctgt gtgtgtgtgt 2101 gtgtgtgtgt gagtgtacat gccaaagtgt gcctctctct cttgacccat tatttcagac 2161 ttaaaacaag catgttttca atggcacta tgagctgcca atgatgtatc accaccatat 2221 ctcattattc tccagtaaat gtgataataa tgtcatctgt taacataaaa aaagtttgac 2281 ttcacaaaag cagctggaaa tggacaacca caatatgcat aaatctaact cctaccatca 2341 gctacacact gcttgacata tattgttaga agcacctcgc atttgtgggt tctcttaagc 2401 aaaatacttg cattaggtct cagctggggc tgtgcatcag gcggtttgag aaatattcaa 2461 ttctcagcag aagccagaat ttgaattccc tcatctttta ggaatcattt accaggtttg 2521 gagaggattc agacagctca ggtgctttca ctaatgtctc tgaacttctg tccctctttg 2581 tgttcatgga tagtccaata aataatgtta tctttgaact gatgctcata ggagagaata 2641 taagaactct gagtgatatc aacattaggg attcaaagaa atattagatt taagctcaca 2701 ctggtcaaaa ggaaccaaga tacaaagaac tctgagctgt catcgtcccc atctctgtga 2761 gccacaacca acagcaggac ccaacgcatg tctgagatcc ttaaatcaag gaaaccagtg 2821 tcatgagttg aattctccta ttatggatgc tagcttctgg ccatctctgg ctctcctctt 2881 gacacatatt agcttctagc ctttgcttcc acgactttta tcttttctcc aacacatcgc 2941 ttaccaatcc tctctctgct ctgttgcttt ggacttcccc acaagaattt caacgactct 3001 caagtctttt cttccatccc caccactaac ctgaatgcct agacccttat ttttattaat 3061 ttccaataga tgctgcctat gggctatatt gctttagatg aacattagat atttaaagct 3121 caagaggttc aaaatccaac tcattatctt ctctttcttt cacctccctg ctcctctccc 3181 tatattactg attgcactga acagcatggt ccccaatgta gccatgcaaa tgagaaaccc 3241 agtggctcct tgtggtacat gcatgcaaga ctgctgaagc cagaaggatg actgattacg 3301 cctcatgggt ggaggggacc actcctgggc cttcgtgatt gtcaggagca agacctgaga 3361 tgctccctgc cttcagtgtc ctctgcatct ccccttttcta atgaagatcc atagaatttg 3421 ctacatttga gaattccaat taggaactca catgttttat ctgccctatc aattttttaa 3481 acttgctgaa aattaagttt tttcaaaatc tgtccttgta aattacttt tcttacagtg 3541 tcttggcata ctatatcaac tttgattctt tgttacaact tttcttactc ttttatcacc 3601 aaagtggctt ttattctctt tattattatt attttctttt actactatat tacgttgtta 3661 ttattttgtt ctctatagta tcaatttatt tgatttagtt tcaatttatt tttattgctg 3721 acttttaaaa taagtgattc ggggggtggg agaacagggg agggagagca ttaggacaaa 3781 tacctaatgc atgtgggact taaaacctag atgatgggtt gataggtgca gcaaaccact
```

-continued

```
3841 atggcacacg tatacctgtg taacaaacct acacattctg cacatgtatc ccagaacgta 3901 aagtaaaatt taaaaaaaag tga
```

The DD3 gene appears to represent a non-coding nucleic acid. Therefore, no start and stop codons have been indicated.

The present invention is further based in part upon the under expression of the LTF gene in prostate cancer epithelium. The cDNA sequence of the lactotransferrin (LTF) gene is publicly available through GenBank under the accession number NM_002343. The sequence (with start and stop codons underlined) corresponding to accession number NM_002343 is as follows:

(SEQ ID NO: 5)
```
   1 agagccttcg tttgccaagt cgcctccaga ccgcagacat gaaacttgtc ttcctcgtcc
  61 tgctgttcct cggggccctc ggactgtgtc tggctggcca taggaggagt gttcagtggt
 121 gcgccgtatc ccaacccgag gccacaaaat gcttccaatg gcaaaggaat atgagaaaag
 181 tgcgtggccc tcctgtcagc tgcataaaga gagactcccc catccagtgt atccaggcca
 241 ttgcggaaaa cagggccgat gctgtgaccc ttgatggtgg tttcatatac gaggcaggcc
 301 tggccccta caaactgcga cctgtagcgg cggaagtcta cggaccgaa agacagccac
 361 gaactcacta ttatgccgtg gctgtggtga agaagggcgg cagctttcag ctgaacgaac
 421 tgcaaggtct gaagtcctgc cacacaggcc ttcgcaggac cgctggatgg aatgtcccta
 481 tagggacact tcgtccattc ttgaattgga cgggtccacc tgagcccatt gaggcagctg
 541 tggccaggtt cttctcagcc agctgtgttc ccggtgcaga taaaggacag ttccccaacc
 601 tgtgtcgcct gtgtgcgggg acaggggaaa acaaatgtgc cttctcctcc aggaaccgt
 661 acttcagcta ctctggtgcc ttcaagtgtc tgagagacgg ggctggagac gtggcttta
 721 tcagagagag cacagtgttt gaggacctgt cagacgaggc tgaaagggac gagtatgagt
 781 tactctgccc agacaacact cggaagccag tggacaagtt caaagactgc catctggccc
 841 gggtcccttc tcatgccgtt gtggcacgaa gtgtgaatgg caaggaggat gccatctgga
 901 atcttctccg ccaggcacag gaaaagtttg gaaaggacaa gtcaccgaaa ttccagctct
 961 ttggctcccc tagtgggcag aaagatctgc tgttcaagga ctctgccatt gggttttcga
1021 gggtgccccc gaggatagat tctgggctgt accttggctc cggctacttc actgccatcc
1081 agaacttgag gaaaagtgag gaggaagtgg ctgcccggcg tgcgcgggtc gtgtggtgtg
1141 cggtgggcga gcaggagctg cgcaagtgta accagtggag tggcttgagc gaaggcagcg
1201 tgacctgctc ctcggcctcc accacagagg actgcatcgc cctggtgctg aaaggagaag
1261 ctgatgccat gagtttggat ggaggatatg tgtacactgc aggcaaatgt ggtttggtgc
1321 ctgtcctggc agagaactac aaatcccaac aaagcagtga ccctgatcct aactgtgtgg
1381 atagacctgt ggaaggatat cttgctgtgg cggtggttag gagatcagac actagcctta
1441 cctggaactc tgtgaaaggc aagaagtcct gccacaccgc cgtggacagg actgcaggct
1501 ggaatatccc catgggcctg ctcttcaacc agacgggctc ctgcaaattt gatgaatatt
1561 tcagtcaaag ctgtgcccct gggtctgacc cgagatctaa tctctgtgct ctgtgtattg
1621 gcgacgagca gggtgagaat aagtgcgtgc ccaacagcaa cgagagatac tacggctaca
1681 ctggggcttt ccggtgcctg gctgagaatg ctggagacgt tgcatttgtg aaagatgtca
1741 ctgtcttgca gaacactgat ggaaataaca atgaggcatg ggctaaggat ttgaagctgg
1801 cagactttgc gctgctgtgc ctcgatggca aacggaagcc tgtgactgag gctagaagct
1861 gccatcttgc catggcccg aatcatgccg tggtgtctcg gatggataag gtggaacgcc
1921 tgaaacaggt gttgctccac caacaggcta aatttggag aaatggatct gactgcccgg
1981 acaagttttg cttattccag tctgaaacca aaaaccttct gttcaatgac aacactgagt
```

```
-continued
2041 gtctggccag actccatggc aaaacaacat atgaaaaata tttgggacca cagtatgtcg 2101 caggcattac taatctgaaa aagtgctcaa cctccccct cctggaagcc tgtgaattcc 2161 tcaggaagta aaaccgaaga agatggccca gctccccaag aaagcctcag ccattcactg 2221 cccccagctc ttctccccag gtgtgttggg gccttggcct ccctgctga aggtggggat 2281 tgcccatcca tctgcttaca attccctgct gtcgtcttag caagaagtaa aatgagaaat 2341 tttgttgata ttctctcctt aaaaaaaaaa aaaaaaaaaa aaaaaaaaaa
```

Nucleotides 39-2171 of SEQ ID NO:5 represent the coding sequence of LTF.

LTF is a non-heme iron binding glycoprotein and a member of the transferring gene family. Bowman et al., Adv. Genet. 25:1-38 (1988); Park et al., Proc. Natl. Acad. Sci. U.S.A., 82:3149-53 (1985). The concentration of LTF in human prostate is hormone dependent and its expression is regulated by estrogen. van Sande et al., Urol. Res., 9(5): 241-244 (1981); Teng et al., Biochem. Cell Biol., 80:7-16 (2002); Teng et al., Mol. Human Reproduction., 8, (1):58-67 (2002). LTF has also been implicated in certain cancers. For example, bovine LTF inhibits colon, esophagus, lung, and bladder carcinomas in rats. Tsuda et al., Biochem. Cell Biol., 80:131-136 (2002); Tsuda et al., Biofactors., 12(1-4):83-8 (2000); Tsuda et al., Biofactors., 12(1-4):83-8 (2000); Tsuda et al., Mutat Res., 462(2-3):227-33 (2000). In a study published over 20 years ago, van Sande et al., Urol. Res. 9:241-244 (1981), examined lactoferrin protein levels in human benign prostatic hypertrophy samples. They also detected low levels of lactoferrin protein in 3 carcinoma samples. However, we are the first to report the consistent and significant under expression of LTF mRNA in prostate cancer epithelial cells from a large number of patient samples. The observed under expression of LTF mRNA in such a statistically significant sample size indicates that under expression of LTF is a useful diagnostic marker for prostate cancer.

In one experiment, when screened using the Affymetrix GeneChip, CaP tumor cells exhibited upregulated AMACR expression in comparison to matched benign cells. In this studied patient cohort (n=73), AMACR was upregulated in tumor compared to matched benign prostate epithelium in 89.04% of the patients (65 of 73), while ERG was upregulated in 78.08% (57 of 73). When these two markers were combined, we observed a 100% CaP detection rate (under the criteria that at least one marker was upregulated) in the studied patient cohort (73 of 73). These data indicate that the combination of ERG and AMACR screening provides a highly accurate tool for CaP detection.

In another experiment, 96.4% of patients showed upregulation of either the ERG or AMACR gene in laser microdissected matched tumor and benign prostate epithelial cells from 55 CaP patients (FIG. 5). Similarly, 96.4% of patients showed upregulation of either the ERG or DD3 gene (FIG. 5). When the expression data for the ERG, AMACR, and DD3 genes was combined, 98.2% of the CaP patients showed upregulation of at least one of the three genes in tumor cells (FIG. 5). Thus, the combination of ERG, AMACR, and DD3 screening also provides a highly accurate tool for CaP detection.

Figure 1D:
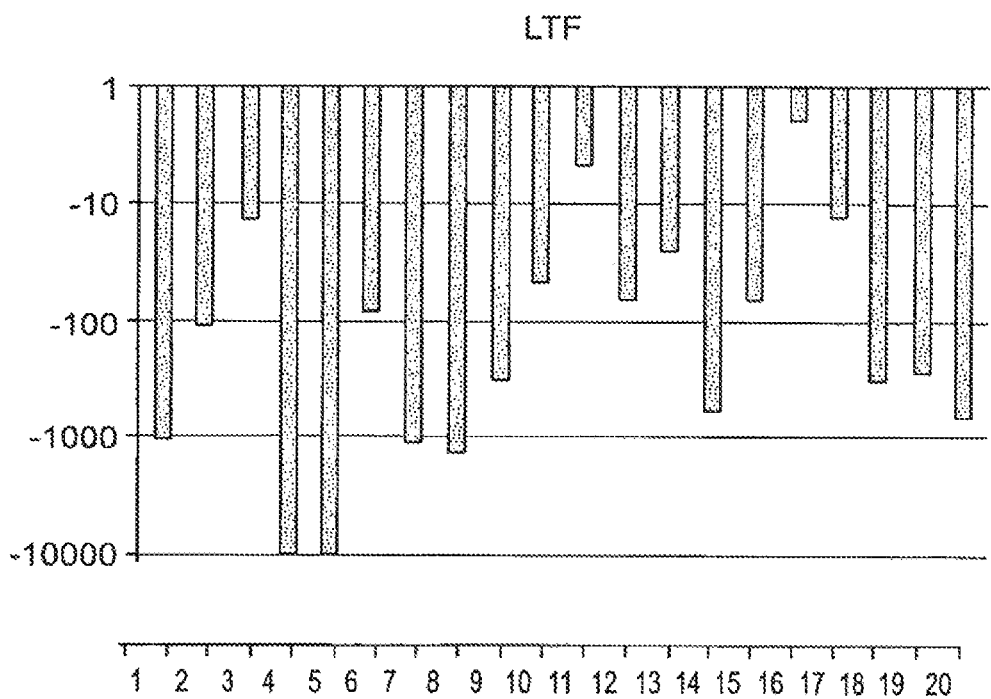

In yet another experiment, validation by QRT-PCR (TaqMan) in microdissected tumor and benign prostate epithelial cells of 20 CaP patients confirmed a consistent, tumor associated under expression of LTF in 100% of patients (20 of 20) (FIG. 1D). Further validation studies by QRT-PCR in microdissected tumor and benign prostate epithelial cells of 103 CaP patients were consistent with the initial results, showing tumor associated under expression in 76% of patients (78 of 103).

Diagnostic Uses

In one embodiment, the present invention comprises a method of CaP diagnosis comprising screening biological samples for CaP-cell-specific gene expression signatures. In particular, the invention comprises screening for at least one of the CaP-cell-specific genes listed in Tables 1-6, particularly the ERG gene, the AMACR gene, the LTF gene or a combination of the ERG gene and the AMACR genes. The invention also comprises methods of diagnosing CaP comprising screening biological samples for expression of the ERG and DD3 genes, or a combination of the ERG, DD3, and AMACR genes.

In a further embodiment, the present invention comprises a method of CaP diagnosis comprising screening biological samples for CaP-cell-specific gene expression signatures using methods known in the art, including, for example, immunohistochemistry, ELISA, in situ RNA hybridization, and any oligonucleotide amplification procedure known or later developed, including PCR (including QRT-PCR), transcription-mediated amplification (TMA), nucleic acid sequence-based amplification (NASBA), self-sustained sequence replication (3SR), ligase chain reaction (LCR), strand displacement amplification (SDA), and Loop-Mediated Isothermal Amplification (LAMP). See, e.g., Mullis, U.S. Pat. No. 4,683,202; Erlich et al., U.S. Pat. No. 6,197,563; Walker et al., Nucleic Acids Res., 20:1691-1696 (1992); Fahy et al., PCR Methods and Applications, 1:25-33 (1991); Kacian et al., U.S. Pat. No. 5,399,491; Kacian et al., U.S. Pat. No. 5,480,784; Davey et al., U.S. Pat. No. 5,554,517; Birkenmeyer et al., U.S. Pat. No. 5,427,930; Marshall et al., U.S. Pat. No. 5,686,272; Walker, U.S. Pat. No. 5,712,124; Notomi et al., European Patent Application No. 1 020 534 A1; Dattagupta et al., U.S. Pat. No. 6,214,587; and HELEN H. LEE ET AL., NUCLEIC ACID AMPLIFICATION TECHNOLOGIES: APPLICATION TO DISEASE DIAGNOSIS (1997). Each of the foregoing amplification references is hereby incorporated by reference herein. In particular, the invention comprises generating antibodies to CaP-cell-specific genes, including ERG, AMACR, LTF, and DD3 for use in a immunohistochemistry assay. Other known diagnostic assays may be used to detect gene expression.

In a specific embodiment, the present invention comprises a method of diagnosing CaP comprising screening biological samples for expression of the ERG and AMACR genes, the ERG and DD3 genes, or the ERG, AMACR, and DD3 genes, or the LTF gene using methods known in the art, including, for example, immunohistochemistry, ELISA, in situ hybridization, PCR (including QRT-PCR), transcription-mediated amplification (TMA), nucleic acid sequence-based amplification (NASBA), self-sustained sequence replication (3SR), ligase chain reaction (LCR), strand displacement amplification (SDA), and Loop-Mediated Isothermal Amplification (LAMP).

ERG, LTF, or AMACR polypeptides, their fragments or other derivatives, or analogs thereof, may be used as immunogens in order to generate antibodies that specifically bind such immunogens. Such antibodies include, but are not limited to, polyclonal, monoclonal, chimeric, single chain and Fab fragments. In a specific embodiment, antibodies to a human ERG, LTF or AMACR protein are produced. Antibodies can then be used in standard diagnostic assays to detect the protein produced by the desired gene.

Various procedures known in the art may be used for the production of polyclonal antibodies to an ERG, LTF, or AMACR protein or derivative or analog. In a particular embodiment, rabbit polyclonal antibodies to an epitope of a ERG, LTF, or AMACR protein can be obtained. For the production of antibody, various host animals can be immunized by injection with the native ERG, LTF, or AMACR protein, or a synthetic version, or derivative (e.g., fragment) thereof, including but not limited to rabbits, mice, rats, etc. Various adjuvants may be used to increase the immunological response, depending on the host species, and including, but not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward a ERG, LTF, or AMACR protein sequence or analog thereof, any technique, which provides for the production of antibody molecules by continuous cell lines in culture may be used. For example, the hybridoma technique originally developed by Kohler et al (1975) Nature, 256:495-497, as well as the trioma technique, the human B-cell hybridoma technique (Kozbor et al. (1983) Immunology Today, 4:72), and the EBV-hybridoma technique to produce human monoclonal antibodies (Cole et al. (1985) Monoclonal Antibodies and Cancer Therapy, Alan R. Liss, Inc., pp. 77-96). According to the invention, human antibodies may be used and can be obtained by using human hybridomas (Cote et al. (1983) Proc. Natl. Acad. Sci. U.S.A., 80:2026-2030) or by transforming human B cells with EBV virus in vitro (Cole et al. (1985) Monoclonal Antibodies and Cancer Therapy, Alan R. Liss, pp. 77-96). According to the invention, techniques developed for the production of chimeric antibodies (Morrison et al. (1984) Proc. Natl. Acad. Sci. U.S.A., 81:6851-6855; Neuberger et al. (1984) Nature, 312:604-608; Takeda et al. (1985) Nature, 314:452-454) by splicing the genes from a mouse antibody molecule specific for ERG, LTF, or AMACR together with genes from a human antibody molecule of appropriate biological activity can be used; such antibodies are within the scope of this invention.

Techniques described for the production of single chain antibodies (U.S. Pat. No. 4,946,778) can be used to produce ERG-, LTF-, or AMACR-specific single chain antibodies. An additional embodiment of the invention utilizes the techniques described for the construction of Fab expression libraries (Huse et al. (1989) Science, 246:1275-1281) to allow rapid and easy identification of monoclonal Fab fragments with the desired specificity for ERG, LTF or AMACR proteins, derivatives, or analogs.

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, the Fab fragments which can be generated by treating the antibody molecule with papain and a reducing agent, and Fv fragments, including single chain Fv (scFv) fragments.

In the production of antibodies, screening for the desired antibody can be accomplished by techniques known in the art, e.g., ELISA. For example, to select antibodies that recognize a specific domain of a ERG, LTF, or AMACR protein, one may assay generated hybridomas for a product which binds to a ERG, LTF, or AMACR fragment containing such domain.

A second aspect of the invention provides for use of the expression profiles resulting from these methods in diagnostic methods, including, but not limited to, characterizing the treatment response to any therapy, correlating expression profiles with clinico-pathologic features, distinguishing indolent prostate cancers from those with a more aggressive phenotype (e.g. moderate risk versus high risk), analyzing tumor specimens of patients treated by radical prostate surgery to help define prognosis, screening candidate genes for the development of a polynucleotide array for use as a blood test for improved prostate cancer detection, and identifying further genes that may serve as biomarkers for response to treatment to screen drugs for the treatment of advanced prostate cancer.

As will be readily appreciated by persons having skill in the art, the ERG, LTF, DD3, and/or the AMACR nucleic acid sequences described herein can easily be synthesized directly on a support, or pre-synthesized polynucleotide probes may be affixed to a support as described, for example, in U.S. Pat. Nos. 5,744,305, 5,837,832, and 5,861,242, each of which is incorporated herein by reference.

Such arrays may be used to detect specific nucleic acid sequences contained in a target cell or sample, as described in U.S. Pat. Nos. 5,744,305, 5,837,832, and 5,861,242, each of which is incorporated herein by reference. More specifically, in the present invention, these arrays may be used in methods for the diagnosis or prognosis of prostate cancer, such as by assessing the expression profiles of genes, in biological samples. In a preferred embodiment, computer models may be developed for the analysis of expression profiles. Moreover, such polynucleotide arrays are useful in methods to screen drugs for the treatment of advanced prostate cancer. In these screening methods, the polynucleotide arrays are used to analyze how drugs affect the expression of the ERG, LTF, AMACR, and/or DD3 genes.

Therapeutic Uses

The invention provides for treatment or prevention of various diseases and disorders by administration of a therapeutic compound (termed herein "therapeutic"). "Therapeutics" include but are not limited to: ERG or LTF proteins and analogs and derivatives (including fragments) thereof (e.g., as described herein above); nucleic acids encoding the ERG or LTF proteins, analogs, or derivatives; ERG or LTF antisense nucleic acids, ERG or LTF dominant negative mutants, siRNA against ERG or LTF, ERG or LTF antibodies and ERG or LTF agonists and antagonists. ERG or LTF agonists and antagonists, including small molecules, can be identified using the methods disclosed in this application or any standard screening assay to identify agents that modulate ERG or LTF expression or function, particularly in prostate cancer cells. For example, ERG or LTF expression or function can be readily detected, e.g., by obtaining a biological sample from a patient, e.g., a tissue sample (e.g., from biopsy tissue), a blood sample, or a urine sample, and assaying it in vitro for mRNA or protein levels, structure and/or activity of the expressed ERG or LTF mRNA or protein. Many methods standard in the art can be employed, including but not limited to, kinase assays, immunoassays to detect and/or visualize ERG or LTF protein (e.g., Western blot, immunoprecipitation followed by SDS-PAGE, immunocytochemistry, etc.) and/or hybridization assays to detect ERG or LTF expression by detecting and/or visualizing ERG or LTF mRNA (e.g., Northern assays, dot blots, in situ hybridization, PCR (including RT-PCR), TMA, NASAB, 3SR, LCR, SDA, LAMP, etc.).

Hyperproliferative Disorders

Disorders involving hyperproliferation of cells are treated or prevented by administration of a therapeutic that antagonizes (reduces or inhibits) ERG function or expression or enhances LTF function or expression. In certain embodiments, ERG function is inhibited by use of ERG antisense nucleic acids. The present invention provides the therapeutic or prophylactic use of nucleic acids of at least 10, 15, 100, 200, 500, 1000, 1500, 2000, or 2500 contiguous nucleotides in antisense to any of the ERG nucleotides described herein. In a particular embodiment, the ERG antisense nucleic acid comprises at least 10, 15, 100, 200, 500, 1000, 1500, 2000, or 2500 contiguous nucleotides in antisense orientation to the ERG nucleotide sequence. An ERG "antisense" nucleic acid as used herein refers to a nucleic acid capable of hybridizing under defined conditions to a portion of an ERG nucleic acid by virtue of some sequence complementarity. The antisense nucleic acid may be complementary to a coding and/or noncoding region of an ERG nucleic acid. Such antisense nucleic acids have utility as therapeutics that inhibit ERG function, and can be used in the treatment or prevention of disorders as described herein.

The antisense nucleic acids of the invention can be oligonucleotides that are double-stranded or single-stranded, RNA or DNA or a modification or derivative thereof, which can be directly administered to a cell, or which can be produced intracellularly by transcription of exogenously, introduced coding sequences.

The dominant negative mutants of the invention can be produced by expression plasmids containing a nucleic acid encoding a non-functional domain of ERG, such as the DNA binding domain of ERG. These expression plasmids can be introduced into a target cell or tissue and can induce tumor growth inhibition and apoptosis by acting as a dominant negative form against the wild-type ERG transcription factors influencing cell hyperproliferation (Oikawa, Cancer Sci (2004), 95:626-33).

RNA interference can be achieved using siRNA against the ERG gene. The siRNA is a short double stranded RNA molecule of about 18-25 nucleotides that comprises a nucleotide sequence complementary to a region of the target gene. The siRNA can be introduced into a target cell or tissue, for example using an expression plasmid, where it interferes with the translation of the ERG gene. RNA interference techniques can be carried out using known methods as described, for example, in published U.S. Patent Applications 20040192626, 20040181821, and 20030148519, each of which is incorporated by reference.

Therapeutics which are useful according to this embodiment of the invention for treatment of a disorder may be selected by testing for biological activity in promoting the survival or differentiation of cells. For example, in a specific embodiment relating to cancer therapy, including therapy of prostate cancer, a therapeutic decreases proliferation of tumor cells. These effects can be measured as described in the Examples or using any other method standard in the art.

In specific embodiments, malignancy or dysproliferative changes (such as metaplasias and dysplasias), or hyperproliferative disorders, are treated or prevented in the prostate.

The therapeutics of the invention that antagonize ERG activity can also be administered to treat premalignant conditions and to prevent progression to a neoplastic or malignant state, including but not limited to those disorders described herein, such as prostate cancer.

Gene Therapy

In a specific embodiment, nucleic acids comprising a sequence encoding an ERG or LTF protein or functional derivative thereof, are administered to promote ERG or LTF function, by way of gene therapy. Alternatively, nucleic acids comprising an antisense ERG sequence are administered to antagonize ERG expression or function. Gene therapy refers to therapy performed by the administration of a nucleic acid to a subject.

Any of the methods for gene therapy available in the art can be used according to the present invention. For specific protocols, see Morgan (2001) Gene Therapy Protocols, $2^{nd}$ ed., Humana Press. For general reviews of the methods of gene therapy, see Goldspiel et al. (1993) Clinical Pharmacy, 12:488-505; Wu et al. (1991) Biotherapy, 3:87-95; Tolstoshev (1993) Ann. Rev. Pharmacol. Toxicol., 32:573-596; Mulligan (1993) Science, 260:926-932; and Morgan et al. (1993) Ann. Rev. Biochem., 62:191-217; May (1993) TIBTECH, 11(5):155-215). Methods commonly known in the art of recombinant DNA technology which can be used are described in Current Protocols in Molecular Biology (2004), Ausubel et al., eds., John Wiley & Sons, NY; and Kriegler (1990) Gene Transfer and Expression, A Laboratory Manual, Stockton Press, NY.

In one embodiment, the therapeutic comprises an ERG or LTF nucleic acid or antisense ERG nucleic acid that is part of a vector. In particular, such a nucleic acid has a regulatory sequence, such as a promoter, operably linked to the ERG or LTF coding region or antisense molecule, said promoter being inducible or constitutive, and, optionally, tissue-specific. In another particular embodiment, a nucleic acid molecule is used in which the ERG or LTF coding sequences and any other desired sequences are flanked by regions that promote homologous recombination at a desired site in the genome, thus providing for intrachromosomal expression of the ERG or LTF nucleic acid (Koller et al. (1989) Proc. Natl. Acad. Sci. U.S.A., 86:8932-8935; Zijlstra et al. (1989) Nature, 342:435-438).

In a specific embodiment, the nucleic acid to be introduced for purposes of gene therapy comprises an inducible promoter operably linked to the desired nucleic acids, such that expression of the nucleic acid is controllable by the appropriate inducer of transcription.

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286, which is incorporated herein by reference), or by direct injection of naked DNA, or by use of microparticle bombardment (e.g., a gene gun; Biolistic, DuPont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see, e.g., Wu et al. (1987) J. Biol. Chem., 262:4429-4432). In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell-specific uptake and expression, by targeting a specific receptor (see, e.g., PCT Pubs. WO 92/06180; WO 92/22635; WO92/20316; WO93/14188; WO 93/20221). Alternatively, the nucleic acid can be introduced intracellularly and incorporated within host cell DNA for expression, by homologous recombination (Koller et al. (1989) Proc. Natl. Acad. Sci. U.S.A., 86:8932-8935; Zijlstra et al. (1989) Nature, 342:435-438).

In a specific embodiment, a viral vector that contains an ERG or LTF nucleic acid is used. For example, a retroviral vector can be used (see, Miller et al. (1993) Meth. Enzymol., 217:581-599). These retroviral vectors have been modified to delete retroviral sequences that are not necessary for packaging of the viral genome and integration into host cell DNA. The ERG or LTF nucleic acid to be used in gene therapy is cloned into the vector, which facilitates delivery of the gene into a patient. More detail about retroviral vectors can be found in Boesen et al. (1994) Biotherapy, 6:291-302, which describes the use of a retroviral vector to deliver the MDR1 gene to hematopoietic stem cells in order to make the stem cells more resistant to chemotherapy. Other references illustrating the use of retroviral vectors in gene therapy are: Clowes et al. (1994) J. Clin. Invest., 93:644-651; Kiem et al. (1994) Blood, 83:1467-1473; Salmons et al. (1993) Hum. Gene Ther., 4:129-141; and Grossman et al. (1993) Curr. Opin. Gen. Devel., 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky et al. (1993, Curr. Opin. Gen. Devel., 3:499-503) present a review of adenovirus-based gene therapy. Bout et al. (1994, Hum. Gene Ther., 5:3-10) demonstrated the use of adenovirus vectors to transfer genes to the respiratory epithelia of rhesus monkeys. Other instances of the use of adenoviruses in gene therapy can be found in Rosenfeld et al. (1991) Science, 252:431-434; Rosenfeld et al. (1992) Cell, 68:143-155; and Mastrangeli et al. (1993) J. Clin. Invest., 91:225-234.

Adeno-associated virus (AAV) has also been proposed for use in gene therapy (Walsh et al. (1993) Proc. Soc. Exp. Biol. Med., 204:289-300).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler et al. (1993) Meth. Enzymol., 217:599-618; Cohen et al. (1993) Meth. Enzymol., 217:618-644; Cline (1985) Pharmac. Ther., 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In one preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) may be administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include, but are not limited to, epithelial cells, endothelial cells, keratinocytes, fibroblasts, muscle cells, hepatocytes, lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc. In certain embodiments, the cells used for gene therapy are autologous to the patient.

In one embodiment, an ERG or LTF nucleic acid or antisense molecule is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention. Such stem cells include, but are not limited to, hematopoietic stem cells (HSC), stem cells of epithelial tissues such as the skin and the lining of the gut, embryonic heart muscle cells, liver stem cells (PCT Pub. WO 94/08598), and neural stem cells (Stemple et al. (1992) Cell, 71:973-985).

Epithelial stem cells (ESCs) or keratinocytes can be obtained from tissues such as the skin and the lining of the gut by known procedures (Rheinwald (1980) Meth. Cell Bio., 21A:229). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Rheinwald (1980) Meth. Cell Bio., 21A:229; Pittelkow et al. (1986) Mayo Clinic. Proc., 61:771). If the ESCs are provided by a donor, a method for suppression of host versus graft reactivity (e.g., irradiation, drug or antibody administration to promote moderate immunosuppression) can also be used.

With respect to hematopoietic stem cells (HSC), any technique which provides for the isolation, propagation, and maintenance in vitro of HSC can be used in this embodiment of the invention. Techniques by which this may be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC may be used in conjunction with a method of suppressing transplantation immune reactions of the future host/patient. In a particular embodiment, human bone marrow cells can be obtained from the posterior iliac crest by needle aspiration (see, e.g., Kodo et al. (1984) J. Clin. Invest., 73:1377-1384). In one embodiment, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al. (1977) J. Cell Physiol., 91:335) or Witlock-Witte culture techniques (Witlock et al. (1982) Proc. Natl. Acad. Sci. U.S.A., 79:3608-3612).

Pharmaceutical Compositions and Administration

The invention further provides pharmaceutical compositions comprising an effective amount of an ERG or LTF therapeutic, including ERG or LTF nucleic acids (sense or antisense) or ERG or LTF polypeptides of the invention, in a pharmaceutically acceptable carrier, as described below.

Compositions comprising an effective amount of a polypeptide of the present invention, in combination with other components such as a physiologically acceptable diluent, carrier, or excipient, are provided herein. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in Remington's Pharmaceutical Sciences, 16$^{th}$ ed., Mack Publishing Company, Easton, Pa., 1980.

In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury. Sustained release from implants is also contemplated. One skilled in the art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

Compositions comprising nucleic acids of the invention in physiologically acceptable formulations, e.g., to be used for gene therapy are also contemplated. In one embodiment, the nucleic acid can be administered in vivo to promote expression of the encoded protein, by constructing it as part of an appropriate nucleic acid expression vector and administering it so that it becomes intracellular as described in other sections herein.

Various delivery systems are known in the art and can be used to administer a therapeutic of the invention. Examples include, but are not limited to encapsulation in liposomes, microparticles, microcapsules, recombinant cells capable of expressing the therapeutic, receptor-mediated endocytosis (see, e.g., Wu et al. (1987) J. Biol. Chem., 262:4429-4432), construction of a therapeutic nucleic acid as part of a retroviral or other vector, etc. Methods of introduction include, but are not limited to, intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, local infusion during surgery, topical application, e.g., in conjunction with a wound dressing after surgery, by injection, by means of a catheter, a suppository, an implant, wherein the said implant is of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the therapeutic can be delivered in a vesicle, in particular a liposome (see Langer (1990) Science, 249:1527-1533; Treat et al. (1989) in Liposomes in the Therapy of Infectious Disease and Cancer, Lopez-Berestein et al., eds., Liss, New York, pp. 353-365; Lopez-Berestein, ibid., pp. 317-327. In yet another embodiment, the therapeutic can be delivered in a controlled release system. In one embodiment, a pump may be used (see Langer, supra; Sefton (1987) CRC Crit. Ref. Biomed. Eng., 14:201; Buchwald et al. (1980) Surgery, 88:507; Saudek et al. (1989) New Engl. J. Med., 321:574). In another embodiment, polymeric materials can be used (see Medical Applications of Controlled Release, Langer et al., eds., CRC Pres., Boca Raton, Fla., 1974; Controlled Drug Bioavailability, Drug Product Design and Performance, Smolen et al., eds., Wiley, N.Y., 1984; Ranger et al. (1983) J. Macromol. Sci. Rev. Macromol. Chem., 23:61; see also Levy et al. (1985) Science, 228:190; During et al. (1989) Ann. Neurol., 25:351; Howard et al. (1989) J. Neurosurg., 71:105. In yet another embodiment, a controlled release system can be placed in proximity of the therapeutic target, i.e., the brain, thus requiring only a fraction of the systemic dose (see, e.g., Goodson (1984) in Medical Applications of Controlled Release, supra, vol. 2, pp. 115-138). Other controlled release systems are discussed in the review by Langer (1990, Science, 249:1527-1533).

Diagnosis and Screening

ERG, LTF, and/or AMACR proteins, analogues, derivatives, and fragments thereof, and antibodies thereto; ERG, LTF, DD3, and/or AMACR nucleic acids (and their complementary and homologous sequences) and antibodies thereto, including anti-ERG, anti-DD3, anti-LTF and/or anti-AMACR antibodies, have uses in diagnostics. Such molecules can be used in assays, such as immunoassays, to detect, prognose, diagnose, or monitor various conditions, diseases, and disorders affecting ERG, LTF, DD3, and/or AMACR expression, or monitor the treatment thereof, particularly cancer, and more particularly prostate cancer. In particular, such an immunoassay is carried out by a method comprising contacting a sample derived from an individual with an anti-ERG, anti-LTF, anti-DD3, and/or anti-AMACR antibody (directed against either a protein product or a nucliec acid) under conditions such that specific binding can occur, and detecting or measuring the amount of any specific binding by the antibody. In one embodiment, such binding of antibody, in tissue sections, can be used to detect aberrant ERG, LTF, DD3, and/or AMACR localization or aberrant (e.g., high, low or absent) levels of ERG, LTF, DD3, and/or AMACR. In a specific embodiment, antibody to ERG, LTF, DD3, and/or AMACR can be used to assay in a biological sample (e.g., tissue, blood, or urine sample) for the presence of ERG, LTF, DD3, and/or AMACR where an aberrant level of ERG, LTF, DD3, and/or AMACR is an indication of a diseased condition, such as cancer, including, for example, prostate cancer.

Any biological sample in which it is desired to detect an oligonucloetide or polypeptide of interest can be used, including tissue, cells, blood, lymph, semen, and urine. The biological sample is preferably derived from prostate tissue, blood, or urine. The tissue sample comprises cells obtained from a patient. The cells may be found in a prostate tissue sample collected, for example, by a prostate tissue biopsy or histology section, or a bone marrow biopsy. The blood sample can include whole blood, plasma, serum, or any derivative thereof, including, for example, circulating cells, such as prostate cells, isolated from the blood sample, or nucleic acid or protein obtained from the isolated cells. Blood may contain prostate cells, particularly when the prostate cells are cancerous, and, more particularly, when the prostate cancer metastasizes and is shed into the blood. Similarly, the urine sample can be whole urine or any derivative thereof, including, for example, cells, such as prostate cells, obtained from the urine.

The immunoassays which can be used include, but are not limited to, competitive and non-competitive assay systems using techniques such as Western blots, radioimmunoassays, ELISA, immunoprecipitation assays, immunodiffusion assays, agglutination assays, complement-fixation assays, immunoradiometric assays, fluorescent immunoassays, protein A immunoassays, to name but a few.

ERG, LTF, DD3, and/or AMACR genes and related nucleic acid sequences and subsequences, including complementary sequences, can also be used in hybridization assays. ERG, LTF, DD3, and/or AMACR nucleic acid sequences, or subsequences thereof comprising about at least 8, 15, 20, 50, 100, 250, or 500 nucleotides can be used as hybridization probes. Hybridization assays can be used to detect, prognose, diagnose, or monitor conditions, disorders, or disease states associated with aberrant changes in ERG, LTF, DD3, and/or AMACR expression and/or activity as described above. In particular, such a hybridization assay is carried out by a method comprising contacting a sample containing nucleic acid with a nucleic acid probe capable of hybridizing under defined conditions (preferably under high stringency hybridization conditions, e.g., hybridization for 48 hours at 65° C. in 6×SSC followed by a wash in 0.1×SSX at 50° C. for 45 minutes) to an ERG, LTF, DD3, and/or AMACR nucleic acid, and detecting (i.e, measuring either qualitatively or quantitatively) the degree of the resulting hybridization. As described herein, any nucleic acid amplification procedure, including, PCR/RT-PCR, TMA, NASBA, 3SR, LCR, SDA, and LAMP can be used to detect the presence of the ERG, LTF, DD3 and/or AMACR gene and/or the level of its mRNA expression.

In some applications, probes exhibiting at least some degree of self-complementarity are desirable to facilitate detection of probe:target duplexes in a test sample without first requiring the removal of unhybridized probe prior to detection. Molecular torch probes are a type of self-complementary probes that are disclosed by Becker et al., U.S. Pat. No. 6,361,945. The molecular torch probes disclosed Becker et al. have distinct regions of self-complementarity, referred to as "the target binding domain" and "the target closing domain," which are connected by a joining region and which hybridize to one another under predetermined hybridization assay conditions. When exposed to denaturing conditions, the complementary regions (which may be fully or partially complementary) of the molecular torch probe melt, leaving the target binding domain available for hybridization to a target sequence when the predetermined hybridization assay conditions are restored. And when exposed to strand displacement conditions, a portion of the target sequence binds to the target binding domain and displaces the target closing domain from the target binding domain. Molecular torch probes are designed so that the target binding domain favors hybridization to the target sequence over the target closing domain. The target binding domain and the target closing domain of a molecular torch probe include interacting labels (e.g., luminescent/quencher) positioned so that a different signal is produced when the molecular torch probe is self-hybridized as opposed to when the molecular torch probe is hybridized to a target nucleic acid, thereby permitting detection of probe:target duplexes in a test sample in the presence of unhybridized probe having a viable label or labels associated therewith.

Another example of detection probes having self-complementarity are the molecular beacon probes disclosed by Tyagi et al. in U.S. Pat. No. 5,925,517. Molecular beacon probes include nucleic acid molecules having a target complement sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complement sequence separates the members of the affinity pair, thereby shifting the probe to an open confirmation. The shift to the open confirmation is detectable due to reduced interaction of the label pair, which may be, for example, a fluorophore and quencher, such as DABCYL and EDANS.

By way of example, ERG, LTF, AMACR, or DD3 hybridization probes can comprise a nucleic acid having a contiguous stretch of at least about 8, 15, 20, 50, 100, 250, 500, 750, 1000, 1250, or 1500 contiguous nucleotides of SEQ ID NO:1, SEQ ID NO:2, SEQ ID NO:3, SEQ ID NO:4, or SEQ ID NO:5 or a sequence complementary thereto. Such contiguous fragments of SEQ ID NO:1, SEQ ID NO:2, SEQ ID NO:3, SEQ ID NO:4, or SEQ ID NO:5 may also contain at least one mutation so long as the mutant sequence retains the capacity to hybridize to SEQ ID NO:1, SEQ ID NO:2, SEQ ID NO: 3, SEQ ID NO:4, or SEQ ID NO:5 under low or high stringency conditions (preferably under high stringency hybridization conditions, e.g., hybridization for 48 hours at 65° C. in 6×SSC followed by a wash in 0.1×SSX at 50° C. for 45 minutes).

In specific embodiments, diseases and disorders involving hyperproliferation of cells, such as cancers, including, for example, prostate cancer, can be diagnosed, or their suspected presence can be screened for, or a predisposition to develop such disorders can be predicted, by detecting levels of the ERG, LTF, and/or AMACR protein, ERG, DD3, and/or AMACR RNA, or ERG, DD3, and/or AMACR functional activity, or by detecting mutations in ERG, DD3, LTF and/or AMACR RNA, DNA, or protein (e.g., translocations in ERG, LFT, DD3, or AMACR nucleic acids, truncations in the ERG, LFT, DD3, or AMACR gene or protein, changes in nucleotide or amino acid sequence relative to wild-type ERG, LTF, DD3, or AMACR) that cause increased or decreased expression or activity of ERG, LTF, DD3, and/or AMACR. By way of example, levels of ERG, LTF, and/or AMACR protein can be detected by immunoassay, levels of ERG, LTF, DD3, and/or AMACR mRNA can be detected by hybridization assays (e.g., Northern blots, dot blots, or any nucleic acid amplification procedure, including, PCR/RT-PCR, TMA, NASBA, 3SR, LCR, SDA, and LAMP), translocations and point mutations in ERG, LTF, DD3, and/or AMACR nucleic acids can be detected by Southern blotting, RFLP analysis, any nucleic acid amplification procedure, including, PCR/RT-PCR, TMA, NASBA, 3SR, LCR, SDA, LAMP, sequencing of the ERG, LTF, DD3, and/or AMACR genomic DNA or cDNA obtained from the patient, etc.

In one embodiment, levels of the ERG, DD3, LTF and/or AMACR mRNA or protein in a subject sample are detected or measured and compared to the mRNA or protein expression levels of the corresponding gene in a control sample or to a standard numerical value or range. For example, increased expression levels of ERG, DD3, and/or AMACR or decreased levels of LTF, relative to a matched, normal tissue sample, indicate that the subject has a malignancy or hyperproliferative disorder, including, for example, prostate cancer, or a predisposition to develop the same. Other appropriate controls include other noncancerous samples from the subject, samples obtained from a different subject without cancer, or other cancer-specific markers. For example, in prostate cancer, a prostate-cell specific marker, such as PSA, can be used as a control to compare and/or normalize expression levels of other genes, such as ERG, LTF, DD3, and/or AMACR. In one embodiment, a method of diagnosing cancer, such as prostate cancer, comprises obtaining a biological sample from a subject (e.g., a tissue sample (e.g., from biopsy tissue), a blood sample, or a urine sample), determining the expression level of a ERG, LTF, DD3, and/or AMACR gene and/or ERG, LTF, DD3, and/or AMACR activity in the samples, and diagnosing or prognosing cancer in said subject. In further embodiments, the expression level of the ERG, LTF, DD3, and/or AMACR gene and/or ERG, LTF, DD3, and/or AMACR activity is determined by Southern blotting, Northern blotting, Western blotting, ELISA, any nucleic acid amplification procedure, including, PCR/RT-PCR, TMA, NASBA, 3SR, LCR, SDA, and LAMP, or other techniques as described herein or known in the art. Without limiting the instant invention, increased or decreased expression of at least two times, as compared to the control sample indicates the presence of prostate cancer or a higher predisposition to developing prostate cancer.

Another aspect of the invention provides a means for monitoring a response to "hormonal therapy" by evaluating the expression profiles of the ERG gene, alone or in combination with the AMACR and/or DD3 genes and/or LTF genes, and correlating these profiles with the clinical signs of the disease.

Kits for diagnostic use are also provided. A kit comprises an anti-ERG gene antibody or an antibody directed against the ERG protein and/or an anti-AMACR gene antibody or an antibody directed against the AMACR protein and/or an anti-DD3 gene antibody and/or and an anti-LTF gene antibody or an antibody directed against the LTF protein, which can be optionally detectably labeled. A kit is also provided that comprises a nucleic acid probe capable of hybridizing under defined conditions (preferably under high stringency hybridization conditions, e.g., hybridization for 48 hours at 65° C. in 6×SSC followed by a wash in 0.1×SSX at 50° C. for 45 minutes) to ERG, LTF, DD3, and/or AMACR nucleic acid. In a specific embodiment, a kit comprises at least a pair of primers (e.g., each in the size range of at least about 6, 17, 30, or 60 nucleotides) that are capable of priming amplification, by any nucleic acid amplification procedure (including e.g., PCR/RT-PCR, TMA, NASBA, 3SR, LCR, SDA, LAMP), of the ERG, LTF, DD3, and/or AMACR gene or a fragment thereof. A kit can comprise a predetermined amount of a purified ERG, LTF, DD3, and/or AMACR protein or nucleic acid for use, e.g., as a standard or control. The kit can also comprise one or more components for detecting the nucleic acid probe, including components described herein or known in the art.

In one embodiment, the kit comprises a nucleic acid that hybridizes under defined conditions (and preferably under conditions of high stringency, e.g., hybridization for 48 hours at 65° C. in 6×SSC followed by a wash in 0.1×SSX at 50° C. for 45 minutes) with at least one gene chosen from those genes identified in Tables 1-6 or the DD3 gene, and is affixed to a support, alone, or in combination with other nucleic acids. For example, an ERG and/or LTF nucleic acid can be affixed to the support, with or without other nucleic acids. In a specific embodiment, the support comprises at least an ERG nucleic acid and an AMACR nucleic acid or at least an ERG nucleic acid and a DD3 nucleic acid. In another embodiment, the support comprises at least an ERG nucleic acid, an AMACR nucleic acid, and a DD3 nucleic acid. This support can be used as part of a kit for detecting cancer, such as prostate cancer. These kits can further comprise at least a pair of primers (e.g., each in the size range of at least about 6, 17, 30, or 60 nucleotides) that are capable of priming amplification, by any nucleic acid amplification procedure (including e.g., PCR/RT-PCR, TMA, NASBA, 3SR, LCR, SDA, LAMP), of the ERG, LTF, DD3, and/or AMACR gene or a fragment thereof.

EXAMPLES

Example 1

Screening of CaP Cell-Specific Gene Expression Signatures Using Affymetrix GeneChip Patient Selection Specimens were obtained under an IRB-approved protocol from patients treated by radical prostatectomy (RP) at Walter Reed Army Medical Center (WRAMC). From over 300 patients two groups were selected which had prostate tumors with either moderate (MR) or high risk (HR) of disease progression after RP. The HR group had PSA recurrence, Gleason score 8-9, T3c stage, seminal vesicle invasion, and poorly differentiated tumor cells; the MR group had no PSA recurrence, Gleason score 6-7, T2a-T3b stage, no seminal vesicle invasion, and well to moderately differentiated tumor cells. LCM compatible specimens were selected from age and race matched HR or MR patients with no family history of CaP.

Tissue Samples and Laser-Capture Microdissection

Normal and cancer cells were laser capture microdissected (LCM) from OCT embedded and Hematoxylin-eosin (H&E) stained frozen prostate sections of radical prostatectomy specimens (2000 laser shots for one sample). Laser capture microdissection (LCM) facilitates the isolation of morphologically defined, homogenous cell populations from complex tissues by selectively adhering the cells of interest to a transparent film with focused pulses of low energy infrared laser under a microscope. Emmert-Buck et al., Science (1996); 274(5289): 921-922; Schutz et al., Nat Biotechnol (1998) 16(8): 737-742.

RNA Extraction and T7-Based Linear RNA Amplification

Total RNA was isolated from the LCM samples with the MicroRNA kit (Stratagene, La Jolla, Calif.), quantified using RiboGreen dye (Molecular Probes, Eugene, Oreg.) and VersaFluor fluorimeter (BioRad, Hercules, Calif.), and quality tested by RT-PCR using NKX3.1 and GAPDH primers. Linear RNA amplification was performed using RiboAmp RNA amplification kit (Arcturus, Mountain View, Calif.). Precisely, 2 nanograms of total RNA from LCM derived epithelial cells of normal as well as tumor tissue from each patient was used for the first round of amplification. During the second round of amplification after cDNA synthesis and purification the samples were biotinylated during in vitro transcription which was used for the GeneChip analysis.

Gene Chip Analysis

Linearly amplified aRNA was hybridized to high-density oligonucleotide human genome array (HG U133A array) (Affymetrix, Santa Clara, Calif., USA). The array contains 22,283 probe sets, about 18,000 of which represent well annotated genes, while the remainder represent various expressed sequence tags (EST) and hypothetical genes. Biotinylation was carried out using aRNA by in vitro transcription using MEGA script T7 in vitro Transcription Kit (Ambion, Austin, Tex., USA) cDNA and biotinylated UTP and biotinylated CTP (ENZO, Farmingdale, N.Y., USA) (34). The biotin labeled cRNA was purified using the QIAGEN RNeasy spin columns (QIAGEN, Valencia, Calif.) following the manufacturer's protocol. The biotin labeled cRNA was fragmented in a 40 µl reaction mixture containing 40 mM Tris-acetate, pH 8.1, 100 mM potassium acetate, and 30 mM magnesium acetate incubated at 94° C. for 35 minutes and then put on ice.

Hybridization, Staining and Scanning of the GeneChip

The biotin labeled and fragmented aRNA was hybridized to the HG U133A array. Briefly, a 220 µl hybridization solution consisting of: 1M NaCl, 10 mM Tris pH 7.6, 0.005% Triton X-100, 50 pM control Oligo B2 (5' bioGT-CAAGATGCTACCGTTCAG 3') (SEQ ID NO:6) (Affymetrix); the control cRNA cocktail of: Bio B (150 pM), Bio C (500 pM), Bio D (2.5 nM) and Cre X (10 nM) (American Type Tissue Collection, Manassas, Va. and Lofstrand Labs, Gaithersburg, Md.), 0.1 mg/ml herring sperm DNA and 0.05 µg/µl of the fragmented labeled sample cRNA was heated to 95° C. for 35 min., cooled to 40° C. and clarified by centrifugation. Hybridization was at 42° C. in a rotisserie hybridization oven (Model 320, Affymetrix) at 60 rpm for 16 hours. Following hybridization, the GeneChip arrays were washed 10 times at 25° C. with 6×SSPE-T buffer (1 M NaCl, 0.006 M EDTA, and 0.06 M $Na_3PO_4$, 0.005% Triton X-100, pH 7.6) using the automated fluidics station protocol. GeneChip arrays were incubated at 50° C. in 0.5×SSPE-T, 0.005% Triton X-100 for 20 minutes at 60 rpm in the rotisserie oven. GeneChip arrays were stained for 15 minutes at room temperature and at 60 rpm, with streptavidin phycoerythrin (Molecular Probes, Inc., Eugene, Oreg.) stain solution at a final concentration of 10 µg/ml in 6×SSPE-T buffer and 1.0 mg/ml acetylated bovine serum albumin (Sigma). GeneChip arrays were washed twice at room temperature with 6×SSPE-T buffer, and then were scanned with the HP GeneArray Scanner (Hewlett-Packard, Santa Clara, Calif.) controlled by GeneChip 3.1 Software (Affymetrix).

Example 2

Analysis of GeneChip Results by Supervised Multi-Dimensional Scaling (MDS)

Image Analysis and Data Collection

Affymetrix GeneChip Microarray Analysis Software, version 3.1 and Affymetrix Micro DB and Data Mining Tool version 2.0 (Affymetrix), Microsoft Excel 2000 (Microsoft, Seattle, Wash.) and Statistica version 4.1 (Stat Soft, Inc., Tulsa, Okla.) were used. In the Affymetrix system, the average difference fluorescence is the average of the difference between every perfect match probe cell and its control mismatch probe cell and is directly related to the level of expression of a transcript. A comparative file indicates the relative change in abundance (fold change) for each transcript between a baseline and an experimental sample. For further detail and advanced bioinformatic analysis we used the Microarray Data Analysis software from NHGRI and the GeneSpring software (Silicon Genetics, Calif.).

Data Analysis

For clustering analysis, National Human Genome Research Institute (NHGRI) Microarray Data Analysis software was used, which partitioned the samples of the high risk and moderate risk groups into well-separated and homogeneous groups based on the statistical behavior of their genes expression. To achieve the objective of clustering each of the groups, all pair-wise similarities between samples were evaluated, and then grouped via the average linkage algorithm. Pearson correlation coefficient or Euclidean distance were typically used to quantify the similarity. Unsupervised hierarchical and or non hierarchical clustering was also performed using the same distance matrix.

Using a matrix of Euclidean distance measurements from complete pair wise comparison of all the prostate specimens, a multidimensional scaling (MDS) method was performed using an implementation of MDS in the MATLAB package to determine the overall similarities and dissimilarities in gene expression profiles. A weighted gene analysis was performed to generate a subset of genes statistically significant in separating the high risk group from the moderate risk group.

Briefly, for two different groups e.g., epithelium of high risk tumor and epithelium of moderate risk tumor with a given number of samples 25 and 25, the discriminative weight for each gene is determined by the formula: $w=d_B/(k_1 d_{w1}+k_2 d_{w2}+\alpha)$; where $d_B$ is the Euclidean distance between two groups (center-to-center or between cluster Euclidean distance), $d_{w1}$ is the average Euclidean distance among all the epithelial samples of high risk group, $d_{w2}$ is average Euclidean distance among all the epithelial samples of moderate risk group, $k_1=25/(25+25)$, $k_2=25/(25+25)$, and $\alpha$ is a small constant to ensure the denominator is never equal to zero. Genes were ranked according to their w values. Genes with high w values created greater separation between groups and denser compaction within the group. In other words, the subset of genes with high w values have the most discriminative power to differentiate a high risk group from a moderate risk group and vice versa. Sample labels were randomly permuted and the w value was computed again for each gene to test the statistical significance of the discriminative weights. Genes with the most significant expression differences were selected by p-values. A hierarchical clustering algorithm was used to verify the predictor model obtained from the supervised MDS analysis.

From this analysis, specific genes were identified whose expression signature in tumor tissue varied from their expression signature in benign matched tissue. Genes with a p-value of not more than 0.05 were selected and ranked by p-value, as shown in Tables 1-6.

In Silico Validation:

We have tested the discriminatory potential of the genes that we obtained from our analysis on some independent data sets. Affymetrix oligonucleotide GeneChip Hum95Av2 data were obtained from Welsh et al. 2001, Singh et al. Genes from these data bases that correspond with the genes of our discriminatory list were selected and their tumor specific expression intensities and/or tumor over normal ratio were used for an MDS analysis as described above in the data analysis section. MDS plots were obtained depicting the discriminatory capability of the genes on the independent data sets.

TABLE 1

The first 50 genes obtained from the supervised MDS analysis of tumor versus benign tissues of all the high risk and moderate risk CaP patients, ranked by p-value. (T vs B in All 18 Samples)

| No. | GenBank Accession | Common Name of Genes | Description of Genes | Map | p-Value | Expression Regulation Tumor | Benign |
|---|---|---|---|---|---|---|---|
| 1. | AF047020 | AMACR | Alpha-methylacyl-CoA racemase | 5p13.2-q11.1 | 0 | Up | Down |
| 2. | NM_002343 | LTF | Lactotransferrin | 3q21-q23 | 0 | Down | Up |
| 3. | NM_002275 | KRT15 | Keratin 15 | 17q21 | 0.000001 | Down | Up |
| 4. | BC000915 | CLIM1, CLP36, CLP-36 | PDZ and LIM domain 1 (elfin) | 10q22-q26.3 | 0.000001 | Down | Up |
| 5. | X90579 | CYP3A5 | Cytochrome P450, subfamily 3A, polypeptide 5 | 7 | 0.000001 | Down | Up |
| 6. | NM_003671 | CDC14B1, CDC14B2 | H. sapiens CDC14 cell division cycle 14 homolog B | 9q22.2-q22.31 | 0.000005 | Down | Up |
| 7. | AI424243 | CEGP1 | H. sapiens cDNA clone IMAGE: 2094442 | 11 | 0.000005 | Down | Up |
| 8. | NM_022370 | Rbig1 | Hypothetical protein FLJ21044 similar to Rbig1 | 11q24.2 | 0.000009 | Down | Up |
| 9. | AI356398 | ZFP36L2 | TISD_HUMAN P47974 TIS11D PROTEIN | 2 | 0.000018 | Down | Up |
| 10. | NM_005213 | STF1, STFA | Cystatin A (stefin A) | 3q21 | 0.000018 | Down | Up |
| 11. | NM_006394 | RIG | Regulated in glioma | 11p15.1 | 0.000018 | Down | Up |
| 12. | AF275945 | EVA1 | Epithelial V-like antigen 1 | 11q23.3 | 0.000018 | Down | Up |
| 13. | NM_020186 | DC11 | DC11 protein | 7q21.3 | 0.000018 | Up | Down |
| 14. | AI922538 | TMEM1 | Transmembrane protein 1 | 21 | 0.000018 | Down | Up |
| 15. | NM_014863 | BRAG, KIAA0598 | B cell RAG associated protein | 10q26 | 0.000018 | Down | Up |
| 16. | AI669229 | RARRES1 | Homo sapiens cDNA clone IMAGE: 2315074 | 3q25.33 | 0.000036 | Down | Up |
| 17. | NM_006017 | AC133, CD133 | Prominin (mouse)-like 1 | 4p15.33 | 0.000036 | Down | Up |
| 18. | NM_004503 | HOXC6 | Homeo box C6 | 12q12-q13 | 0.000036 | Up | Down |
| 19. | NM_005084 | PAFAH, LDL-PLA2 | Phospholipase A2, group VII | 6p21.2-p12 | 0.000036 | Up | Down |
| 20. | NM_001511 | MGSA, CXCL1, SCYB1 | GRO1 oncogene | 4q21 | 0.000071 | Down | Up |
| 21. | BG054844 | ARHE | H. sapiens cDNA clone IMAGE: 3441573 | 2q23.3 | 0.000071 | Down | Up |
| 22. | NM_007191 | WIF-1 | Wnt inhibitory factor-1 | 12q14.2 | 0.000071 | Down | Up |
| 23. | X99268 | TWIST | Twist (Drosophila) homolog | 7p21.2 | 0.000071 | Up | Down |
| 24. | AI826799 | EFEMP1 | EXTRACELLULAR PROTEIN S1-5 PRECURSOR | 2p16 | 0.000071 | Down | Up |
| 25. | NM_001018 | RPS15 | Ribosomal protein S15 | 19p13.3 | 0.000071 | Up | Down |
| 26. | AV711904 | LYZ | Lysozyme (renal amyloidosis) | | 0.000071 | Down | Up |
| 27. | AI433463 | MME | NEPRILYSIN (HUMAN) | 3q25.1-q25.2 | 0.000071 | Down | Up |
| 28. | BE908217 | ANXA2 | H. sapiens cDNA clone IMAGE: 3902323 | 15q21-q22 | 0.000071 | Down | Up |
| 29. | NM_000441 | PDS, DFNB4 | Solute carrier family 26, member 4 | 7q31 | 0.000071 | Down | Up |
| 30. | BC003068 | SLC19A1 | Solute carrier family 19, member 1 | 21q22.3 | 0.000071 | Up | Down |
| 31. | NM_005950 | MT1 | Metallothionein 1G | 16q13 | 0.000071 | Down | Up |
| 32. | NM_013281 | FLRT3 | Fibronectin leucine rich transmembrane protein 3 | 20p11 | 0.000071 | Down | Up |
| 33. | AI351043 | ESTs | H. sapiens cDNA clone IMAGE: 1948310 | 21 | 0.000145 | Up | Down |
| 34. | NM_001099 | PAP | Acid phosphatase, prostate | 3q21-q23 | 0.000145 | Down | Up |
| 35. | NM_006113 | VAV3 | Vav 3 oncogene | 1p13.1 | 0.000145 | Down | Up |
| 36. | NM_005980 | S100P | S100 calcium-binding protein P | 4p16 | 0.000145 | Down | Up |
| 37. | NM_000165 | GJA1 | Gap junction protein, alpha 1, 43 kD (connexin 43) | 6q21-q23.2 | 0.000145 | Down | Up |
| 38. | NM_003897 | DIF2, IEX1, PRG1 | Immediate early response 3 | 6p21.3 | 0.000145 | Down | Up |

TABLE 1-continued

The first 50 genes obtained from the supervised MDS analysis of tumor versus benign tissues of all the high risk and moderate risk CaP patients, ranked by p-value. (T vs B in All 18 Samples)

| No. | GenBank Accession | Common Name of Genes | Description of Genes | Map | p-Value | Expression Regulation Tumor | Expression Regulation Benign |
|---|---|---|---|---|---|---|---|
| 39. | BC001388 | ANX2, LIP2, CAL1H | Annexin A2 | 15q21-q22 | 0.000145 | Down | Up |
| 40. | BC003070 | HDR, MGC5445 | GATA-binding protein 3 | 10p15 | 0.000145 | Down | Up |
| 41. | NM_020139 | LOC56898 | Oxidoreductase UCPA | 4 | 0.000145 | Down | Up |
| 42. | AK002207 | KIAA0610 | KIAA0610 protein | 13 | 0.000145 | Down | Up |
| 43. | NM_000574 | CR, TC, CD55 | Decay accelerating factor for complement | 1q32 | 0.000145 | Down | Up |
| 44. | NM_006926 | SP-A2, COLEC5 | Surfactant, pulmonary-associated protein A2 | 10q22-q23 | 0.000145 | Up | Down |
| 45. | U37546 | API2, MIHC, CIAP2 | Baculoviral IAP repeat-containing 3 | 11q22 | 0.000145 | Down | Up |
| 46. | AU148057 | DKK3 | *H. sapiens* cDNA clone MAMMA1002489 | 11pter-p15.5 | 0.000145 | Down | Up |
| 47. | NM_002600 | DPDE4, PDEIVB | Phosphodiesterase 4B, cAMP-specific | 1p31 | 0.000145 | Down | Up |
| 48. | S59049 | BL34, IER1, IR20 | Regulator of G-protein signalling 1 | 1q31 | 0.0003 | Down | Up |
| 49. | NM_001275 | CGA, CgA | Chromogranin A (parathyroid secretory protein 1) | 14q32 | 0.0003 | Down | Up |
| 50. | AL575509 | ETS2 | *H. sapiens* cDNA clone CS0DI059YP21 = | 21q22.2 | 0.0003 | Down | Up |

TABLE 2

The first 50 genes from the supervised MDS analysis of tumor over benign (T/B) tissues ratio (Fold Change) of the high risk versus moderate risk CaP patients, ranked by p-value.: (T/B Fold Change in HR vs MR)

| No | Genbank accession | Common Name of Genes | Description of Genes | Map | p-Value |
|---|---|---|---|---|---|
| 1. | NM_004522 | KINN, NKHC, NKHC2, NKHC-2 | Kinesin family member 5C | 2q23.3 | 0.00011 |
| 2. | J03198 | GNAI3 | Guanine nucleotide binding protein G (K), alpha subunit | 1p13 | 0.000981 |
| 3. | NM_018010 | HIPPI, FLJ10147 | Hypothetical protein FLJ10147 | 3q13.13 | 0.003257 |
| 4. | NM_005479 | FRAT1 | Frequently rearranged in advanced T-cell lymphomas | 10q23.33 | 0.004964 |
| 5. | NM_021795 | SAP1 | ELK4, ETS-domain protein (SRF accessory protein 1) | 1q32 | 0.004964 |
| 6. | NM_003113 | LEU5, RFP2 | Nuclear antigen Sp100 | 2q37.1 | 0.004964 |
| 7. | NM_002053 | GBP1 | Guanylate binding protein 1, interferon-inducible, 67 kD | 1p22.1 | 0.004964 |
| 8. | AF064092 | GSA, GSP, GPSA, GNAS1, | Guanine nucleotide regulatory protein | 20q13.2-q13.3 | 0.007579 |
| 9. | BC003070 | HDR, MGC5445 | GATA-binding protein 3 | 10p15 | 0.007579 |
| 10. | NM_012245 | SKIP, NCOA-62 | SKI-interacting protein | 14q24.3 | 0.007579 |
| 11. | NM_015895 | LOC51053 | Geminin | 6p22.2 | 0.007579 |
| 12. | AA083478 | TRIM22 | Stimulated trans-acting factor (50 kDa) | 11 | 0.007579 |
| 13. | NM_000100 | PME, CST6, EPM1, STFB | Cystatin B (stefin B) | 21q22.3 | 0.007579 |
| 14. | NM_003031 | SIAH1 | Seven in absentia (*Drosophila*) homolog 1 | 16q12 | 0.007579 |
| 15. | NM_003407 | TTP, GOS24, TIS11, NUP475 | Zinc finger protein 36, C3H type, homolog (mouse) | 19q13.1 | 0.007579 |
| 16. | BF979419 | ESTs | ESTs, Highly similar to 60S ribosomal protein 13A [*H. sapiens*] | 19q13.33 | 0.007579 |
| 17. | NM_021038 | MBNL | Muscleblind (*Drosophila*)-like | 3q25 | 0.007579 |
| 18. | NM_014454 | PA26 | P53 regulated PA26 nuclear protein | 6q21 | 0.007579 |
| 19. | BC004399 | DEME-6 | DEME-6 protein | 1p32.3 | 0.007579 |
| 20. | NM_018490 | LGR4 | G protein-coupled receptor 48 | 11p14-p13 | 0.007579 |
| 21. | NM_004328 | BCS, BCS1, h-BCS, Hs.6719 | BCS1 (yeast homolog)-like | 2q33 | 0.007579 |
| 22. | D87445 | KIAA0256 | KIAA0256 gene product | 15 | 0.007579 |
| 23. | NM_006326 | NIFIE14 | *Homo sapiens* seven transmembrane domain protein, mRNA | 19q13.12 | 0.007579 |
| 24. | D83077 | TTC3 | Tetratricopeptide repeat domain 3 | Xq13.1 | 0.007579 |
| 25. | NM_006732 | GOS3 | FBJ murine osteosarcoma viral oncogene homolog B | 19q13.32 | 0.007579 |
| 26. | NM_003760 | EIF4G3 | Eukaryotic translation initiation factor 4 gamma, 3 | 1pter-p36.13 | 0.007579 |
| 27. | NM_004905 | AOP2 | Anti-oxidant protein 2 | 1q24.1 | 0.01159 |
| 28. | NM_018439 | IMPACT | Hypothetical protein IMPACT | 18 | 0.01159 |
| 29. | BC000629 | DARS | Aspartyl-tRNA synthetase | 2q21.2 | 0.01159 |
| 30. | AK002064 | DKFZP564A2416 | DKFZP564A2416 protein | 2 | 0.01159 |
| 31. | NM_013387 | HSPC051 | Ubiquinol-cytochrome c reductase complex (7.2 kD) | 22 | 0.01159 |
| 32. | AA135522 | KIAA0089 | *Homo sapiens* KIAA0089 mRNA sequence. | 3 | 0.01159 |
| 33. | NM_015545 | KIAA0632 | KIAA0632 protein | 7q22.1 | 0.01159 |
| 34. | NM_005767 | P2Y5 | Purinergic receptor (family A group 5) | 13q14 | 0.01159 |
| 35. | BC003682 | G25K, CDC42Hs | Cell division cycle 42 (GTP-binding protein, 25 kD) | 1p36.1 | 0.01159 |
| 36. | NM_005053 | RAD23A | RAD23 (*S. cerevisiae*) homolog A | 19p13.2 | 0.017805 |
| 37. | AI672541 | IPW | Human non-translated mRNA sequence. | 15q11-q12 | 0.017805 |
| 38. | AK023938 | *H. sapiens* cDNA FLJ13876 clone | SELECTED MODEL ORGANISM PROTEIN SIMILARITIES | 2q37.3 | 0.017805 |
| 39. | NM_000062 | C1IN, C1NH, C1-INH | Serine (or cysteine) proteinase inhibitor, clade G (C1 inhibitor) | 11q12-q13.1 | 0.017805 |
| 40. | AA576961 | PHLDA1 | Pleckstrin homology-like domain, family A, member 1 | 12q15 | 0.017805 |

TABLE 2-continued

The first 50 genes from the supervised MDS analysis of tumor over benign (T/B) tissues ratio (Fold Change) of the high risk versus moderate risk CaP patients, ranked by p-value.: (T/B Fold Change in HR vs MR)

| No | Genbank accession | Common Name of Genes | Description of Genes | Map | p-Value |
|---|---|---|---|---|---|
| 41. | AI796269 | NBS1, ATV, NIBRIN | *H. sapiens* cDNA similar to Cell Cycle Regulatory Protein P95. | 8q21-q24 | 0.017805 |
| 42. | NM_000016 | ACADM | Acyl-Coenzyme A dehydrogenase, C-4 to C-12 straight chain | 1p31 | 0.017805 |
| 43. | AI867102 | KIAA0906, NUP210, gp210 | Nuclear pore membrane glycoprotein 210 | 3p25.2-p25.1 | 0.017805 |
| 44. | AI263909 | ARHB, RHOB, RHOH6 | Oncogene RHO6; Aplysia RAS-related homolog 6 | 2pter-p12 | 0.017805 |
| 45. | NM_016021 | NCUBE1 | Non-canonical ubquitin conjugating enzyme 1 | 6 | 0.017805 |
| 46. | NM_012192 | TIM9B, TIM10B | Fracture callus 1 (rat) homolog | 11p15.5-p15.3 | 0.017805 |
| 47. | NM_025087 | FLJ21511 | Hypothetical protein FLJ21511 | 4 | 0.017805 |
| 48. | NM_014959 | CARD8, CARDINAL, KIAA0955 | Tumor up-regulated CARD-containing antagonist of caspase 9 | 19q13.33 | 0.017805 |
| 49. | AA923354 | MAOA | Monoamine oxidase A. | Xp11.4-p11.3 | 0.017805 |
| 50. | NM_021964 | ZNF148 | Zinc finger protein 148 (pHZ-52) | 3q21 | 0.017805 |
| 51. | NM_001674 | ATF3 | Activating transcription factor 3 | 1q32.3 | 0.017805 |

TABLE 3

The first 50 genes obtained from the supervised MDS analysis of tumor versus benign tissues of all the high risk CaP patients, ranked by p-value. (T vs N Intensities of 9 HR)

| No. | GenBank Accession | Common Name of Genes | Description of Genes | Map | p-Value | Expression Regulation Tumor | Benign |
|---|---|---|---|---|---|---|---|
| 1. | U65585 | HLA-DR1B | Major histocompatibility complex, class II, DR beta 1 | 6p21.3 | 0.00002 | Down | Up |
| 2. | NM_002053 | GBP1 | Guanylate binding protein 1, interferon-inducible, | 1p22.1 | 0.000076 | Down | Up |
| 3. | NM_021983 | HLA-DRB4 | Major histocompatibility complex, class II, DR beta 4 | 6 | 0.000076 | Down | Up |
| 4. | AI424243 | CEGP1 | *Homo sapiens* cDNA clone IMAGE: 2094442 | 11 | 0.000102 | Down | Up |
| 5. | NM_002343 | LTF | Lactotransferrin | 3q21-q23 | 0.000138 | Down | Up |
| 6. | NM_014575 | SCHIP-1 | Schwannomin-interacting protein 1 | 3q26.1 | 0.000257 | Down | Up |
| 7. | BC001169 | ESD | Esterase D/formylglutathione hydrolase | 13q14.1-q14.2 | 0.000357 | Up | Down |
| 8. | BF970427 | UGCG | UDP-glucose ceramide glucosyltransferase | 9 | 0.000357 | Down | Up |
| 9. | NM_002275 | KRT15 | Keratin 15 | 17q21 | 0.000495 | Down | Up |
| 10. | AU148057 | DKK3 | *H. sapiens* cDNA clone MAMMA1002489 | 11pter-p15.5 | 0.000495 | Down | Up |
| 11. | AI922538 | TMEM1 | Transmembrane protein 1 | 21 | 0.000689 | Down | Up |
| 12. | NM_004481 | GALNAC-T2 | UDP-GalNAc transferase 2 | 1q41-q42 | 0.000689 | Down | Up |
| 13. | BC003070 | HDR, MGC5445 | GATA-binding protein 3 | 10p15 | 0.00097 | Down | Up |
| 14. | BF979419 | ESTs, similar to RPL13A | *H. sapiens* 60S Ribosomal protein L13A | | 0.00097 | Up | Down |
| 15. | BG054844 | ARHE | *H. sapiens* cDNA clone IMAGE: 3441573 | 2q23.3 | 0.00097 | Down | Up |
| 16. | L42024 | HLA-B | Major histocompatibility complex, class I, B | 6p21.3 | 0.00138 | Down | Up |
| 17. | AL545982 | CCT2 | *H. sapiens* cDNA clone CS0DI023YD15 | 12q15 | 0.001992 | Up | Down |
| 18. | NM_001993 | TF, TFA, CD142 | Coagulation factor III (thromboplastin, tissue factor) | 1p22-p21 | 0.001992 | Up | Down |
| 19. | NM_004198 | CHRNA6 | Cholinergic receptor, nicotinic, alpha polypeptide 6 | 8p11.1 | 0.001992 | Down | Up |
| 20. | AV711904 | LYZ | Lysozyme (renal amyloidosis) | 12q15 | 0.001992 | Down | Up |
| 21. | NM_013387 | HSPC051 | Ubiquinol-cytochrome c reductase complex (7.2 kD) | 22 | 0.001992 | Up | Down |
| 22. | AW514210 | HLA-F | HLA CLASS I HISTOCOMPATIBILITY ANTIGEN, F A | 6p21.3 | 0.001992 | Down | Up |
| 23. | NM_005032 | PLS3 | Plastin 3 (T isoform) | Xq24 | 0.002894 | Down | Up |
| 24. | NM_003407 | TTP, GOS24, NUP475 | Zinc finger protein 36, C3H type, homolog (mouse) | 19q13.1 | 0.002894 | Down | Up |
| 25. | NM_000165 | GJA1 | Gap junction protein, alpha 1, 43 kD (connexin 43) | 6q21-q23.2 | 0.002894 | Down | Up |
| 26. | AF275945 | EVA1 | Epithelial V-like antigen 1 | 11q23.3 | 0.002894 | Down | Up |
| 27. | NM_002450 | MT1L | Metallothionein 1L | 16q13 | 0.002894 | Down | Up |
| 28. | NM_005950 | MT1 | Metallothionein 1G | 16q13 | 0.002894 | Down | Up |
| 29. | NM_006994 | BTN3A3 | Butyrophilin, subfamily 3, member A3 | 6p21.33 | 0.002894 | Down | Up |
| 30. | AI049962 | KIAA0191 | *H. sapiens* cDNA clone IMAGE: 1700970 | 1 | 0.002894 | Down | Up |
| 31. | X99268 | TWIST | Twist (*Drosophila*) homolog | 7p21.2 | 0.002894 | Up | Down |
| 32. | NM_016021 | NCUBE1 | Non-canonical ubquitin conjugating enzyme 1 | 6 | 0.002894 | Up | Down |
| 33. | NM_016205 | SCDGF | Platelet derived growth factor C | 4q32 | 0.002894 | Up | Down |
| 34. | AI681120 | RANBP2 | *H. sapiens* cDNA clone IMAGE: 2272403 | 2q11-q13 | 0.002894 | Up | Down |
| 35. | NM_000574 | CR, TC, CD55 | Decay accelerating factor for complement | 1q32 | 0.004205 | Down | Up |
| 36. | NM_014937 | KIAA0966 | Sac domain-containing inositol phosphatase 2 | 10q26.13 | 0.004205 | Down | Up |
| 37. | NM_005213 | STF1, STFA | Cystatin A (stefin A) | 3q21 | 0.004205 | Down | Up |
| 38. | NM_005952 | MT1 | Metallothionein 1X | 16q13 | 0.004205 | Down | Up |
| 39. | AF130095 | FN1 | Fibronectin 1 | 2q34 | 0.004205 | Down | Up |

TABLE 3-continued

The first 50 genes obtained from the supervised MDS analysis of tumor versus benign tissues of all the high risk CaP patients, ranked by p-value. (T vs N Intensities of 9 HR)

| No. | GenBank Accession | Common Name of Genes | Description of Genes | Map | p-Value | Expression Regulation Tumor | Benign |
|---|---|---|---|---|---|---|---|
| 40. | BE568219 | PDE8A | *H. sapiens* cDNA clone IMAGE: 3683966 | 15q25.1 | 0.004205 | Up | Down |
| 41. | D50925 | STK37, PASKIN, | PAS-serine/threonine kinase | 2q37.3 | 0.004205 | Down | Up |
| 42. | NM_006113 | VAV3 | Vav 3 oncogene | 1p13.1 | 0.004205 | Down | Up |
| 43. | NM_001018 | RPS15 | Ribosomal protein S15 | 19p13.3 | 0.006189 | Up | Down |
| 44. | NM_021038 | MBNL | Muscleblind (*Drosophila*)-like | 3q25 | 0.006189 | Down | Up |
| 45. | NM_012323 | U-MAF | V-maf musculoaponeurotic fibrosarcoma, protein F | 22q13.1 | 0.006189 | Down | Up |
| 46. | NM_005138 | SCO1L | SCO (cytochrome oxidase deficient, yeast) homolog 2 | 22q13.33 | 0.006189 | Down | Up |
| 47. | AF186779 | KIAA0959 | RalGDS-like gene | 1q25.2 | 0.006189 | Down | Up |
| 48. | D26054 | FBP | Fructose-1,6-bisphosphatase 1 | 9q22.3 | 0.006189 | Up | Down |
| 49. | U37546 | API2, MIHC, HIAP1 | Baculoviral IAP repeat-containing 3 | 11q22 | 0.006189 | Down | Up |
| 50. | AB046845 | SMURF1 | E3 ubiquitin ligase SMURF1 | 7q21.1-q31.1 | 0.006189 | Down | Up |

TABLE 4

The first 50 genes obtained from the supervised MDS analysis of tumor versus benign tissues of all the moderate risk CaP patients, ranked by p-value: (T vs N Intensities of 9 MR)

| No. | Genbank Accession | Common Name of Genes | Description of Genes | Map | p-Value | Expression Regulation Tumor | Benign |
|---|---|---|---|---|---|---|---|
| 1. | NM_014324 | AMACR | Alpha-methylacyl-CoA racemase | 5p13.2-q11.1 | 0 | Up | Down |
| 2. | NM_006457 | ENH | LIM protein (similar to rat protein kinase C-binding enigma) | 4q22 | 0.000009 | Up | Down |
| 3. | AI351043 | ESTs | *H. sapiens* cDNA clone IMAGE: 1948310 | 21 | 0.000011 | Up | Down |
| 4. | AI433463 | MME | *H. sapiens* cDNA clone similar to NEPRILYSIN (HUMAN) | 3q25.1-q25.2 | 0.000028 | Down | Up |
| 5. | BE256479 | HSPD1 | *H. sapiens* cDNA clone IMAGE: 3352031 | 12p13.31 | 0.000037 | Up | Down |
| 6. | NM_015900 | PS-PLA1 | Phosphatidylserine-specific phospholipase A1alpha | 3q13.13-q13.2 | 0.000083 | Up | Down |
| 7. | NM_002343 | LTF | Lactotransferrin | 3q21-q23 | 0.000083 | Down | Up |
| 8. | NM_001099 | PAP | Acid phosphatase, prostate | 3q21-q23 | 0.000083 | Down | Up |
| 9. | T15991 | CHRM3 | IB2413 Infant brain, Bento Soares *Homo sapiens* cDNA | 1q41-q44 | 0.00011 | Up | Down |
| 10. | NM_005084 | PAFAH | Phospholipase A2, group VII | 6p21.2-p12 | 0.00011 | Up | Down |
| 11. | NM_004503 | HOXC6 | Homeo box C6 | 12q12-q13 | 0.00011 | Up | Down |
| 12. | N74607 | AQP3 | *H. sapiens* cDNA clone IMAGE: 296424 | 9p13 | 0.000149 | Down | Up |
| 13. | BC003068 | SLC19A1 | Solute carrier family 19 (folate transporter), member 1 | 21q22.3 | 0.000149 | Up | Down |
| 14. | M21535 | ERG (ets-related gene) | ERG v-ets erythroblastosis virus E26 oncogene like (avian) | 21q22.3 | 0.000149 | Up | Down |
| 15. | NM_013451 | MYOF, | Fer-1 (*C. elegans*)-like 3 (myoferlin) | 10q24 | 0.0002 | Down | Up |
| 16. | NM_006017 | AC133, CD133 | Prominin (mouse)-like 1 | 4p15.33 | 0.0002 | Down | Up |
| 17. | BE550599 | CACNA1D | *H. sapiens* cDNA clone IMAGE: 3220210 | 3p14.3 | 0.0002 | Up | Down |
| 18. | U22178 | PSP57, PSP94 | Microseminoprotein, beta- | 10q11.2 | 0.0002 | Down | Up |
| 19. | NM_015865 | JK, UT1, UTE | Solute carrier family 14 (urea transporter), member 1 | 18q11-q12 | 0.000275 | Down | Up |
| 20. | NM_000441 | PDS, DFNB4 | Solute carrier family 26, member 4 | 7q31 | 0.000275 | Down | Up |
| 21. | AA877789 | MYO6 | *H. sapiens* cDNA clone IMAGE: 1161091 | 6q13 | 0.000275 | Up | Down |
| 22. | AI356398 | ZFP36L2 | *H. sapiens* cDNA clone IMAGE: 2028039 | 2 | 0.000275 | Down | Up |
| 23. | BC000915 | CLIM1, CLP36 | PDZ and LIM domain 1 (elfin) | 10q22-q26.3 | 0.000275 | Down | Up |
| 24. | NM_000286 | PEX12 | Peroxisomal biogenesis factor 12 | 17q11.2 | 0.000275 | Up | Down |
| 25. | NM_003671 | CDC14B1, CDC14B2, | Homo sapiens CDC14 cell division cycle 14 homolog B (*S. cerevisiae*) (CDC14B), transcript variant 1, mRNA | 9q22.2-q22.31 | 0.000386 | Down | Up |
| 26. | NM_016545 | SBB148 | Immediate early response 5 | 1q24.3 | 0.000386 | Down | Up |
| 27. | NM_002443 | PSP57, PSP94 | Microseminoprotein, beta- | 10q11.2 | 0.000386 | Down | Up |
| 28. | NM_004999 | DFNA22 | Myosin VI | 6q13 | 0.000386 | Up | Down |
| 29. | X99268 | TWIST | Twist (*Drosophila*) homolog | 7p21.2 | 0.000386 | Up | Down |
| 30. | NM_023009 | MACMARCKS | Macrophage myristoylated alanine-rich C kinase substrate | 1p34.3 | 0.000386 | Up | Down |
| 31. | AI721219 | TRAF3 | as68b11.x1 Barstead colon HPLRB7 *Homo sapiens* cDNA clone IMAGE: 2333853 3', mRNA sequence. | 14q32.33 | 0.000547 | Down | Up |
| 32. | NM_001584 | D11S302E | Chromosome 11 open reading frame 8 | 11p13 | 0.000547 | Down | Up |
| 33. | NM_018846 | SBBI26 | SBBI26 protein | 7p15.3 | 0.000547 | Up | Down |
| 34. | M87771 | BEK, KGFR, | Fibroblast growth factor receptor 2 | 10q26 | 0.000547 | Down | Up |
| 35. | AF275945 | EVA1 | Epithelial V-like antigen 1 | 11q23.3 | 0.000547 | Down | Up |
| 36. | AI791860 | ESTs | *H. sapiens* cDNA clone IMAGE: 1011110 | | 0.000547 | Up | Down |
| 37. | BC001282 | NHC | High-mobility group (nonhistone chromosomal) protein 17-like 3 | 6p21.3 | 0.000547 | Down | Up |

TABLE 4-continued

The first 50 genes obtained from the supervised MDS analysis of tumor versus benign tissues of all the moderate risk CaP patients, ranked by p-value: (T vs N Intensities of 9 MR)

| No. | Genbank Accession | Common Name of Genes | Description of Genes | Map | p-Value | Expression Regulation Tumor | Expression Regulation Benign |
|---|---|---|---|---|---|---|---|
| 38. | NM_002015 | FKH1, FKHR | Furkhead box O1A (rhabdomyosarcoma) | 13q14.1 | 0.000547 | Down | Up |
| 39. | X15306 | NF-H | *H. sapiens* NF-H gene, exon 1 (and joined CDS). | 22q12.2 | 0.000547 | Down | Up |
| 40. | BE965029 | EST | *H. sapiens* cDNA clone IMAGE: 3886131 | 11 | 0.000775 | Up | Down |
| 41. | NM_002275 | KRT15 | Keratin 15 | 17q21 | 0.000775 | Down | Up |
| 42. | NM_001511 | MGSA, CXCL1 | GRO1 oncogene | 4q21 | 0.000775 | Down | Up |
| 43. | NM_005213 | STF1, STFA | Cystatin A (stefin A) | 3q21 | 0.000775 | Down | Up |
| 44. | NM_007191 | WIF-1 | Wnt inhibitory factor-1 | 12q14.2 | 0.000775 | Down | Up |
| 45. | H15129 | MEIS3 | EPIDERMAL GROWTH FACTOR-LIKE CRIPTO PROTEIN | 17 | 0.000775 | Down | Up |
| 46. | AW452623 | EST | *H. sapiens* cDNA clone IMAGE: 3068608 | 13 | 0.000775 | Up | Down |
| 47. | X90579 | EST | *H. sapiens* DNA for cyp related pseudogene | 7 | 0.000775 | Down | Up |
| 48. | BC001388 | ANX2, ANX2L4 | Annexin A2 | 15q21-q22 | 0.001116 | Down | Up |
| 49. | NM_014863 | BRAG, | B cell RAG associated protein | 10q26 | 0.001116 | Down | Up |
| 50. | NM_021076 | NEFH | Neurofilament, heavy polypeptide (200 kD) | 22q12.2 | 0.001116 | Down | Up |

TABLE 5

Top 50 Unregulated Genes in All the 18 Samples (HR and MR) obtained from Tumor over Benign (T/B) ratio.

| No | Genbank ID | T/N ratio | Common Name of Genes | Description | Map |
|---|---|---|---|---|---|
| 1. | AF047020 | 39.86910 | AMACR | Alpha-methylacyl-CoA racemase | 5p13.2-q11.1 |
| 2. | M54886 | 20.86411 | LOC51334 | Mesenchymal stem cell protein DSC54 | 5p13.1 |
| 3. | AF070581 | 19.07263 | ESTs | *Homo sapiens* cDNA clone IMAGE: 1948310 | 21 |
| 4. | NM_014324 | 18.04841 | TRG@ | T cell receptor gamma locus | 7p15-p14 |
| 5. | NM_001669 | 15.98177 | NPY | Neuropeptide Y | 7p15.1 |
| 6. | NM_018360 | 13.34037 | HOXC6 | Homeo box C6 | 12q12-q13 |
| 7. | AF092132 | 9.588665 | IMPD2 | IMP (inosine monophosphate) dehydrogenase 2 | 3p21.2 |
| 8. | NM_023067 | 7.712272 | HSPC028 | HSPC028 protein | 7p21.2 |
| 9. | NM_014439 | 7.031155 | LTBP1 | Latent transforming growth factor beta binding protein 1 | 2p22-p21 |
| 10. | AI613045 | 6.739595 | GMF | Glia maturation factor, beta | 14q22.1 |
| 11. | AB051446 | 6.563991 | DSC2 | HUMAN Q02487 DESMOCOLLIN 2A/2B PRECURSOR | 18q12.1 |
| 12. | NM_005342 | 6.442383 | TRG, TCRG | T cell receptor gamma locus | 7p15-p14 |
| 13. | D87012 | 6.327042 | PAWR | *H. sapiens* cDNA clone IMAGE: 1950862 | 12q21 |
| 14. | NM_018221 | 6.098105 | SNX2 | Sorting nexin 2 | 5q23 |
| 15. | NM_005114 | 5.769173 | HS3ST1 | Heparan sulfate (glucosamine)-3-O-sulfotransferase 1 | 11 |
| 16. | NM_022831 | 5.624385 | RA70, SAPS, SKAP55R | Src family associated phosphoprotein 2 | 7p21-p15 |
| 17. | NM_014324 | 5.621786 | TRG, TCRG | T cell receptor gamma locus | 7p15-p14 |
| 18. | NM_006820 | 5.550019 | BICD1 | Bicaudal D (*Drosophila*) homolog 1 | 12p11.2-p11.1 |
| 19. | NM_005574 | 5.454622 | FOLH1 | Folate hydrolase (prostate-specific membrane antigen) 1 | 11p11.2 |
| 20. | AL365343 | 5.451875 | KIAA0615 | *Homo sapiens* mRNA for KIAA0615 protein, complete cds. | 16q11.2 |
| 21. | NM_022580 | 5.318270 | TBCE | Tubulin-specific chaperone e | 1q42.3 |
| 22. | AK022765 | 5.315669 | CLDN8 | Claudin 8 | 21 |
| 23. | AF067173 | 5.272626 | P21, NSG1, D4S234 | Neuron-specific protein | 4p16.3 |
| 24. | NM_006220 | 5.180025 | SHMT2 | *Homo sapiens* cDNA clone IMAGE: 2676158 | 12q12-q14 |
| 25. | AL133600 | 5.146792 | ANK2 | *Homo sapiens* cDNA clone by03a08 | 4q25-q27 |
| 26. | AY009108 | 5.097967 | PSM | PROSTATE-SPECIFIC MEMBRANE ANTIGEN (HUMAN) | 2 |
| 27. | AL035603 | 5.076761 | FLJ10907 | Ribonuclease 6 precursor | 6q27 |
| 28. | NM_014017 | 5.058610 | MAPBPIP | Mitogen-activated protein-binding protein-interacting protein | 13 |
| 29. | BF247098 | 5.030722 | PHLP, DKFZp564M1863 | Phosducin-like | 9q12-q13 |
| 30. | U62296 | 4.992345 | GOLPH2 | Golgi phosphoprotein 2 | 9 |
| 31. | AF130082 | 4.988912 | EST | *Homo sapiens* clone FLC1492 PRO3121 mRNA, complete cds | |
| 32. | NM_020373 | 4.969535 | C8orf4 | Chromosome 8 open reading frame 4 | 8 |
| 33. | U90030 | 4.873056 | BICD1 | Bicaudal D homolog 1 (*Drosophila*) | 6 |
| 34. | NM_021071 | 4.821960 | KIAA0426 | KIAA0426 gene product | 6p22.2-p21.3 |
| 35. | NM_030817 | 4.753895 | KIAA1157 | KIAA1157 protein | 12q13.3-q14.1 |
| 36. | NM_019844 | 4.700642 | HPRT, HGPRT | Hypoxanthine phosphoribosyltransferase 1 | Xq26.1 |
| 37. | NM_004721 | 4.689246 | RPL29 | Ribosomal protein L29 | 3p21.3-p21.2 |
| 38. | NM_004866 | 4.669274 | EF2, EEF-2 | Eukaryotic translation elongation factor 2 | 19pter-q12 |
| 39. | NM_014501 | 4.610132 | BGN | Biglycan | Xq28 |
| 40. | NM_020655 | 4.575193 | SDC2 | Syndecan 2 (heparan sulfate proteoglycan 1, fibroglycan) | 8q22-q23 |
| 41. | NM_006716 | 4.557526 | ASK | Activator of S phase kinase | 19p13.11 |
| 42. | NM_002968 | 4.541752 | FOLH1 | Folate hydrolase (prostate-specific membrane antigen) 1 | 11q14.3 |

TABLE 5-continued

Top 50 Unregulated Genes in All the 18 Samples (HR and MR) obtained from Tumor over Benign (T/B) ratio.

| No | Genbank ID | T/N ratio | Common Name of Genes | Description | Map |
|---|---|---|---|---|---|
| 43. | X06268 | 4.539479 | NCUBE1 | Non-canonical ubquitin conjugating enzyme 1 | 6 |
| 44. | AK021609 | 4.520464 | PTH2, PTEN2, PSIPTEN | Phosphatase and tensin homolog (mutated in multiple advanced cancers 1), pseudogene 1 | 9p21 |
| 45. | NM_001133 | 4.479513 | TCTEX1L | T-complex-associated-testis-expressed 1-like | Xp21 |
| 46. | D38491 | 4.477160 | KIAA0461, POGZ, | Pogo transposable element with ZNF domain, KIAA0461 protein | 1q21.2 |
| 47. | NM_006426 | 4.385531 | DDX26 | Deleted in cancer 1; RNA helicase HDB/DICE1 | 13q14.12-q14.2 |
| 48. | AW058148 | 4.347362 | SPHAR | S-phase response (cyclin-related) | 1q42.11-q42.3 |
| 49. | U55209 | 4.293919 | MYO7A | myosin VIIA (Usher syndrome 1B) | 4 |
| 50. | NM_004610 | 4.275521 | KIAA0634, ASTN2 | Astrotactin 2 | 9q33.1 |

TABLE 6

Top 35 Downregulated Genes in All the 18 Samples (HR and MR) obtained from Tumor over Benign (T/B) ratio.

| No. | Genbank ID | T/N Ratio | Common Name of the Genes | Description | Map |
|---|---|---|---|---|---|
| 1. | X90579 | 0.181138 | CYP3A5 | Cytochrome P450, family 3, subfamily A, polypeptide 5 | 7 |
| 2. | NM_005213 | 0.198502 | STF1, STFA | Cystatin A (stefin A) | 3q21 |
| 3. | NM_005864 | 0.254524 | EFS1, HEFS | Signal transduction protein (SH3 containing) | 14q11.2-q12 |
| 4. | X15306 | 0.291665 | NF-H | H. sapiens NF-H gene, exon 1 (and joined CDS). | 22q12.2 |
| 5. | BE908217 | 0.319347 | ANXA2 | Annexin A2 | 15q21-q22 |
| 6. | BC001388 | 0.320110 | ANX2, LIP2, ANX2L4 | Annexin A2 | 15q21-q22 |
| 7. | U22178 | 0.326560 | PSP57, PSP94, PSP-94 | Microseminoprotein, beta- | 10q11.2 |
| 8. | NM_002443 | 0.338948 | PSP57, PSP94, PSP-94 | Microseminoprotein, beta- | 10q11.2 |
| 9. | NM_021076 | 0.359039 | NEFH | Neurofilament, heavy polypeptide (200 kD) | 22q12.2 |
| 10. | AI433463 | 0.360636 | MME, CD10, NEP, CALLA | Neprilysin | 3q25.1-q25.2 |
| 11. | AF275945 | 0.366939 | EVA1 | Epithelial V-like antigen 1 | 11q23.3 |
| 12. | NM_002343 | 0.370305 | LTF | Lactotransferrin | 3q21-q23 |
| 13. | NM_013451 | 0.378555 | MYOF, KIAA1207 | Fer-1 (C. elegans)-like 3 (myoferlin) | 10q24 |
| 14. | NM_001584 | 0.385272 | 239FB, D11S302E | Chromosome 11 open reading frame 8 | 11p13 |
| 15. | AL390736 | 0.391520 | BA209J19.1, GW112 | GW112(differentially expressed in hematopoietic lineages) | |
| 16. | NM_000441 | 0.392117 | PDS, DFNB4 | Solute carrier family 26, member 4 | 7q31 |
| 17. | AL031602 | 0.399115 | ESTs | ESTs | 1p34.1-35.3 |
| 18. | NM_004039 | 0.399796 | ANXA2 | Annexin A2 | 15q21-q22 |
| 19. | NM_001546 | 0.402261 | ID4 | DNA binding inhibitor protein of ID-4 | 6p22-p21 |
| 20. | NM_001099 | 0.406234 | PAP | Acid phosphatase, prostate | 3q21-q23 |
| 21. | X57348 | 0.422692 | 9112 | H. sapiens mRNA (clone 9112). | 1p35.2 |
| 22. | NM_020139 | 0.440648 | LOC56898 | Oxidoreductase UCPA | 4 |
| 23. | AU148057 | 0.444528 | DKK3, REIC | Dickkopf related protein-3 precursor (Dkk-3) (Dickkopf-3) (hDkk-3) | 11pter-p15.5 |
| 24. | BF059159 | 0.446108 | ROBO1, DUTT1, SAX3 | Roundabout, axon guidance receptor, homolog 1 (Drosophila) | 3p12 |
| 25. | BC001120 | 0.448109 | MAC2, GALBP, MAC-2, | Lectin, galactoside-binding, soluble, 3 (galectin 3) | 14q21-q22 |
| 26. | N74607 | 0.451123 | AQP3 | Aquqporin 3 | 9p13 |
| 27. | NM_013281 | 0.454835 | FLRT3 | Fibronectin leucine rich transmembrane protein 3 | 20p11 |
| 28. | NM_000700 | 0.456566 | ANX1, LPC1 | Annexin A1 | 9q12-q21.2 |
| 29. | X57348 | 0.458169 | 9112 | H. sapiens mRNA (clone 9112). | 1p35.2 |
| 30. | AI356398 | 0.467028 | ZFP36L2, ERF-2, TIS11D | EGF-respons factor 2 | 2 |
| 31. | AF016266 | 0.467787 | DR5, TRAILR2, TRICK2A, | Tumor necrosis factor receptor superfamily, member 10b | 8p22-p21 |
| 32. | S59049 | 0.467913 | BL34, IER1, IR20 | Regulator of G-protein signalling 1 | 1q31 |
| 33. | NM_000165 | 0.470393 | GJA1 | Gap junction protein, alpha 1, 43 kD (connexin 43) | 6q21-q23.2 |
| 34. | AI826799 | 0.471081 | EFEMP1, DRAD, FBNL | EGF-CONTAINING FIBULIN-LIKE EXTRACELLULAR MATRIX PROTEIN 1 | 2p16 |
| 35. | AL575509 | 0.476538 | ETS2 | V-ets erythroblastosis virus E26 oncogene homolog 2 (avian) | 21q22.2 |

Figure 2A:
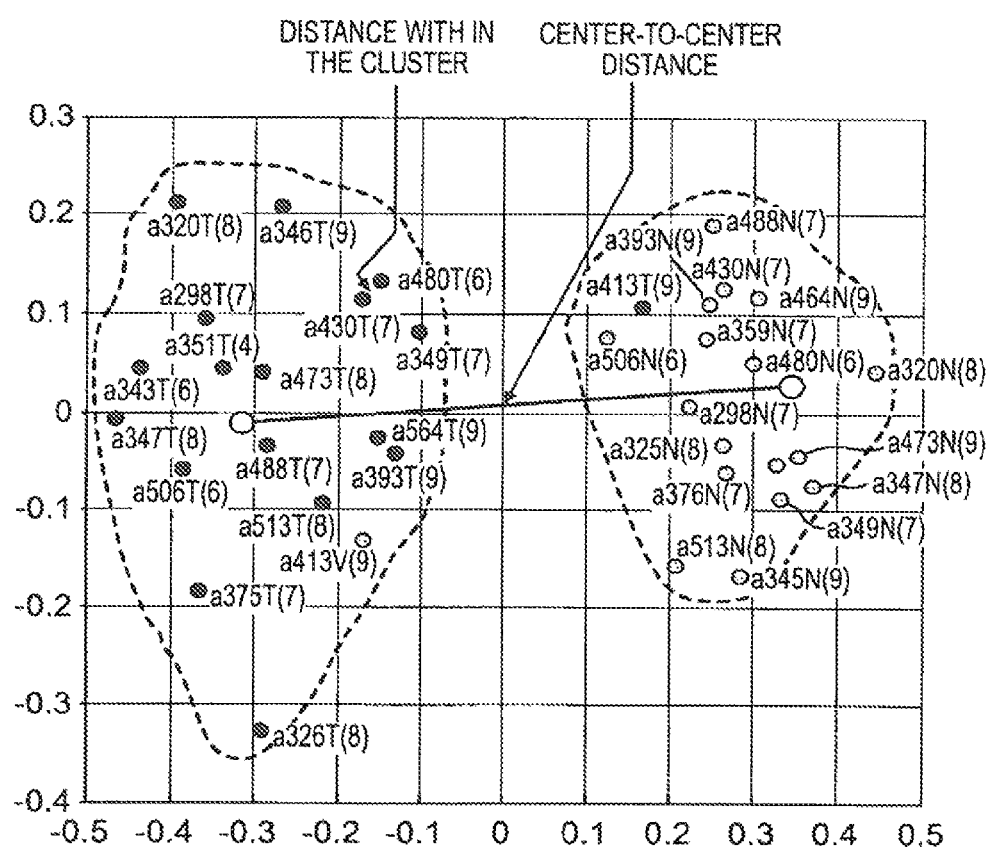
Figure 2B:
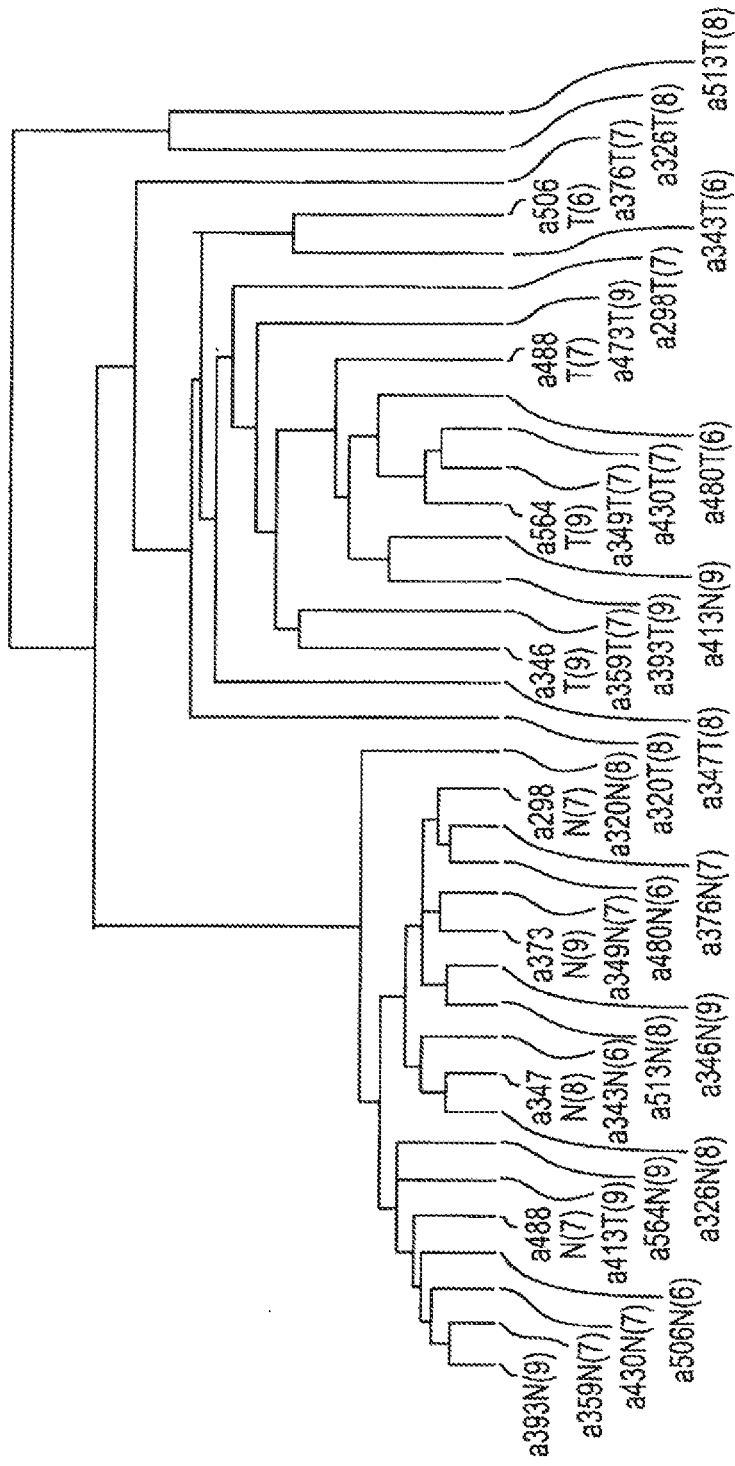

Classification between Tumor and Benign Prostate Epithelium:

A class prediction analysis using distance based Multi Dimensional Scaling (MDS) was used to determine expression differences between tumor and benign epithelial cells in 18 patients with radical prostatectomy. All the genes that meet a minimum level of expression were included in the analysis. We used the normalized intensities of all the 18 tumor and 18 normal samples for a class prediction analysis by distance based MDS to determine differentiation between tumor and benign tissue specific gene expression profile among all the 18 patients. Using a matrix of Pearson correlation coefficients from the complete pair-wise comparison of all the experiments we observed a significant overall difference in gene expression pattern between the tumor and benign tissue as displayed as a two-dimensional MDS plot in FIG. 2A. The position of the each tumor and benign samples is displayed in the MDS plot in two-dimensional Euclidean space with the distance among the samples reflecting correlation among the samples in each individual group (distance within the cluster) and as well as reflecting distinct separation between the two groups (center-to center distance) (FIG. 2A). The MDS plot was obtained from the top 200 genes obtained by 10,000 permutations of the tumor and benign intensities of 4566 genes. Out of these 200 genes that define the tumor specific alteration of gene expression, 53 genes had higher expression in the tumor samples and the remaining 147 genes had higher expression in the benign samples. A partial list of genes that distinctly discriminate the tumor and benign samples from all the 18 patients is shown in Table 1. We also performed a hierarchical clustering analysis using the 200 discriminatory genes. The hierarchical clustering algorithm resulted in a hierarchical dendrogram that identified two major distinct clusters of 16 tumor samples and 17 benign samples (FIG. 2B).

Figure 3A:
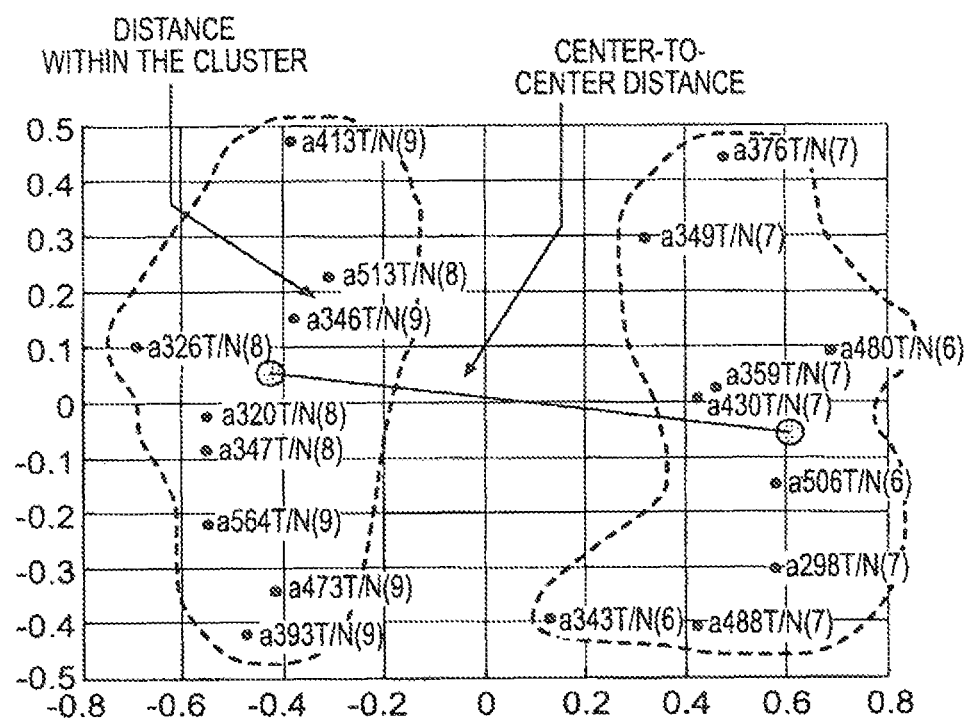

Classification of CaP into HR and MR Groups Using the Ratio of Tumor over Benign Gene Expression Intensities We used the tumor over benign gene expression intensity ratio (T/B ratio) (FIG. 3A) from the HR (9 patients) and MR (9 patients) groups for a class prediction analysis using distance based MDS method to determine if the 18 patients can be differentiated into the two patient groups. Pathological and clinical features of the 18 tumors used in our study were clearly distinguishable between the HR and MR groups. We observed a significant overall difference in expression pattern between the HR and MR groups. The distance between the samples reflects both the extent of correlation within each individual selected group (distance within the cluster) as well as distinct separation between the two selected groups (center-to-center distance) (FIG. 3A). The MDS plot obtained from top 200 genes by 10,000 permutations of the 4868 genes based on the T/B ratio is shown in FIG. 3A. Out of the top 200 genes of the MDS analysis 135 were over expressed in the HR group and 65 genes were over expressed in the MR group, The top 50 genes with best p-values identified by the T/B ratio based MDS analysis discriminating the HR and MR groups are listed in FIG. 3B. The approach we used for the interpretation of discrimination between the HR and MR groups was empirical. The 'weighted list' (FIG. 3B) of individual genes whose variance of change across all the tumor samples defines the boundary of a given cluster to predict a class that correlates with the pathological and clinical features of CaP. We also performed a hierarchical clustering to verify the results of the MDS analysis and also to test the potential of those 200 genes to predict class/group (HR and or MR) using another approach of analysis. The resulting hierarchical dendrogram of TB ratio demonstrates that 9 samples of the HR group formed a very distinct and tight cluster, as did the 9 samples of MR group (FIG. 3B).

Figure 3C:
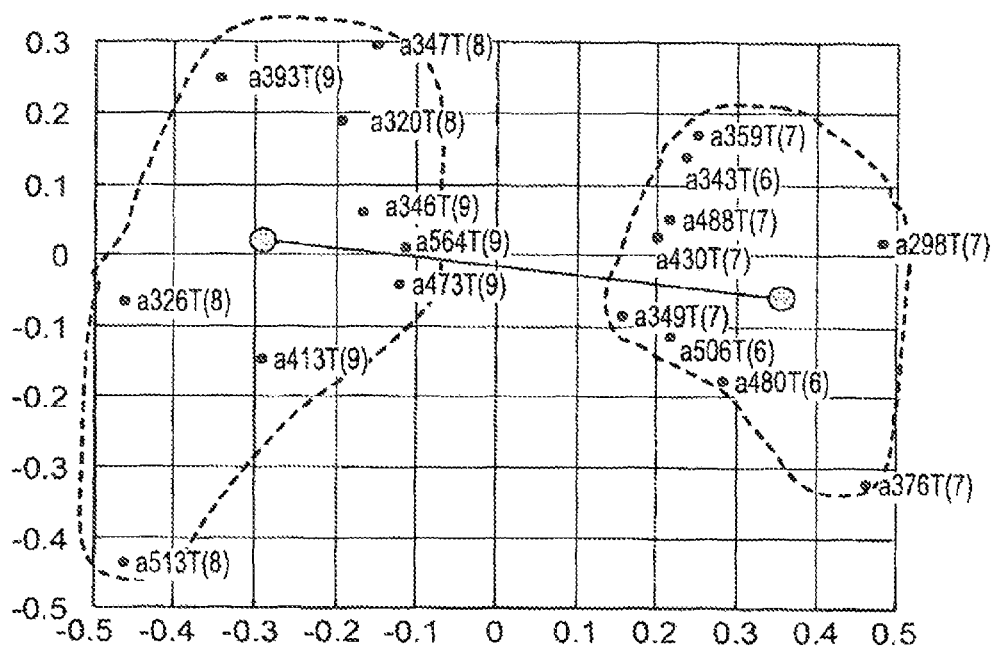
Figure 3D:
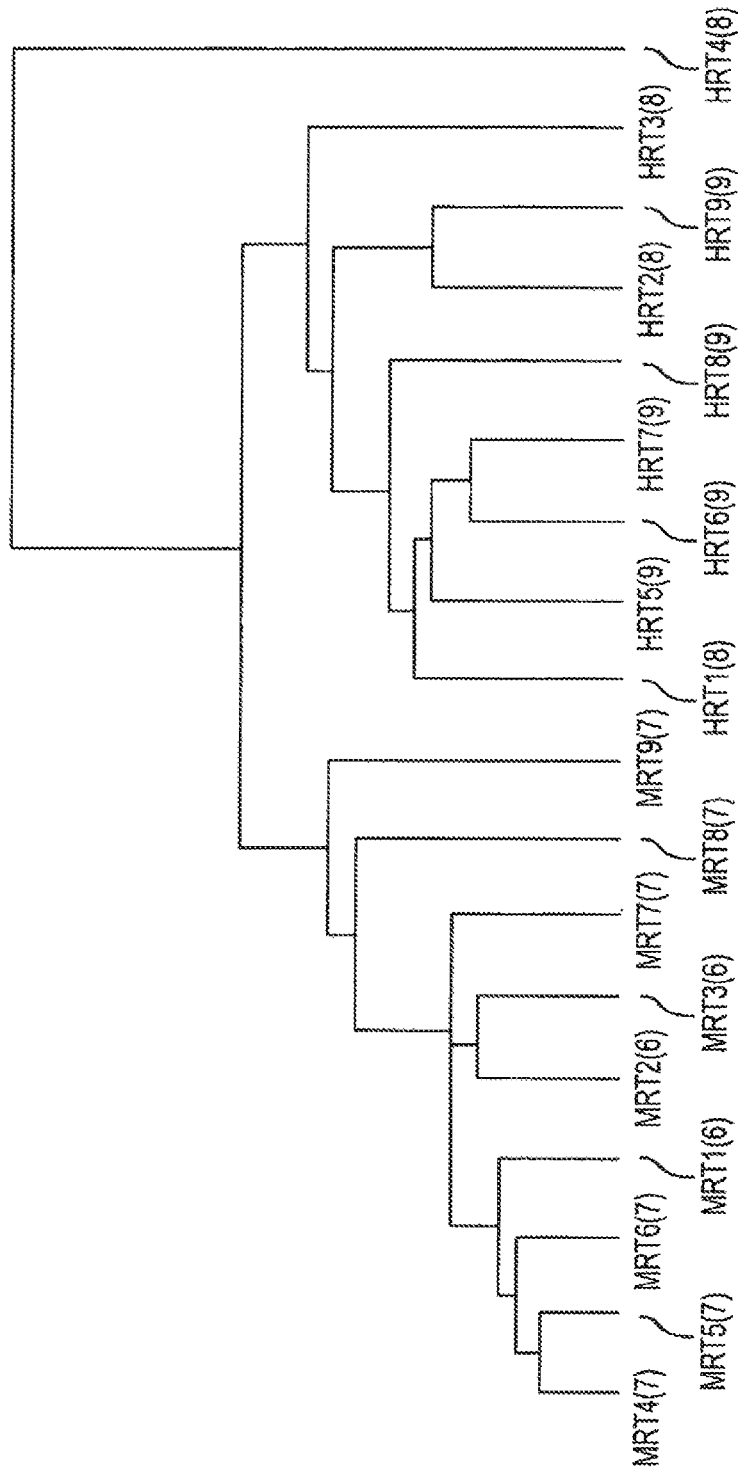

Classification of CaP into HR and MR groups based on Gene Expression Intensities in Tumor Cells MDS analysis was used to determine differentiation among 18 patients into HR and MR groups. An overall difference in tumor specific expression between the HR and MR groups is displayed as a two-dimensional MDS plot (FIG. 3C). The MDS plot obtained from 10,000 permutations of the gene expression intensities of 4115 genes from the tumor samples of 18 patients differentiated them into HR and MR groups based on the selected top 200 genes (FIG. 3C). Out of this 200 genes, 94 had higher expression in the HR groups and the remaining 106 genes had higher expression in the MR groups. We performed a hierarchical clustering analysis using the 200 discriminatory genes obtained from the supervised MDS analysis. The resulting hierarchical dendrogram of 18 tumor samples demonstrates that 9 tumor samples of the HR group and 9 tumor samples of the MR group were separated into two tight clusters. (FIG. 3D). The approach we utilized on the basis of the linear correlation of global gene expression in FIG. 3 to obtain 'gene cluster' interpretation to discriminate the HR and MR groups was empirical. Genes that discriminate the HR and MR groups are shown in Table 7.

TABLE 7

Top 17 genes analysis based on T/B fold change of HR vs MR groups

| | Gene Bank ID | Common Name | Description | Map | p-Value | HR | MR | Absent | Positive |
|---|---|---|---|---|---|---|---|---|---|
| 1 | NM_004522 | KINN, NKIIC | Kinesin family member 5C | 2q23.3 | 0.0001 | Up | Down | 4 | 60% |
| 3 | NM_018010 | HIPPI, FLJ10 | Hypothetical protein FLJ10147 | 3q13.13 | 0.0033 | Up | Down | 0 | 56% |
| 10 | NM_012245 | SKIP, NCOA- | SKI-interacting protein | 14q24.3 | 0.0076 | Up | Down | 2 | 42.80% |
| 11 | NM_015895 | LOC51053 | Geminin | 6p22.2 | 0.0076 | Up | Down | 2 | 71.40% |
| 14 | NM_003031 | SIAH1 | Seven in absentia (*Drosophila*) homolog 1 | 16q12 | 0.0076 | Up | Down | 3 | 66% |
| 42 | NM_000016 | ACADM | Acyl-Coenzyme A dehydrogenase, C-4 to C-12 straight | 1p31 | 0.0178 | Up | Down | 1 | 75% |
| 47 | NM_025087 | FLJ21511 | Hypothetical protein FLJ21511 | 4 | 0.0178 | Up | Down | 1 | 50% |
| 17 | NM_021038 | MBNL | Muscleblind (*Drosophila*)-like | 3q25 | 0.0076 | Down | Up | 2 | 71 |
| 25 | NM_006732 | GOS3 | FBJ murine osteosarcoma viral oncogene homolog B | 19q13.32 | 0.0076 | Down | Up | 3 | 83% |
| 51 | NM_001674 | ATF3 | Activating transcription factor 3 | 1q32.3 | 0.0178 | Down | Up | 0 | 100% |
| 7 | NM_002053 | GBP1 | Guanylate binding protein 1, interferon-inducible, 67 KD | 1p22.1 | 0.005 | Down | Up | 4 | 83% |
| 15 | NM_003407 | TTP, GOS24 | Zinc finger protein 36, C3H type, homolog (mouse) | 19q13.1 | 0.0076 | Down | Up | 1 | 62% |
| 26 | NM_003760 | EIF4G3 | Eukaryotic translation initiation factor 4 gamma, 3 | 1pter-p3 | 0.0076 | Down | Up | 4 | 40% |
| 38 | AK023938 | *Homo sapien* | SELECTED MODEL ORGANISM PROTEIN SIMILARITIES | 2q37.3 | 0.0178 | Down | Up | 4 | 80% |
| 45 | NM_016021 | NCUBE1 | Non-canonical ubiquitin conjugating enzyme 1 | 6 | 0.0178 | Down | Up ? | 3 | 66% |
| 5 | NM_021795 | SAP1 | ELK4, ETS-domain protein (SRF accessory protein 1) | 1q32 | 0.005 | Up | Down | 4 | 80% |
| 18 | NM_014454 | PA26 | P53 regulated PA26 nuclear protein | 6q21 | 0.0076 | Up | Down | 3 | 83% |

Figure 3E:
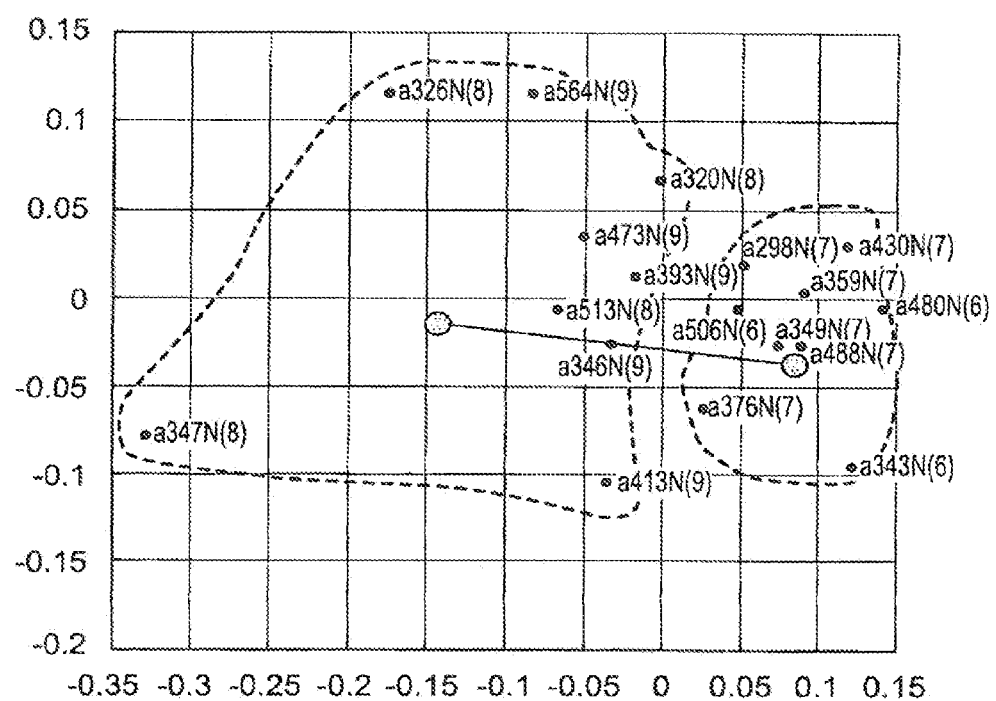

Classification of CaP into High Risk and Medium Risk Groups Based on Gene Expression Intensities in Benign Prostate Epithelial We used a similar MDS and Cluster analysis as in the tumor versus tumor sample gene expression intensities for the normalized intensities of 9 benign samples of HR group and 9 benign samples of MR group for a class prediction. Strikingly the MDS plot of the benign samples depicted distinct separation between the HR and MR groups (FIG. 3E). We observed a significant overall difference in expression pattern between the HR and MR groups. The MDS plot obtained from the top 200 genes by 10,000 permutations of the 3358 genes from the benign versus benign intensities (FIG. 3E). Out of this 200 genes 61 were over expressed in benign samples of the HR groups and the remaining 139 genes were over expressed in the MR groups. The 'weighted list' of individual genes whose variance of expression alteration across all the normal samples depicts the capability of a given cluster to predict classification. The hierarchical clustering algorithm identified a similar major cluster of the 9 benign samples of the HR group and a cluster of 9 benign samples of the MR group.

The weighted gene analysis by distance based supervised multidimensional scaling method we used, (depicted in FIGS. 3A, 3C, and 3E) utilizing the gene expression ratio of tumor and benign intensities, gene expression intensities of tumor samples and as well as normal for obtaining a 'weighted list' of individual genes, whose variance of change across all the tumor and benign samples distinctly delineate the boundary of a given cluster, to predict a class that correlates with the pathological and clinical features of CaP.

Independent In silico Cross Validation

In silico analysis for the predicted classifier was carried out using two independent data sets. The HR and MR groups were selected on the basis of Gleason score as that was the only criterion available for these data. At least 200 genes were extracted from all the MDS analysis (see methods for detail description). This subset of 200 classifier genes were found in the data of Welsh et al. 2001 and Sing et al. 2002. Exactly similar MDS analysis (p<0.001 as measured by 10,000 permutation testing) as described above was performed using the expression intensities of these 200 genes from Welsh and Singh data. MDS analysis using tumor over benign ratio of as low as 50 genes from the subset of 200 genes from Welsh data (FIG. 4A) as well as Singh data (FIG. 4B) clearly separated samples from HR group and samples from MR group. Thus, this observation elucidates that the differential expression profile of this small set of genes can be used to predict the identity or class or group of unknown prostate cancer samples on the basis of their clinico-pathological features. The outcome of this analysis depicts that the expression profile of this small number of genes is conserved across the independent data sets.

Validation of GeneChip Results by Real-Time PCR

To further validate the expression alterations of genes identified by GeneChip analysis with an indicated biological relevance to prostate cancer, primers and probes were obtained for real-time PCR analysis using AMACR and GSTP1. These genes were chosen for validation purposes because it has been reported previously by several investigators that AMACR is elevated and GSTP1 decreased in CaP. Each sample demonstrated a unique pattern of down-regulation of GSTP1 gene in 18 of 20 samples as well as up-regulation of AMACR (FIG. 1) the other two samples did show significant change (fold change less than 1.5).

One ng of total RNA samples from paired tumor and normal specimens was reverse-transcripted using Omnisensecript RT-kit (Qiagene, Valencia, Calif.) according to the manufacturer's protocol.

Quantitative gene expression analysis was performed using TaqMan Master Mix Reagent and an ABI prism 7700 Sequence Detection System (PE Applied Biosystems Foster, Calif.). All sets of primer and probe for tested genes were Assays-on-Demand Gene expression products obtained from PE Applied Biosystems. The expression of house keeping gene, GAPDH was simultaneously analyzed as the endogenous control of same batch of cDNA, and the target gene expression of each sample was normalized to GAPDH. For each PCR run, a master-mix was prepared on ice with 1× TaqMan Master Mix, 1× target gene primer/probe and 1×GAPDH primer/probe. Two microliters of each diluted cDNA sample was added to 28 µl of PCR master-mix. The thermal cycling conditions comprised an initial denaturation step at 95° C. for 10 minutes and 50 cycles at 95° C. for 15 seconds and 60° C. for 1 minute. RNA samples without reverse transcription were included as the negative control in each assay. All assays were performed in duplicate. Results were plotted as average $C_T$ (threshold cycle) of duplicated samples. The relative gene expression level was presented as "Fold Change" of tumor versus matched normal cells, which is calculated as: Fold change=$2^{(\Delta C_{Tnormal}-\Delta C_{Ttumor})}$, where $\Delta C_T$ means normalized $C_T$ value of target genes to GAPDH.

Example 3

Distinguishing Between ERG1 and ERG2 Isoforms

The Affymetrix GeneChip probe set (213541_s_at) and TaqMan probes used in the experiments described above recognize a region specific for both ERG1 and ERG2 isoforms (FIG. 6), but exclude isoforms 3 to 9. Although other primers and probes could be used, by way of example, TaqMan primers and probe recognizing both ERG1 and ERG2, but not other ERG isoforms were as follows:

```
Fwd primer:
                                      (SEQ ID NO: 7)
5'-AGAGAAACATTCAGGACCTCATCATTATG-3'

Reverse primer:
                                      (SEQ ID NO: 8)
5'-GCAGCCAAGAAGGCCATCT-3'

Probe:
                                      (SEQ ID NO: 9)
5'-TTGTTCTCCACAGGGT-3'
```

The probe has the reporter dye, 6-FAM, attached to the 5' end and TAMRA attached to the 3' end. The 3'-TAMRA effectively blocks extension during PCR.

To further distinguish between these two ERG isoforms, the expression of the ERG1 and ERG2 isoforms were tested in PC3 cells and in normal prostate tissue (pooled prostate RNA from 20 men, Clontech), as well as in microdissected tumor and normal prostate epithelial cells from 5 CaP patients (data not shown). Only ERG1 was expressed in the prostate cells and in PC3 cells. ERG2 expression was not detectable. A TaqMan QRT-PCR probe and primers were designed that specifically recognize only the ERG1 isoform (FIG. 6). Although other primers and probes could be used, by way of example, we designed TaqMan primers and probes recognizing only the ERG1 isoform as follows:

```
Forward primer:
                                        (SEQ ID NO: 10)
5'-CAGGTCCTTCTTGCCTCCC-3'

Reverse primer:
                                        (SEQ ID NO: 11)
5'-TATGGAGGCTCCAATTGAAACC-3'

Probe:
                                        (SEQ ID NO: 12)
5'-TGTCTTTTATTTCTAGCCCCTTTTGGAACAGGA-3'.
```

The probe has the reporter dye, 6-FAM, attached to the 5' end and TAMRA attached to the 3' end. The 3'-TAMRA effectively blocks extension during PCR.

ERG1 expression was determined in 228 RNA specimens from microdissected matched tumor and benign prostate epithelial cells of 114 CaP patients. Overall, 62.4% of the 114 CaP patients analyzed had significant over expression of ERG1 isoform in their tumor cells (i.e., greater than 2 fold ERG1 expression in tumor versus benign cells), while 16.6% of CaP patients had no detectable ERG1 expression, 15.0% had under expression of ERG1 (less than 0.5 fold difference in ERG1 expression in tumor versus benign cells), and 6.0% had no significant difference (0.5 to 2 fold difference in ERG1 expression between tumor versus benign cells).

In a further study, ERG expression was analyzed in 82 CaP patients. Using the TaqMan primers and probes discussed above, we observed tumor-associated over expression of ERG1 (isoform 1 only) and ERG (isoforms 1 and 2) in 63.4% and 72.0% of the patients, respectively. Therefore, ERG1 isoform specific expression may actually reflect an underestimate of the overall ERG expression in CaP.

Example 4

Correlation of ERG1 Expression With Various Clinico-Pathologic Features

Since the ERG1 tumor versus benign expression ratio data did not have normal distribution, the Wilcoxon Rank Sum Test was used to analyze its relationship with various clinico-pathologic features, as shown in Table 8.

TABLE 8

Relationship of ERG1 expression ratios in tumor versus benign prostate epithelial cells with patient clinical factors

| Clinical factors | N | Median of ERG1 fold changes | Mean scores of ERG1 fold changes | P |
|---|---|---|---|---|
| PSA recurrence | | | | |
| No | 75 | 142.2 | 52.19 | 0.0042 |
| Yes | 20 | 1.2 | 32.30 | |
| Tumor Differentiation | | | | 0.0020 |
| Well & Moderate | 40 | 362.3 | 57.62 | |
| Poor | 54 | 13.9 | 40.00 | |
| Pathologic T stage | | | | 0.0136 |
| pT2 | 38 | 502.0 | 53.45 | |
| pT3-4 | 52 | 33.5 | 39.69 | |
| Margin status | | | | 0.0209 |
| Negative | 64 | 197.0 | 52.55 | |
| Positive | 31 | 20.4 | 38.61 | |
| Seminal vesicle | | | | 0.2555 |
| Negative | 82 | 106.7 | 49.28 | |
| Positive | 13 | 6.9 | 39.92 | |
| Race | | | | 0.0086 |
| Caucasian | 73 | 172.1 | 52.08 | |
| African American | 22 | 3.8 | 34.45 | |
| Family history | | | | 0.3887 |
| No | 70 | 106.7 | 49.46 | |
| Yes | 25 | 4.8 | 43.92 | |
| Diagnostic PSA (ng/ml) | | | | |
| <=4 | 13 | 101.3 | 57.15 | 0.1801 |
| >4-10 | 62 | 112.1 | 48.03 | |
| >10 | 19 | 20.5 | 39.16 | |
| Gleason sum | | | | 0.2923 |
| <7 | 33 | 112.0 | 52.06 | |
| =7 | 45 | 118.1 | 47.16 | |
| >7 | 16 | 21.0 | 39.06 | |

As shown in Table 8, 95 CaP patients with detectable ERG1 expression were analyzed by Wilcoxon rank sum test. N represents the number of CaP patients falling into the indicated clinical factor category. Significant p values (<0.05) are in bold face.

We also found a significant correlation of high ERG1 over expression with Caucasian over African American ethnicity (p=0.0086) (Table 8). To further explore the correlation with PSA recurrence, Kaplan-Meier survival analysis was performed based on three patient groups: 1) CaP patients with tumor versus benign ERG1 expression ratio of less than 2 fold; 2) CaP patients with tumor versus benign ERG1 expression ratio of 2-100 fold; and 3) CaP patients with tumor versus benign ERG1 expression ratio of greater than 100 fold (FIG. 7). The results show that patients with higher ERG1 over expression in their prostate tumor tissue had significantly longer PSA recurrence-free survival (log rank test, P=0.0006) (FIG. 7). The 36-months PSA recurrence-free survival for patients with less than 2 fold ERG1 expression ratio (n=24) was 54.4%, while for patients with greater than 100 fold ERG1 expression ratio (n=47) it was 87.7%. From a univariate COX proportional hazard ratio regression analysis for PSA recurrence-free time using ERG1 tumor/benign cells expression ratio, race, diagnostic PSA, Gleason sum, pathologic T stage, margin status, and seminal vesicle invasion status, we found that five of these variables (ERG1 tumor/benign cells expression ratio, Gleason sum, pathologic T stage, margin status, seminal vesicle invasion) had a significant p value (Table 9).

TABLE 9

Correlation of clinical parameters and ERG1 expression ratios in tumor versus benign prostate epithelial cells with PSA recurrence-free time after radical prostatectomy

| Factors | Crude Hazard Ratio (95% CI) | P |
|---|---|---|
| ERG1 fold changes | | 0.0024 |
| 2-100 fold vs. <2 fold | 0.291 (0.093-0.915) | 0.0347 |
| >100 fold vs. <2 fold | 0.173 (0.060-0.498) | 0.0011 |
| Race | | |
| Caucasian vs. African American | 1.092 (0.395-3.016) | 0.8657 |
| Diagnostic PSA | | 0.8723 |
| >4-10 vs. <=4 | 0.976 (0.275-3.468) | 0.9705 |
| >10 vs. <=4 | 1.285 (0.307-5.378) | 0.7313 |
| Gleason Sum | | 0.0001 |
| 7 vs. 2-6 | 1.574 (0.393-6.296) | 0.5215 |
| 8-10 vs. 2-6 | 9.899 (2.752-35.610) | 0.0004 |

TABLE 9-continued

Correlation of clinical parameters and ERG1 expression ratios in tumor versus benign prostate epithelial cells with PSA recurrence-free time after radical prostatectomy

| Factors | Crude Hazard Ratio (95% CI) | P |
|---|---|---|
| Pathologic T stage | | |
| pT3/4 vs. pT2 | 6.572 (1.517-28.461) | 0.0118 |
| Margin status | | |
| Positive vs. Negative | 2.825 (1.169-6.826) | 0.0210 |
| Seminal Vesicle | | |
| Positive vs. Negative | 3.792 (1.487-9.672) | 0.0053 |

In Table 9, crude hazard ratios with 95% confidence interval are shown for ERG1 fold change (tumor versus benign) and six clinical parameter categories in a univariate COX proportional hazard ratio analysis. Significant p values are in bold face. The multivariate COX proportional hazard ratio regression analysis of the significant variables from the univariate analysis shows that ERG1 overexpression (greater than 100 fold vs. less than 2 fold: p=0.0239, RR=0.274, overall p value 0.0369), and Gleason sum (Gleason 8-10 vs. Gleason 2-6: p=0.0478, RR=4.078, overall p value 0.0148) are independent predictors of PSA recurrence after radical prostatectomy (Table 10). These results demonstrate that the status of ERG1 expression ratios (tumor vs. benign) in radical prostatectomy specimens carries a predictive value for patient prognosis.

TABLE 10

| Factors | Crude Hazard Ratio (95% CI) | P |
|---|---|---|
| ERG1 fold changes | | 0.0369 |
| 2-100 fold versus <2 fold | 0.320 (0.097-1.059) | 0.0620 |
| >100 fold versus <2 fold | 0.274 (0.089-0.843) | 0.0239 |
| Gleason Sum | | 0.0148 |
| 7 versus 2-6 | 0.948 (0.223-4.033) | 0.9424 |
| 8-10 versus 2-6 | 4.078 (1.014-16.401) | 0.0478 |
| Pathologic T stage | | |
| PT3/4 versus pT2 | 3.306 (0.636-17.177) | 0.1550 |
| Margin status | | |
| Positive versus Negative | 1.116 (0.421-2.959) | 0.8254 |
| Seminal Vesicle | | |
| Positive versus Negative | 1.308 (0.466-3.670) | 0.6098 |

ERG1 expression in prostate tumor tissue showed highly significant association with longer PSA recurrence free survival (p=0.0042), well and moderately differentiated grade (p=0.0020), lower pathologic T stage (p=0.0136), and negative surgical margin status (p=0.0209), suggesting that ERG1 over expression in tumor cells is generally higher in less aggressive CaP than in more aggressive CaP (Table 8).

The ERG1 over expression in tumor cells identified by GeneChip analysis and verified by real time QRT-PCR assays was further validated by in situ hybridization. Based on the real time QRT-PCR data, 6 patients with high ERG1 over expression in their tumor cells (and as a control one patient with no ERG1 over expression) were selected for in situ hybridization and quantitative image analysis in a blinded fashion. As expected, in each case the in situ expression data confirmed the over expression of ERG1 in the tumor epithelial cells (FIG. 8).

Example 5

Generation and Characterization of ERG Antibody

Cloning of ERG1 into Tetracycline Regulated Mammalian Expression Vectors:

ERG1 cDNA was subcloned into tetracycline-regulated mammalian expression vectors (pTet-off, EC1214A). The constructs generated include, pTet-off-ERG1 (sense), pTet-off-ERG1 (antisense), pTet-off-FlagERG1 (sense) and pTet-off-FlagERG1 (antisense). Originally, ERG1 construct in a riboprobe vector pGEM was obtained from Dr. Dennis K. Watson, Medical University of South Carolina. The constructs were verified by dideoxy sequencing and agarose gel analysis.

Generation of Polyclonal ERG Antibody:

Antibodies against ERG were generated using peptide antigens derived from the full length ERG1 coding sequence. The epitope for the antigen were carefully selected such that the antibody recognizes specifically ERG1/2/3 and not other members of the ETS family (FIG. 9). The following peptides, having the highest hydrophilicity (−1.26 and −0.55) and antigenicity in the desired region, were used to generate antibodies:

```
Peptide M-50-mer:
                                   (SEQ ID NO: 13)
CKALQNSPRLMHARNTDLPYEPPRRSAWTGHGHPTPQSKAAQPSPSTVP

K-[NH2]

Peptide C-49-mer:
                                   (SEQ ID NO: 14)
CDFHGIAQALQPHPPESSLYKYPSDLPYMGSYHAHPQKMNFVAPHPPAL
```

Cysteine was added to each peptide for conjugation. Peptide M is amidated at the C-terminal residue because it is an internal pepetide.

The synthesis of the peptide epitopes and the immunization of rabbits were carried out in collaboration with Bio-Synthesis Inc. Two rabbits were immunized for each of the two epitopes. Bleeds obtained post immunization were collected and tested. Subsequently, bleeds from one of the rabbits from each epitope were affinity purified using SulfoLink kit (Pierce) and were verified by immunoblot analysis.

Characterization of Polyclonal ERG Antibody by Immunoblot Analysis:

To characterize the affinity purified antibody, we transiently transfected HEK-293 (Human embryonic kidney cell line, ATCC, Manassas, Va.) with ERG1 constructs pTet-off-ERG1 (sense) and pTet-off-FlagERG1 (sense) using Lipofectamine reagent (Invitrogen, Carlsbad, Calif.) as per manufacturers instructions. HEK-293 that were not transfected with the plasmid served as a transfection control. The cells were harvested 48 hours post-transfection and processed for immunoblot analysis. Expression of ERG1 following transfection was determined by immunoblotting using the affinity purified polyclonal antisera generated against the unique M- and C-ERG epitopes described above. Endogenous ERG1 expression was not detected in non-transfected HEK-293 cells. However, the ERG antibodies detected ERG1 expression in HEK-293 cells transfected with the various ERG1 constructs. Tetracycline (2 ug/ml) abolished ERG1 expression in both tetracycline-regulated constructs, pTet-off-ERG1 (sense) and pTet-off-FlagERG1

(sense). The M2-Flag antibody specifically recognized only the Flag-tagged ERG1 protein.

Example 6

Combined Expression of ERG, AMACR, and DD3 Genes in Prostate Tumors

The strikingly high frequency of ERG over expression in CaP cells led to a comparison of ERG expression with two other genes, AMACR and DD3, that are also over expressed in CaP cells. We have evaluated quantitative gene expression features of AMACR and DD3, along with the ERG gene, in laser microdissected matched tumor and benign prostate epithelial cells from 55 CaP patients.

Although other primers and probes can be used, by way of example, we designed the following TaqMan primers and probe recognizing the DD3 gene:

```
Forward primer:
                                        (SEQ ID NO: 15)
5'-CACATTTCCAGCCCCTTTAAATA-3'

Reverse primer:
                                        (SEQ ID NO: 16)
5'-GGGCGAGGCTCATCGAT-3'

Probe:
                                        (SEQ ID NO: 17)
5'-GGAAGCACAGAGATCCCTGGGAGAAATG-3'.
```

The probe has the reporter dye, 6-FAM, attached to the 5' end and TAMRA attached to the 3' end. The 3'-TAMRA effectively blocks extension during PCR.

AMACR TaqMan primers and probe were purchased from Applied Biosystems.

AMACR and DD3 showed upregulation in tumor cells of 78.2% and 87.3% of CaP patients, respectively (FIG. 5). ERG over expression in tumor cells was detected in 78.2% of the same group of CaP patients (FIG. 5). Comparative expression analysis revealed that when the AMACR and ERG expression data are combined, 96.4% of the CaP patients showed upregulation of either of the two genes in tumor cells (FIG. 5). Similarly, the combination of the ERG and DD3 expression data improved the cancer detection power of either of the genes to 96.4% (FIG. 5). When combining the expression data from all the three genes, 98.2% of the CaP patients showed upregulation of at least one of the three genes in tumor cells (FIG. 5). Thus, screening for ERG gene expression, alone, or in combination with other genes that are over expressed in CaP, such as AMACR and DD3, provides a new, powerful diagnostic and prognostic tool for CaP.

Example 7

Under Expression of LTF in Malignant Prostate Epithelium

One of the most consistently under expressed genes in CaP cells was LTF (Table 1). Validation by QRT-PCR (TaqMan) in LCM-derived tumor and benign prostate epithelial cells confirmed a consistent, tumor associated LTF under expression in 100% of CaP cells tested (FIG. 1D). As a quality control, the expression of AMACR, a recently identified CaP tissue marker, and of GSTP1, a gene showing commonly reduced or absent expression in CaP (Nelson et al., Ann. N.Y. Acad. Sci., 952:135-44 (2001)), was also determined (FIGS. 1B and 1C, respectively). Robust under expression similar to LTF, was observed for GSTP1, while the increased expression of AMACR was noted in 95% of the tumor cells tested, confirming the high quality of the tumor and benign LCM specimens and the reliability of the QRT-PCR. In a further study, LTF expression was analyzed by QRT-PCR in in microdissected tumor and benign prostate epithelial cells of 103 CaP patients. The results were consistent with the initial results, showing tumor associated under expression in 76% of patients (78 of 103).

LTF under expression was also validated at the protein level with anti-LTF goat polyclonal antibody (Santa Cruz, Calif., sc-14434) using Western blot analysis on protein lysates and immunohistochemistry techniques. Hematotoxylin-eosin (H&E) and LTF staining was performed on tissue samples from 30 CaP patients by immunocytochemical analysis. In 30 of 30 (100%) cases, benign epithelial cells adjacent to tumor cells were highly positive for LTF, whereas, on average, less than 10% of prostate tumor cells revealed LTF positive cytoplasmic staining.

The specification is most thoroughly understood in light of the teachings of the references cited within the specification which are hereby incorporated by reference. The embodiments within the specification provide an illustration of embodiments of the invention and should not be construed to limit the scope of the invention. The skilled artisan readily recognizes that many other embodiments are encompassed by the invention.

What is claimed is:

1. A method of diagnosing prostate cancer in a subject, comprising:
   a) measuring the expression level of a human ERG polypeptide in a biological sample from the subject, wherein the biological sample comprises prostate epithelial cells and wherein the expression level of the human ERG polypeptide is measured by an immunoassay using a monoclonal antibody that binds to the human ERG1 polypeptide and does not bind to the human ETS domain; and
   b) correlating the expression level of the human ERG polypeptide with the presence of prostate cancer in the subject, wherein increased expression of the human ERG polypeptide in the biological sample as compared to the expression of the human ERG polypeptide in a control sample indicates the presence of prostate cancer in the subject.

2. The method of claim 1, wherein the monoclonal antibody is generated using a fragment of the human ERG1 polypeptide as an immunogen.

3. The method of claim 1, wherein the monoclonal antibody binds to the human ERG1, ERG2, and ERG3 polypeptides.

4. A method of diagnosing prostate cancer in a subject, comprising:
   a) measuring the expression level of a human ERG polypeptide in a biological sample from the subject, wherein the biological sample comprises prostate epithelial cells and wherein the expression level of the human ERG polypeptide is measured by an immunoassay using a monoclonal antibody that binds to the human ERG1 polypeptide; and
   b) correlating the expression level of the human ERG polypeptide with the presence of prostate cancer in the subject, wherein increased expression of the human ERG polypeptide in the biological sample as compared to the expression of the human ERG polypeptide in a control sample indicates the presence of prostate cancer in the subject, wherein the monoclonal antibody is generated using a fragment of the human ERG1 polypeptide as an immunogen, and wherein the monoclonal antibody binds to an epitope formed by amino acids 275-322 of the polypeptide encoded by a nucleic acid comprising the sequence of SEQ ID NO: 1.

5. The method of claim 1, wherein the monoclonal antibody binds to an epitope formed by amino acids 118-166 of the polypeptide encoded by a nucleic acid comprising the sequence of SEQ ID NO:1.

6. The method of claim 1, wherein the biological sample is chosen from a tissue sample, a blood sample, or a urine sample.

7. The method of claim 6, wherein the biological sample is a prostate tissue sample.

8. The method of claim 1, further comprising measuring the expression levels of a human AMACR polypeptide and correlating the expression levels of the human ERG polypeptide and the human AMACR polypeptide with the presence of prostate cancer in the subject.

9. The method of claim 8, wherein the human AMACR polypeptide is encoded by a nucleic acid comprising the sequence of SEQ ID NO. 3.

10. The method of claim 1, wherein the control sample is a noncancerous biological sample from the subject.

11. The method of claim 8, wherein the expression levels of the human ERG polypeptide and the human AMACR polypeptide in the biological sample are compared to the expression levels of the human ERG polypeptide and the human AMACR polypeptide in a control sample and wherein increased expression of the human ERG polypeptide and the human AMACR polypeptide in the biological sample as compared to the expression of the ERG polypeptide and the human AMACR polypeptide in the control sample indicates the presence of prostate cancer in the subject.

12. The method of claim 1, wherein the immunoassay is an immunohistochemistry assay.

13. A method of identifying prostate cancer in a subject, comprising:
   a) providing a prostate tissue sample from the subject;
   b) contacting the prostate tissue sample with a monoclonal antibody that binds to a human ERG polypeptide and does not bind to the human ETS domain; and
   c) measuring the level of expression of the human ERG polypeptide in the prostate tissue sample by detecting the amount of binding between the monoclonal antibody and the human ERG polypeptide in the prostate tissue sample;
   d) comparing the level of expression of the ERG polypeptide in the prostate tissue sample to the level of expression of the ERG polypeptide in a control sample; and
   e) identifying prostate cancer in the prostate tissue sample from the subject if the level of expression of the ERG polypeptide in the prostate tissue sample is increased as compared to the expression level of the ERG polypeptide in the control sample.

14. The method of claim 13, wherein the monoclonal antibody binds to the ERG1, ERG2, and ERG3 polypeptides.

15. A method of identifying prostate cancer in a subject, comprising:
   a) providing a prostate tissue sample from the subject;
   b) contacting the prostate tissue sample with a monoclonal antibody that binds to a human ERG polypeptide; and
   c) measuring the level of expression of the human ERG polypeptide in the prostate tissue sample by detecting the amount of binding between the monoclonal antibody and the human ERG polypeptide in the prostate tissue sample;
   d) comparing the level of expression of the ERG polypeptide in the prostate tissue sample to the level of expression of the ERG polypeptide in a control sample; and
   e) identifying prostate cancer in the prostate tissue sample from the subject if the level of expression of the ERG polypeptide in the prostate tissue sample is increased as compared to the expression level of the ERG polypeptide in the control sample, wherein the monoclonal antibody binds to an epitope formed by amino acids 275-322 of the polypeptide encoded by a nucleic acid comprising the sequence of SEQ ID NO:1.

16. The antibody of claim 13, wherein the monoclonal antibody binds to an epitope formed by the amino acid sequence of SEQ ID NO:14.

17. The method of claim 13, wherein the control sample is a noncancerous biological sample from the subject.

18. The method of claim 17, wherein the noncancerous biological sample from the subject is normal prostate tissue comprising benign prostate epithelial cells.

19. A method of detecting the expression of a human ERG polypeptide in a biological sample, wherein the biological sample comprises human prostate epithelial cells, the method comprising:
   a) contacting the human prostate epithelial cells with a monoclonal antibody that binds to a human ERG1, ERG2, and ERG3 polypeptide, wherein the monoclonal antibody binds to an epitope formed by amino acids 275-322 of the polypeptide encoded by a nucleic acid comprising the sequence of SEQ ID NO:1 or to an epitope formed by the amino acid sequence of SEQ ID NO:14; and
   b) measuring the level of expression of the human ERG polypeptide in the human prostate epithelial cells sample by detecting the amount of binding between the monoclonal antibody and the human ERG polypeptide in the human prostate epithelial cells.

20. The method of claim 19, further comprising a step of comparing the level of expression of the human ERG polypeptide in the human prostate epithelial cells to the level of expression of the human ERG polypeptide in a control sample.

21. The method of claim 19, wherein the biological sample is obtained from a patient that has prostate cancer or is suspected of having prostate cancer.

22. The method of claim 21, wherein the patient has been treated by radical prostate surgery.

23. The method of claim 19, further comprising detecting the expression of a human AMACR polypeptide in the biological sample.

24. The method of claim 1, wherein the expression level of the ERG polypeptide is correlated with longer PSA recurrence free survival, well and moderate tumor differentiation, a pathologic T stage of pT2 or lower, or a negative surgical status.

25. The method of claim 1, wherein the monoclonal antibody does not bind to a SMAP-PNT domain.

26. The method of claim 13, wherein the monoclonal antibody does not bind to a SMAP-PNT domain.

27. The method of claim 1, wherein the monoclonal antibody specifically binds to ERG1, ERG2, and ERG3, but does not specifically bind to another protein of the ETS family.

28. The method of claim 13, wherein the monoclonal antibody specifically binds to ERG1, ERG2, and ERG3, but does not specifically bind to another protein of the ETS family.

* * * * *

SEQUENCE LISTING

<160> NUMBER OF SEQ ID NOS: 17

<210> SEQ ID NO 1
<211> LENGTH: 3126
<212> TYPE: DNA
<213> ORGANISM: Homo sapiens

<400> SEQUENCE: 1

```
gaattccctc caaagcaaga caaatgactc acagagaaaa aagatggcag aaccaagggc      60
aactaaagcc gtcaggttct gaacagctgg tagatgggct ggcttactga aggacatgat     120
tcagactgtc ccggacccag cagctcatat caaggaactc tcctgatgaa tgcagtgtgg     180
ccaaaggcgg gaagatggtg ggcagcccag acaccgttgg gatgaactac ggcagctaca     240
tggaggagaa gcacatgcca cccccaaaca tgaccacgaa cgagcgcaga gttatcgtgc     300
```

```
cagcagatcc tacgctatgg agtacagacc atgtgcggca gtggctggag tgggcggtga    360
aagaatatgg ccttccagac gtcaacatct tgttattcca gaacatcgat gggaaggaac    420
tgtgcaagat gaccaaggac gacttccaga ggctcacccc cagctacaac gccgacatcc    480
ttctctcaca tctccactac ctcagagaga ctcctcttcc acatttgact tcagatgatg    540
ttgataaagc cttacaaaac tctccacggt taatgcatgc tagaaacaca gatttaccat    600
atgagccccc caggagatca gcctggaccg gtcacggcca ccccacgccc cagtcgaaag    660
ctgctcaacc atctccttcc acagtgccca aaactgaaga ccagcgtcct cagttagatc    720
cttatcagat tcttggacca acaagtagcc gccttgcaaa tccaggcagt ggccagatcc    780
agctttggca gttcctcctg gagctcctgt cggacagctc caactccagc tgcatcacct    840
gggaaggcac caacggggag ttcaagatga cggatcccga cgaggtggcc cggcgctggg    900
gagagcggaa gagcaaaccc aacatgaact acgataagct cagccgcgcc ctccgttact    960
actatgacaa gaacatcatg accaaggtcc atgggaagcg ctacgcctac aagttcgact   1020
tccacgggat cgcccaggcc ctccagcccc accccccgga gtcatctctg tacaagtacc   1080
cctcagacct cccgtacatg ggctcctatc acgcccaccc acagaagatg aactttgtgg   1140
cgccccaccc tccagccctc cccgtgacat cttccagttt ttttgctgcc ccaaacccat   1200
actggaattc accaactggg ggtatatacc ccaacactag gctccccacc agccatatgc   1260
cttctcatct gggcacttac tactaaagac ctggcggagg cttttcccat cagcgtgcat   1320
tcaccagccc atcgccacaa actctatcgg agaacatgaa tcaaaagtgc tcaagagga    1380 atgaaaaaag ctttactggg gctggggaag gaagccgggg aagagatcca aagactcttg   1440
ggagggagtt actgaagtct tactgaagtc ttactacaga aatgaggagg atgctaaaaa   1500
tgtcacgaat atggacatat catctgtgga ctgaccttgt aaaagacagt gtatgtagaa   1560
gcatgaagtc ttaaggacaa agtgccaaag aaagtggtct aagaaatgt ataaacttta    1620 gagtagagtt tgaatcccac taatgcaaac tgggatgaaa ctaaagcaat agaaacaaca   1680
cagttttgac ctaacatacc gtttataatg ccattttaag gaaaactacc tgtatttaaa   1740
aatagtttca tatcaaaaac aagagaaaag acacgagaga gactgtggcc catcaacaga   1800
cgttgatatg caactgcatg gcatgtgctg ttttggttga aatcaaatac attccgtttg   1860
atggacagct gtcagctttc tcaaactgtg aagatgaccc aaagttttcca actcctttac   1920 agtattaccg ggactatgaa ctaaaaggtg ggactgagga tgtgtataga gtgagcgtgt   1980
gattgtagac agaggggtga agaaggagga ggaagaggca gagaaggagg agaccaggct   2040
gggaaagaaa cttctcaagc aatgaagact ggactcagga catttgggga ctgtgtacaa   2100
tgagttatgg agactcgagg gttcatgcag tcagtgttat accaaaccca gtgttaggag   2160
aaaggacaca gcgtaatgga gaaagggaag tagtagaatt cagaaacaaa aatgcgcatc   2220
tctttctttg tttgtcaaat gaaaatttta actggaattg tctgatattt aagagaaaca   2280
ttcaggacct catcattatg tgggggcttt gttctccaca gggtcaggta agagatggcc   2340
ttcttggctg ccacaatcag aaatcacgca ggcattttgg gtaggcggcc tccagttttc   2400
ctttgagtcg cgaacgctgt gcgtttgtca gaatgaagta tacaagtcaa tgttttttccc   2460 ccttttttata taataattat ataacttatg catttataca ctacgagttg atctcggcca   2520
gccaaagaca cacgacaaaa gagacaaatcg atataatgtg gccttgaatt ttaactctgt   2580
atgcttaatg tttacaatat gaagttatta gttcttagaa tgcagaatgt atgtaataaa   2640
ataagcttgg cctagcatgg caaatcagat ttatacagga gtctgcattt gcacttttt    2700
```

| | |
|---|---|
| tagtgactaa agttgcttaa tgaaaacatg tgctgaatgt tgtggatttt gtgttataat | 2760 |
| ttactttgtc caggaacttg tgcaagggag agccaaggaa ataggatgtt tggcacccaa | 2820 |
| atggcgtcag cctctccagg tccttcttgc ctcccctcct gtcttttatt tctagcccct | 2880 |
| tttgaacag gaaggacccc ggggtttcaa ttggagcctc catatttatg cctggaagga | 2940 |
| aagaggccta tgaagctggg gttgtcattg agaaattcta gttcagcacc tggtcacaaa | 3000 |
| tcacccttaa ttctgctatg attaaaatac atttgttgaa cagtgaacaa gctaccactc | 3060 |
| gtaaggcaaa ctgtattatt actggcaaat aaagcgtcat ggatagctgc aatttctcac | 3120 |
| tttaca | 3126 |

<210> SEQ ID NO 2
<211> LENGTH: 3166
<212> TYPE: DNA
<213> ORGANISM: Homo sapiens

<400> SEQUENCE: 2

| | |
|---|---|
| gtccgcgcgt gtccgcgccc gcgtgtgcca gcgcgcgtgc cttggccgtg cgcgccgagc | 60 |
| cgggtcgcac taactccctc ggcgccgacg gcggcgctaa cctctcggtt attccaggat | 120 |
| cttttggagac ccgaggaaag ccgtgttgac caaaagcaag acaaatgact cacagagaaa | 180 |
| aaagatggca gaaccaaggg caactaaagc cgtcaggttc tgaacagctg gtagatgggc | 240 |
| tggcttactg aaggacatga ttcagactgt cccggaccca gcagctcata tcaaggaagc | 300 |
| cttatcagtt gtgagtgagg accagtcgtt gtttgagtgt gcctacggaa cgccacacct | 360 |
| ggctaagaca gagatgaccg cgtcctcctc cagcgactat ggacagactt ccaagatgag | 420 |
| cccacgcgtc cctcagcagg attggctgtc tcaaccccca gccagggtca ccatcaaaat | 480 |
| ggaatgtaac cctagccagg tgaatggctc aaggaactct cctgatgaat gcagtgtggc | 540 |
| caaaggcggg aagatggtgg gcagcccaga caccgttggg atgaactacg gcagctacat | 600 |
| ggaggagaag cacatgccac ccccaaacat gaccacgaac gagcgcagag ttatcgtgcc | 660 |
| agcagatcct acgctatgga gtacagacca tgtgcggcag tggctggagt gggcggtgaa | 720 |
| agaatatggc cttccagacg tcaacatctt gttattccag aacatcgatg ggaaggaact | 780 |
| gtgcaagatg accaaggacg acttccagag gctcaccccc agctacaacg ccgacatcct | 840 |
| tctctcacat ctccactacc tcagagagac tcctcttcca catttgactt cagatgatgt | 900 |
| tgataaagcc ttacaaaact ctccacggtt aatgcatgct agaaacacag atttaccata | 960 |
| tgagcccccc aggagatcag cctggaccgg tcacggccac cccacgcccc agtcgaaagc | 1020 |
| tgctcaacca tctccttcca cagtgcccaa aactgaagac cagcgtcctc agttagatcc | 1080 |
| ttatcagatt cttggaccaa caagtagccg ccttgcaaat ccaggcagtg ccagatcca | 1140 |
| gctttggcag ttcctcctgg agctcctgtc ggacagctcc aactccagct gcatcacctg | 1200 |
| ggaaggcacc aacggggagt tcaagatgac ggatcccgac gaggtggccc ggcgctgggg | 1260 |
| agagcggaag agcaaaccca acatgaacta cgataagctc agccgcgccc tccgttacta | 1320 |
| ctatgacaag aacatcatga ccaaggtcca tgggaagcgc tacgcctaca agttcgactt | 1380 |
| ccacgggatc gcccaggccc tccagcccca ccccggag tcatctctgt acaagtaccc | 1440 |
| ctcagacctc ccgtacatgg gctcctatca cgcccaccca cagaagatga actttgtggc | 1500 |
| gccccaccct ccagccctcc ccgtgacatc ttccagtttt tttgctgccc caaacccata | 1560 |
| ctggaattca ccaactgggg gtatataccc caacactagg ctcccacca gccatatgcc | 1620 |
| ttctcatctg ggcacttact actaaagacc tggcggaggc ttttcccatc agcgtgcatt | 1680 |

| | |
|---|---|
| caccagccca tcgccacaaa ctctatcgga gaacatgaat caaaagtgcc tcaagaggaa | 1740 |
| tgaaaaaagc tttactgggg ctggggaagg aagccgggga agagatccaa agactcttgg | 1800 |
| gagggagtta ctgaagtctt actacagaaa tgaggaggat gctaaaaatg tcacgaatat | 1860 |
| ggacatatca tctgtggact gaccttgtaa aagacagtgt atgtagaagc atgaagtctt | 1920 |
| aaggacaaag tgccaaagaa agtggtctta agaaatgtat aaactttaga gtagagtttg | 1980 |
| aatcccacta atgcaaactg ggatgaaact aaagcaatag aaacaacaca gttttgacct | 2040 |
| aacataccgt ttataatgcc atttttaagga aaactacctg tatttaaaaa tagtttcata | 2100 |
| tcaaaaacaa gagaaaagac acgagagaga ctgtggccca tcaacagacg ttgatatgca | 2160 |
| actgcatggc atgtgctgtt ttggttgaaa tcaaatacat tccgtttgat ggacagctgt | 2220 |
| cagcttttctc aaactgtgaa gatgacccaa agtttccaac tcctttacag tattaccggg | 2280 |
| actatgaact aaaaggtggg actgaggatg tgtatagagt gagcgtgtga ttgtagacag | 2340 |
| aggggtgaag aaggaggagg aagaggcaga gaaggaggag accaggctgg gaaagaaact | 2400 |
| tctcaagcaa tgaagactgg actcaggaca tttgggact gtgtacaatg agttatggag | 2460 |
| actcgagggt tcatgcagtc agtgttatac caaacccagt gttaggagaa aggacacagc | 2520 |
| gtaatggaga agggaagta gtagaattca gaaacaaaaa tgcgcatctc tttctttgtt | 2580 |
| tgtcaaatga aaattttaac tggaattgtc tgatatttaa gagaaacatt caggacctca | 2640 |
| tcattatgtg ggggctttgt tctccacagg gtcaggtaag agatggcctt cttggctgcc | 2700 |
| acaatcagaa atcacgcagg catttgggt aggcggcctc cagttttcct ttgagtcgcg | 2760 |
| aacgctgtgc gtttgtcaga atgaagtata caagtcaatg ttttttcccc tttttatata | 2820 |
| ataattatat aacttatgca tttatacact acgagttgat ctcggccagc caaagacaca | 2880 |
| cgacaaaaga gacaatcgat ataatgtggc cttgaatttt aactctgtat gcttaatgtt | 2940 |
| tacaatatga agttattagt tcttagaatg cagaatgtat gtaataaaat aagcttggcc | 3000 |
| tagcatggca aatcagattt atacaggagt ctgcatttgc actttttta gtgactaaag | 3060 |
| ttgcttaatg aaaacatgtg ctgaatgttg tggattttgt gttataattt actttgtcca | 3120 |
| ggaacttgtg caagggagag ccaaggaaat aggatgtttg gcaccc | 3166 |

<210> SEQ ID NO 3
<211> LENGTH: 2534
<212> TYPE: DNA
<213> ORGANISM: Homo sapiens

<400> SEQUENCE: 3

| | |
|---|---|
| gggattggga gggcttcttg caggctgctg ggctggggct aagggctgct cagtttcctt | 60 |
| cagcggggca ctgggaagcg ccatggcact gcagggcatc tcggtcgtgg agctgtccgg | 120 |
| cctggccccg ggcccgttct gtgctatggt cctggctgac ttcggggcgc gtgtggtacg | 180 |
| cgtggaccgg cccggctccc gctacgacgt gagccgcttg gccggggca agcgctcgct | 240 |
| agtgctggac ctgaagcagc cgcggggagc cgccgtgctg cggcgtctgt gcaagcggtc | 300 |
| ggatgtgctg ctggagccct tccgccgcgg tgtcatggag aaactccagc tgggcccaga | 360 |
| gattctgcag cgggaaaatc caaggcttat ttatgccagg ctgagtggat ttggccagtc | 420 |
| aggaagcttc tgccggttag ctggccacga tatcaactat ttggctttgt caggtgttct | 480 |
| ctcaaaaatt ggcagaagtg gtgagaatcc gtatgccccg ctgaatctcc tggctgactt | 540 |
| tgctggtggt ggccttatgt gtgcactggg cattataatg gctctttttg accgcacacg | 600 |
| cactggcaag ggtcaggtca ttgatgcaaa tatggtggaa ggaacagcat atttaagttc | 660 |

```
ttttctgtgg aaaactcaga aattgagtct gtgggaagca cctcgaggac agaacatgtt      720
ggatggtgga gcacctttct atacgactta caggacagca gatggggaat tcatggctgt      780
tggagcaata gaaccccagt tctacgagct gctgatcaaa ggacttggac taaagtctga      840
tgaacttccc aatcagatga gcatggatga ttggccagaa atgaagaaga agtttgcaga      900
tgtatttgca gagaagacga aggcagagtg gtgtcaaatc tttgacggca cagatgcctg      960
tgtgactccg gttctgactt ttgaggaggt tgttcatcat gatcacaaca aggaacgggg     1020
ctcgtttatc accagtgagg agcaggacgt gagcccccgc cctgcacctc tgctgttaaa     1080
caccccagcc atcccttctt tcaaaaggga tcctttcata ggagaacaca ctgaggagat     1140
acttgaagaa tttggattca gccgcgaaga gatttatcag cttaactcag ataaaatcat     1200
tgaaagtaat aaggtaaaag ctagtctcta acttccaggc ccacggctca agtgaatttg     1260
aatactgcat ttacagtgta gagtaacaca taacattgta tgcatggaaa catggaggaa     1320
cagtattaca gtgtcctacc actctaatca agaaaagaat tacagactct gattctacag     1380
tgatgattga attctaaaaa tggttatcat tagggctttt gatttataaa actttgggta     1440
cttatactaa attatggtag ttattctgcc ttccagtttg cttgatatat ttgttgatat     1500
taagattctt gacttatatt ttgaatgggt tctagtgaaa aaggaatgat atattcttga     1560
agacatcgat atacatttat ttacactctt gattctacaa tgtagaaaat gaggaaatgc     1620
cacaaattgt atggtgataa aagtcacgtg aaacagagtg attggttgca tccaggcctt     1680
ttgtcttggt gttcatgatc tccctctaag cacattccaa actttagcaa cagttatcac     1740
actttgtaat ttgcaaagaa aagtttcacc tgtattgaat cagaatgcct tcaactgaaa     1800
aaaacatatc caaataatg aggaaatgtg ttggctcact acgtagagtc cagagggaca     1860
gtcagtttta gggttgcctg tatccagtaa ctcggggcct gtttcccgt gggtctctgg      1920
gctgtcagct ttcctttctc catgtgtttg atttctcctc aggctggtag caagttctgg     1980
atcttatacc caacacacag caacatccag aaataaagat ctcaggaccc cccagcaagt     2040
cgttttgtgt ctccttggac tgagttaagt tacaagcctt tcttataacct gtctttgaca    2100
aagaagacgg gattgtcttt acataaaacc agcctgctcc tggagcttcc ctggactcaa     2160
cttcctaaag gcatgtgagg aaggggtaga ttccacaatc taatccgggt gccatcagag     2220
tagagggagt agagaatgga tgttgggtag gccatcaata aggtccattc tgcgcagtat     2280
ctcaactgcc gttcaacaat cgcaagagga aggtggagca ggtttcttca tcttacagtt     2340
gagaaaacag agactcagaa gggcttctta gttcatgttt cccttagcgc tcagtgatt     2400
ttttcatggt ggcttaggcc aaaagaaata tctaaccatt caatttataa ataattaggt     2460
ccccaacgaa ttaaatatta tgtcctacca acttattagc tgcttgaaaa atataataca     2520
cataaataaa aaaa                                                       2534

<210> SEQ ID NO 4
<211> LENGTH: 3923
<212> TYPE: DNA
<213> ORGANISM: Homo sapiens

<400> SEQUENCE: 4
acagaagaaa tagcaagtgc cgagaagctg gcatcagaaa aacagagggg agatttgtgt      60
ggctgcagcc gagggagacc aggaagatct gcatggtggg aaggacctga tgatacagag     120
gaattacaac acatatactt agtgtttcaa tgaacaccaa gataaataag tgaagagcta     180
gtccgctgtg agtctcctca gtgacacagg gctggatcac catcgacggc actttctgag    240
```

```
tactcagtgc agcaaagaaa gactacagac atctcaatgg caggggtgag aaataagaaa    300
ggctgctgac tttaccatct gaggccacac atctgctgaa atggagataa ttaacatcac    360
tagaaacagc aagatgacaa tataatgtct aagtagtgac atgttttttgc acatttccag   420 ccccttaaa tatccacaca cacaggaagc acaaaaggaa gcacagagat ccctgggaga     480
aatgcccggc cgccatcttg ggtcatcgat gagcctcgcc ctgtgcctgg tcccgcttgt   540
gagggaagga cattagaaaa tgaattgatg tgttccttaa aggatgggca ggaaaacaga    600
tcctgttgtg gatatttatt tgaacgggat tacagatttg aaatgaagtc acaaagtgag   660
cattaccaat gagaggaaaa cagacgagaa aatcttgatg gcttcacaag acatgcaaca   720
aacaaaatgg aatactgtga tgacatgagg cagccaagct ggggaggaga taaccacggg   780
gcagagggtc aggattctgg ccctgctgcc taaactgtgc gttcataacc aaatcatttc   840
atatttctaa ccctcaaaac aaagctgttg taatatctga tctctacggt tccttctggg   900
cccaacattc tccatatatc cagccacact cattttaat atttagttcc cagatctgta    960
ctgtgacctt tctacactgt agaataacat tactcatttt gttcaaagac ccttcgtgtt  1020
gctgcctaat atgtagctga ctgttttttcc taaggagtgt tctggcccag gggatctgtg  1080
aacaggctgg gaagcatctc aagatctttc cagggttata cttactagca cacagcatga  1140
tcattacgga gtgaattatc taatcaacat catcctcagt gtctttgccc atactgaaat   1200
tcatttccca cttttgtgcc cattctcaag acctcaaaat gtcattccat taatatcaca   1260
ggattaactt ttttttttaa cctggaagaa ttcaatgtta catgcagcta tgggaattta   1320
attacatatt ttgttttcca gtgcaaagat gactaagtcc tttatccctc ccctttgttt    1380
gatttttttt ccagtataaa gttaaaatgc ttagccttgt actgaggctg tatacagcac    1440
agcctctccc catccctcca gccttatctg tcatcaccat caacccctcc cataccacct   1500
aaacaaaatc taacttgtaa ttccttgaac atgtcaggac atacattatt ccttctgcct   1560
gagaagctct tccttgtctc ttaaatctag aatgatgtaa agttttgaat aagttgacta   1620
tcttacttca tgcaaagaag ggacacatat gagattcatc atcacatgag acagcaaata   1680
ctaaaagtgt aatttgatta taagagttta gataaatata tgaaatgcaa gagccacaga   1740
gggaatgttt atggggcacg tttgtaagcc tgggatgtga agcaaaggca gggaacctca   1800
tagtatctta tataatatac ttcatttctc tatctctatc acaatatcca acaagctttt   1860
cacagaattc atgcagtgca aatccccaaa ggtaacctt atccatttca tggtgagtgc    1920
gctttagaat tttggcaaat catactggtc acttatctca actttgagat gtgtttgtcc   1980
ttgtagttaa ttgaaagaaa tagggcactc ttgtgagcca ctttagggtt cactcctggc   2040
aataaagaat ttacaaagag ctactcagga ccagttgtta agagctctgt gtgtgtgtgt   2100
gtgtgtgtgt gagtgtacat gccaaagtgt gcctctctct cttgacccat tatttcagac   2160
ttaaaacaag catgttttca aatggcacta tgagctgcca atgatgtatc accaccatat   2220
ctcattattc tccagtaaat gtgataataa tgtcatctgt taacataaaa aaagtttgac   2280
ttcacaaaag cagctggaaa tggacaacca caatatgcat aaatctaact cctaccatca   2340
gctacacact gcttgacata tattgttaga agcacctcgc atttgtgggt tctcttaagc   2400
aaaatacttg cattaggtct cagctggggc tgtgcatcag gcggtttgag aaatattcaa   2460
ttctcagcag aagccagaat ttgaattccc tcatctttta ggaatcattt accaggtttg   2520 gagaggatt agacagctca ggtgctttca ctaatgtctc tgaacttctg tccctctttg    2580
tgttcatgga tagtccaata aataatgtta tctttgaact gatgctcata ggagagaata  2640
```

```
taagaactct gagtgatatc aacattaggg attcaaagaa atattagatt taagctcaca    2700
ctggtcaaaa ggaaccaaga tacaaagaac tctgagctgt catcgtcccc atctctgtga    2760
gccacaacca acagcaggac ccaacgcatg tctgagatcc ttaaatcaag gaaaccagtg    2820
tcatgagttg aattctccta ttatggatgc tagcttctgg ccatctctgg ctctcctctt    2880
gacacatatt agcttctagc ctttgcttcc acgactttta tcttttctcc aacacatcgc    2940
ttaccaatcc tctctctgct ctgttgcttt ggacttcccc acaagaattt caacgactct    3000
caagtctttt cttccatccc caccactaac ctgaatgcct agacccttat ttttattaat    3060
ttccaataga tgctgcctat gggctatatt gctttagatg aacattagat atttaaagct    3120
caagaggttc aaaatccaac tcattatctt ctctttcttt cacctccctg ctcctctccc    3180
tatattactg attgcactga acagcatggt ccccaatgta gccatgcaaa tgagaaaccc    3240
agtggctcct tgtggtacat gcatgcaaga ctgctgaagc cagaaggatg actgattacg    3300
cctcatgggt ggaggggacc actcctgggc cttcgtgatt gtcaggagca agacctgaga    3360
tgctccctgc cttcagtgtc ctctgcatct ccccttttcta atgaagatcc atagaatttg    3420
ctacatttga gaattccaat taggaactca catgttttat ctgccctatc aattttttaa    3480
acttgctgaa aattaagttt tttcaaaatc tgtccttgta aattactttt tcttacagtg    3540
tcttggcata ctatatcaac tttgattctt tgttacaact tttcttactc ttttatcacc    3600
aaagtggctt ttattctctt tattattatt attttctttt actactatat tacgttgtta    3660
ttattttgtt ctctatagta tcaatttatt tgatttagtt tcaatttatt tttattgctg    3720 actttttaaaa taagtgattc gggggtggg agaacagggg agggagagca ttaggacaaa    3780
tacctaatgc atgtgggact taaaacctag atgatgggtt gataggtgca gcaaaccact    3840
atggcacacg tatacctgtg taacaaacct acacattctg cacatgtatc ccagaacgta    3900
aagtaaaatt taaaaaaaag tga                                            3923

<210> SEQ ID NO 5
<211> LENGTH: 2390
<212> TYPE: DNA
<213> ORGANISM: Homo sapiens

<400> SEQUENCE: 5
agagccttcg tttgccaagt cgcctccaga ccgcagacat gaaacttgtc ttcctcgtcc      60
tgctgttcct cggggccctc ggactgtgtc tggctggccg taggaggagt gttcagtggt     120
gcgccgtatc ccaacccgag gccacaaaat gcttccaatg gcaaaggaat atgagaaaag     180
tgcgtggccc tcctgtcagc tgcataaaga gagactcccc catccagtgt atccaggcca     240
ttgcggaaaa cagggccgat gctgtgaccc ttgatggtgg tttcatatac gaggcaggcc     300 tggccccta caaactgcga cctgtagcgg cggaagtcta cgggaccgaa agacagccac     360
gaactcacta ttatgccgtg gctgtggtga agaagggcgg cagcttttcag ctgaacgaac     420 tgcaaggtct gaagtcctgc cacacaggcc ttcgcaggac cgctggatgg aatgtcccta     480
tagggacact tcgtccattc ttgaattgga cgggtccacc tgagcccatt gaggcagctg     540
tggccaggtt cttctcagcc agctgtgttc ccggtgcaga taaggacag ttccccaacc     600 tgtgtcgcct gtgtgcgggg acaggggaaa acaaatgtgc cttctcctcc caggaaccgt     660
acttcagcta ctctggtgcc ttcaagtgtc tgagagacgg ggctgagac gtggcttta     720 tcagagagag cacagtgttt gaggacctgt cagacgaggc tgaaagggac gagtatgagt     780
```

| | |
|---|---|
| tactctgccc agacaacact cggaagccag tggacaagtt caaagactgc catctggccc | 840 |
| gggtcccttc tcatgccgtt gtggcacgaa gtgtgaatgg caaggaggat gccatctgga | 900 |
| atcttctccg ccaggcacag gaaaagtttg gaaaggacaa gtcaccgaaa ttccagctct | 960 |
| ttggctcccc tagtgggcag aaagatctgc tgttcaagga ctctgccatt gggttttcga | 1020 |
| gggtgccccc gaggatagat tctgggctgt accttggctc cggctacttc actgccatcc | 1080 |
| agaacttgag gaaagtgag gaggaagtgg ctgcccggcg tgcgcgggtc gtgtggtgtg | 1140 |
| cggtgggcga gcaggagctg cgcaagtgta accagtggag tggcttgagc gaaggcagcg | 1200 |
| tgacctgctc ctcggcctcc accacagagg actgcatcgc cctggtgctg aaaggagaag | 1260 |
| ctgatgccat gagtttggat ggaggatatg tgtacactgc aggcaaatgt ggtttggtgc | 1320 |
| ctgtcctggc agagaactac aaatcccaac aaagcagtga ccctgatcct aactgtgtgg | 1380 |
| atagacctgt ggaaggatat cttgctgtgg cggtggttag gagatcagac actagcctta | 1440 |
| cctggaactc tgtgaaaggc aagaagtcct gccacaccgc cgtggacagg actgcaggct | 1500 |
| ggaatatccc catgggcctg ctcttcaacc agacgggctc ctgcaaattt gatgaatatt | 1560 |
| tcagtcaaag ctgtgcccct gggtctgacc cgagatctaa tctctgtgct ctgtgtattg | 1620 |
| gcgacgagca gggtgagaat aagtgcgtgc ccaacagcaa cgagagatac tacggctaca | 1680 |
| ctggggcttt ccggtgcctg gctgagaatg ctggagacgt tgcatttgtg aaagatgtca | 1740 |
| ctgtcttgca gaacactgat ggaaataaca atgaggcatg ggctaaggat ttgaagctgg | 1800 |
| cagactttgc gctgctgtgc ctcgatggca acggaagcc tgtgactgag gctagaagct | 1860 |
| gccatcttgc catggccccg aatcatgccg tggtgtctcg gatggataag gtggaacgcc | 1920 |
| tgaaacaggt gttgctccac caacaggcta aatttgggag aaatggatct gactgcccgg | 1980 |
| acaagttttg cttattccag tctgaaacca aaaaccttct gttcaatgac aacactgagt | 2040 |
| gtctggccag actccatggc aaaacaacat atgaaaaata tttgggacca cagtatgtcg | 2100 |
| caggcattac taatctgaaa aagtgctcaa cctccccccct cctggaagcc tgtgaattcc | 2160 |
| tcaggaagta aaaccgaaga agatggccca gctccccaag aaagcctcag ccattcactg | 2220 |
| cccccagctc ttctccccag gtgtgttggg gccttggcct ccctgctga aggtggggat | 2280 |
| tgcccatcca tctgcttaca attccctgct gtcgtcttag caagaagtaa aatgagaaat | 2340 |
| tttgttgata ttctctcctt aaaaaaaaaa aaaaaaaaa aaaaaaaaaa | 2390 |

```
<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
```

| | |
|---|---|
| gtcaagatgc taccgttcag | 20 |

```
<210> SEQ ID NO 7
<211> LENGTH: 29
<212> TYPE: DNA
<213> ORGANISM: Homo sapiens

<400> SEQUENCE: 7
```

| | |
|---|---|
| agagaaacat tcaggacctc atcattatg | 29 |

<210> SEQ ID NO 8
<211> LENGTH: 19
<212> TYPE: DNA
<213> ORGANISM: Homo sapiens

<400> SEQUENCE: 8
gcagccaaga aggccatct                                          19

<210> SEQ ID NO 9
<211> LENGTH: 16
<212> TYPE: DNA
<213> ORGANISM: Homo sapiens

<400> SEQUENCE: 9
ttgttctcca cagggt                                             16

<210> SEQ ID NO 10
<211> LENGTH: 19
<212> TYPE: DNA
<213> ORGANISM: Homo sapiens

<400> SEQUENCE: 10
caggtccttc ttgcctccc                                          19

<210> SEQ ID NO 11
<211> LENGTH: 22
<212> TYPE: DNA
<213> ORGANISM: Homo sapiens

<400> SEQUENCE: 11
tatggaggct ccaattgaaa cc                                      22

<210> SEQ ID NO 12
<211> LENGTH: 33
<212> TYPE: DNA
<213> ORGANISM: Homo sapiens

<400> SEQUENCE: 12
tgtcttttat ttctagcccc ttttggaaca gga                          33

<210> SEQ ID NO 13
<211> LENGTH: 50
<212> TYPE: PRT
<213> ORGANISM: Homo sapiens

<400> SEQUENCE: 13

Cys Lys Ala Leu Gln Asn Ser Pro Arg Leu Met His Ala Arg Asn Thr
 1               5                  10                  15

Asp Leu Pro Tyr Glu Pro Pro Arg Arg Ser Ala Trp Thr Gly His Gly
            20                  25                  30

His Pro Thr Pro Gln Ser Lys Ala Ala Gln Pro Ser Pro Ser Thr Val
        35                  40                  45

Pro Lys
    50

<210> SEQ ID NO 14
<211> LENGTH: 49
<212> TYPE: PRT
<213> ORGANISM: Homo sapiens

```
<400> SEQUENCE: 14

Cys Asp Phe His Gly Ile Ala Gln Ala Leu Gln Pro His Pro Pro Glu
1               5                   10                  15

Ser Ser Leu Tyr Lys Tyr Pro Ser Asp Leu Pro Tyr Met Gly Ser Tyr
            20                  25                  30

His Ala His Pro Gln Lys Met Asn Phe Val Ala Pro His Pro Pro Ala
        35                  40                  45

Leu

<210> SEQ ID NO 15
<211> LENGTH: 23
<212> TYPE: DNA
<213> ORGANISM: Homo sapiens

<400> SEQUENCE: 15
cacatttcca gcccctttaa ata                                        23

<210> SEQ ID NO 16
<211> LENGTH: 17
<212> TYPE: DNA
<213> ORGANISM: Homo sapiens

<400> SEQUENCE: 16
gggcgaggct catcgat                                               17

<210> SEQ ID NO 17
<211> LENGTH: 28
<212> TYPE: DNA
<213> ORGANISM: Homo sapiens

<400> SEQUENCE: 17
ggaagcacag agatccctgg gagaaatg                                   28
```